United States Patent
Honma et al.

(10) Patent No.: US 6,521,429 B2
(45) Date of Patent: Feb. 18, 2003

(54) POLYHYDROXYALKANOATES AND METHOD OF PRODUCING THEM BY UTILIZING MICROORGANISMS

(75) Inventors: Tsutomu Honma, Atsugi (JP); Toyoko Kobayashi, Yokohama (JP); Tetsuya Yano, Atsugi (JP); Shin Kobayashi, Kawasaki (JP); Takeshi Imamura, Chigasaki (JP); Sakae Suda, Ushiku (JP); Takashi Kenmoku, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 67 days.

(21) Appl. No.: 09/745,476

(22) Filed: Dec. 26, 2000

(65) Prior Publication Data

US 2001/0029039 A1 Oct. 11, 2001

(30) Foreign Application Priority Data

| Dec. 27, 1999 | (JP) | 11-371864 |
|---|---|---|
| Dec. 27, 1999 | (JP) | 11-371867 |
| Dec. 27, 1999 | (JP) | 11-371868 |
| Dec. 27, 1999 | (JP) | 11-371869 |
| Jan. 31, 2000 | (JP) | 2000-023024 |
| Jan. 31, 2000 | (JP) | 2000-023025 |
| Nov. 28, 2000 | (JP) | 2000-361323 |

(51) Int. Cl.$^7$ .............................. C12P 7/62; C08G 63/06
(52) U.S. Cl. ........................................ 435/135; 428/361
(58) Field of Search ............................. 435/135; 528/361

(56) References Cited

U.S. PATENT DOCUMENTS

| 5,200,332 A | 4/1993 | Yamane et al. |
| 5,292,860 A | 3/1994 | Shiotani et al. |
| 5,334,698 A | 8/1994 | Witholt et al. |

FOREIGN PATENT DOCUMENTS

| JP | 5-159 | 1/1993 |
| JP | 5-7492 | 1/1993 |
| JP | 5-49487 | 3/1993 |
| JP | 5-93049 | 4/1993 |
| JP | 6-169980 | 6/1994 |
| JP | 6-169988 | 6/1994 |
| JP | 6-225921 | 8/1994 |
| JP | 7-265065 | 10/1995 |
| JP | 9-191893 | 7/1997 |
| JP | 2-642937 | 8/1997 |
| JP | 2-989175 | 12/1999 |
| WO | 92/22569 | 12/1992 |

OTHER PUBLICATIONS

A. Steinbüchel et al., "Diversity of bacterial Polyhydroxyalcanoic Acids," vol. 128 *FEMS Microbiology Letters* 219–228 (1995).

K. Fritzsche et al., "An Unusual Bacterial Polyester With a Phenyl Pendant Group," vol. 191 *Makromol. Chem.* 1957–1965 (1990).

(List continued on next page.)

Primary Examiner—Jon P. Weber
(74) Attorney, Agent, or Firm—Fitzpatrick, Cella, Harper & Scinto

(57) ABSTRACT

A microbial polyhydroxyalkanoate which comprises one or more of monomer units represented by Formula (1),

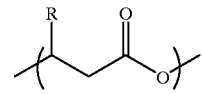

(1)

where R is at least one selected from the group represented by any one of Formulas (2), (3) and (4);

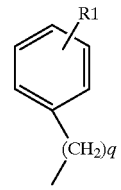

(2)

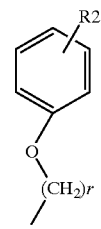

(3)

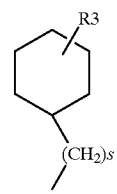

(4)

in Formula (2), R1 is selected from the group consisting of hydrogen atom (H), halogen atom, —CN, —NO$_2$, —CF$_3$, —C$_2$F$_5$ and —C$_3$F$_7$, and q is an integer of 1 to 8;

in Formula (3), R2 is selected from the group consisting of hydrogen atom (H), halogen atom, —CN, —NO$_2$, —CF$_3$, —C$_2$F$_5$ and —C$_3$F$_7$, and r is an integer of 1 to 8;

in Formula (4), R3 is selected from the group consisting of hydrogen atom (H), halogen atom, —CN, —NO$_2$, —CF$_3$, —C$_2$F$_5$ and —C$_3$F$_7$, and s is an integer of 1 to 8. The production method is also disclosed.

5 Claims, 29 Drawing Sheets

OTHER PUBLICATIONS

Y.B. Kim et al., "Preparation and Characterization of Poly(β–hydroxyalkanoates) Obtained from *Pseudomonas oleovorans* Grown with Mixtures of 5–Phenylvaleric Acid and n–Alkanoic Acids," vol. 24 *Macromolecules* 5256–5260 (1991).

H. Ritter et al., "Bacterial Production of Polyesters Bearing Phenoxy Groups in the Side Chains, 1 Poly(3–hydroxy–5–phenoxypentanoate–co–3hydroxy–9–phenoxynonanoate) from *Pseudomonas oleovorans*," vol. 195 *Macromol. Chem. Phys.* 1665–1672 (1994).

Y.B. Kim et al., "Poly–3–hydroxyalkanoates Produced from *Pseudomonas oleovorans* Grown with ω–Phenoxyalkanoates," vol. 29 Macromolecules 3432–3435 (1996).

M. Andújar et al., "Polyesters Produced by *Pseudomonas oleovorans* Containing Cyclohexyl Groups," 30 *Macromolecules* 1611–1615 (1997).

H. Vogel et al., "Acetylornithinase of *Escherichia coli*: Partial Purification and Some Properties," 218 *J. Biol. Chem.* 97–106 (1956).

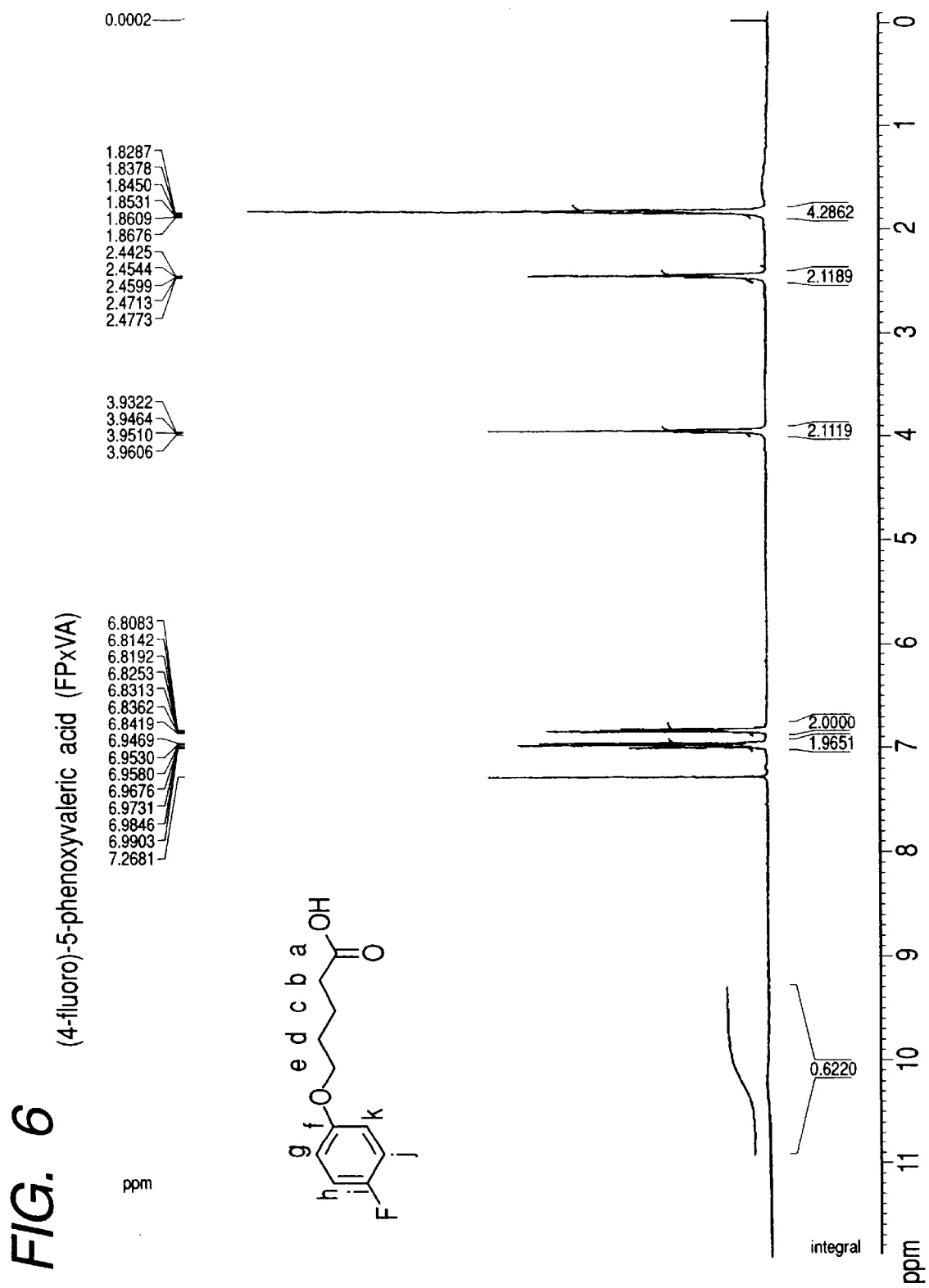
FIG. 6  (4-fluoro)-5-phenoxyvaleric acid (FPxVA)

FIG. 12

Pseudomonas jessenii P161; 16S rRNA

TGAACGCTGGCGGCAGGCCTAACACATGCAAGTCGAGCGGATGACGGGAGCTTGCTC
CTGAATTCAGCGGCGGACGGGTGAGTAATGCCTAGGAATCTGCCTGGTAGTGGGGGAC
AACGTCTCGAAAGGGACGCTAATACCGCATACGTCCTACGGGAGAAAGCAGGGGACCT
TCGGGCCTTGCGCTATCAGATGAGCCTAGGTCGGATTAGCTAGTTGGTGAGGTAATGG
CTCACCAAGGCGACGATCCGTAACTGGTCTGAGAGGATGATCAGTCACACTGGAACTG
AGACACGGTCCAGACTCCTACGGGAGGCAGCAGTGGGGAATATTGGACAATGGGCGAA
AGCCTGATCCAGCCATGCCGCGTGTGTGAAGAAGGTCTTCGGATTGTAAAGCACTTTAA
GTTGGGAGGAAGGGCATTAACCTAATACGTTAGTGTTTTGACGTTACCGACAGAATAAG
CACCGGCTAACTCTGTGCCAGCAGCCGCGGTAATACAGAGGGTGCAAGCGTTAATCGG
AATTACTGGGCGTAAAGCGCGCGTAGGTGGTTTGTTAAGTTGGATGTGAAAGCCCCGG
GCTCAACCTGGGAACTGCATTCAAAACTGACAAGCTAGAGTATGGTAGAGGGTGGTGGA
ATTTCCTGTGTAGCGGTGAAATGCGTAGATATAGGAAGGAACACCAGTGGCGAAGGCG
ACCACCTGGACTGATACTGACACTGAGGTGCGAAAGCGTGGGGAGCAAACAGGATTAG
ATACCCTGGTAGTCCACGCCGTAAACGATGTCAACTAGCCGTTGGGAGCCTTGAGCTCT
TAGTGGCGCAGCTAACGCATTAAGTTGACCGCCTGGGGAGTACGGCCGCAAGGTTAAA
ACTCAAATGAATTGACGGGGGCCCGCACAAGCGGTGGAGCATGTGGTTTAATTCGAAG
CAACGCGAAGAACCTTACCAGGCCTTGACATCCAATGAACTTTCCAGAGATGGATGGGT
GCCTTCGGGAACATTGAGACAGGTGCTGCATGGCTGTCGTCAGCTCGTGTCGTGAGAT
GTTGGGTTAAGTCCCGTAACGAGCGCAACCCTTGTCCTTAGTTACCAGCACGTAATGGT
GGGCACTCTAAGGAGACTGCCGGTGACAAACCGGAGGAAGGTGGGGATGACGTCAAG
TCATCATGGCCCTTACGGCCTGGGCTACACACGTGCTACAATGGTCGGTACAGAGGGT
TGCCAAGCCGCGAGGTGGAGCTAATCCCACAAAACCGATCGTAGTCCGGATCGCAGTC
TGCAACTCGACTGCGTGAAGTCGGAATCGCTAGTAATCGCGAATCAGAATGTCGCGGT
GAATACGTTCCCGGGCCTTGTACACACCGCCCGTCACACCATGGGAGTGGGTTGCACC
AGAAGTAGCTAGTCTAACCTTCGGGAGGACGGTTACCACGGTGTGATTCATGACTGGG
GTGAAGTCGTACCAAGGTAGCCGTAGGGGAACCTGCGGCTGGATCAC

SCAN NO.: 5788   BACKGROUND: (5293-6136)
PEAK NUMBER: 42   RETENTION TIME: 51.725
BASE PEAK: 94.05   (62651)

SCAN NO.: 9336   BACKGROUND: (8904-9732)
PEAK NUMBER: 34   RETENTION TIME: 81.292
BASE PEAK: 85.10   (38358)

SCAN NO.: 5790   BACKGROUND: (5377-6336)
PEAK NUMBER: 61   RETENTION TIME: 51.742
BASE PEAK: 131.15   ( 162050)

SCAN NO.: 9351   BACKGROUND: (8851-9812)
PEAK NUMBER: 65   RETENTION TIME: 81.417
BASE PEAK: 94.10   ( 223818)

SCAN NO.: 7400   BACKGROUND: (6837-8167)
PEAK NUMBER: 42   RETENTION TIME: 65.158
BASE PEAK: 71.10   (170041)

SCAN NO.: 11816   BACKGROUND: (11628-11978)
PEAK NUMBER: 24   RETENTION TIME: 101.958
BASE PEAK: 94.10   (20975)

SCAN NO.: 5787  BACKGROUND: (5691-5868)
PEAK NUMBER: 29  RETENTION TIME: 51.717
BASE PEAK: 131.15  (30678)

SCAN NO.: 9334  BACKGROUND: (9108-9553)
PEAK NUMBER: 35  RETENTION TIME: 81.275
BASE PEAK: 94.05  (48597)

SCAN NO.: 15229 BACKGROUND: (15043-15439)
PEAK NUMBER: 14 RETENTION TIME: 130.400
BASE PEAK: 94.10 ( 5966)

SCAN NO.: 5774 BACKGROUND: (5647-5930)
PEAK NUMBER: 43 RETENTION TIME: 51.608
BASE PEAK: 131.15 ( 84615)

SCAN NO.: 9318  BACKGROUND: ( 9062-9693 )
PEAK NUMBER: 41  RETENTION TIME: 81.142
BASE PEAK: 94.10  ( 59324)

SCAN NO.: 15217  BACKGROUND: ( 15110-15331 )
PEAK NUMBER: 11  RETENTION TIME: 130.300
BASE PEAK: 94.10  ( 4942)

SCAN NO.: 4827  BACKGROUND: (4668-5023)
PEAK NUMBER: 90  RETENTION TIME: 43.717
BASE PEAK: 104.15  ( 1344409)

SCAN NO.: 3556  BACKGROUND: (3537-3574)
PEAK NUMBER: 31  RETENTION TIME: 33.125
BASE PEAK: 91.15  ( 32184)

SCAN NO.: 4824   BACKGROUND: (4613-5115)
PEAK NUMBER: 90   RETENTION TIME: 43.692
BASE PEAK: 104.20   ( 1343658)

SCAN NO.: 4142   BACKGROUND: (4102-4184)
PEAK NUMBER: 68   RETENTION TIME: 38.008
BASE PEAK: 91.10   ( 262653)

POLYHYDROXYALKANOATES AND METHOD OF PRODUCING THEM BY UTILIZING MICROORGANISMS

BACKGROUND OF THE INVENTION

1. Field of the Invention

The present invention relates to novel polyhydroxyalkanoate (PHA), as well as a method of producing such a novel PHA by utilizing microorganisms.

2. Related Background Art

Synthetic polymers derived from petroleum have been used as plastics etc. for a long time. Recently, the treatment of the used plastics has become one of serious social problems. These synthetic polymers have advantages of hard-to-decompose have been used in the place of metal or glass materials. On mass consumption and mass disposal, however, this feature of hard-to-decompose makes them accumulated in waste-disposal facilities, or when they are burned, it causes increased carbon dioxide exhaust, and harmful substances such as dioxin and endocrine-disruptors may be generated to cause environmental pollution.

On the other hand, polyesters produced by microorganisms (hereinafter referred to as "microbial polyesters") can be biologically degraded to be incorporated in a natural recycling system. Thus they would not remain in natural environment without causing pollution, in contrast to the numerous usual synthetic polymer compounds. Furthermore, since the biodegradability dispenses with incinerating treatment, microbial polyesters are effective from the standpoint of the prevention of air pollution and global warming, and usable as plastics to maintain the environment. In addition, their potential as soft materials for medical use has been investigated (Japanese Patent Application Laid-Open No. 5-159, Nos. 6-169980, 6-169988, 6-225921, etc.).

Heretofore, various bacteria have been reported to produce and accumulate PHB or copolymers of other hydroxyalkanoic acids in the cells (Handbook of Biodegradable Plastics, ed. by Biodegradable Plastics Society, published by N.T.S., p. 178–197 (1995)). Microbial PHA thus obtained is known to have various compositions and structures depending on the class of microorganisms used, medium composition, culture conditions, etc. during production, and many studies related to the control of composition and structure of PHA products have been conducted to improve PHA properties.

For example, *Alcaligenes eutropus* H16 ATCC No. 17699 and its mutants can produce copolymers of 3-hydroxybutyric acid (3HB) and 3-hydroxyvaleric acid (3HV) at a various composition ratio by varying carbon sources during culture (Published Japanese Translation of PCT International Publication Nos. 6-15604, 7-14352, 8-19227, etc.).

Japanese Patent No. 2642937 discloses that *Pseudomonas oleovorans* ATCC29347, when given acyclic aliphatic hydrocarbons as a carbon source, produces PHA having a monomer unit of 3-hydroxyalkanoate of 6 to 12 carbon atoms.

Japanese Patent Application Laid-Open No. 5-74492 discloses the method comprising contacting a microorganism of Methylobacterium sp., Paracoccus sp., Alcaligenes sp., or Pseudomonas sp. with a primary alcohol of 3 to 7 carbon atoms, thereby allowing to produce a copolymer of 3HB and 3HV.

Japanese Patent Application Laid-Open Nos. 5-93049 and 7-265065 disclose that *Aeromonas caviae* can produce, by using oleic acid and olive oil as carbon sources, a binary copolymer of 3HB and 3-hydroxyhexanoic acid (3HHx).

Japanese Patent Application Laid-Open No. 9-191893 discloses that *Comamonas acidovorans* IFO13852 can produce, by using gluconic acid and 1,4-butanediol as a carbon source, a polyester having monomer units of 3HB and 4-hydroxybutyric acid.

Furthermore, certain microorganisms has been reported to produce PHA having various substituents such as groups derived from unsaturated hydrocarbons, ester group, allyl group, cyano group, nitro group, groups derived from halogenated hydrocarbon, and epoxide. Thus, there have been started several attempts to improve the properties of microbial PHA by using such a technique. Examples of microbial polyester having such substituents are described in FEMS Microbiology Letters, 128 (1995) p.219–228, in detail. Makromol. Chem., 191, 1957–1965, 1990, Macromolecules, 24, 5256–5260, 1991, and Chirality, 3, 492–494, 1991 report that *Pseudomonas oleovorans* produces PHA comprising a monomer unit of 3-hydroxy-5-phenylvaleric acid (3HPV), and changes in polymer properties probably due to the presence of the monomer unit of 3HPV.

As stated above, microbial PHA of various compositions/ structures can be obtained by varying the microorganism, medium composition, culture conditions, etc. for polymer production. Their physical properties, however, are still insufficient for plastics. In order to further extend the application field, it is important to investigate more extensively the improvement of properties, and it is, therefore, essential to develop and search PHA made of structurally various monomer units, methods of producing them, as well as microorganisms capable of efficiently producing the desired PHA.

On the other hand, those PHA having introduced substituents in the side chains as described above, can be expected to be developed as "functional polymer" having useful functions and properties by selecting the substituent to be introduced according to the desired properties, etc. It is also important to develop and search PHA satisfying both functionality and biodegradability, methods of producing them, as well as microorganisms capable of efficiently producing desired PHA.

One example of such PHA having a substituent introduced in side chains is PHA having phenoxy in side chains.

For example, Macromol. Chem. Phys., 195, 1655–1672 (1994) reports that *Pseudomonas oleovorans* produces PHA containing units of 3-hydroxy-5-phenoxyvaleric acid and 3-hydroxy-9-phenoxynonanoic acid, from 11-phenoxyundecanoic acid.

Macromolecules, 29, 3432–3435 (1996) also reports that *Pseudomonas oleovorans* can be used to produce PHA containing 3-hydroxy-4-phenoxyburyric acid and 3'-hydroxy-6-phenoxyhexanoic acid units from 6-phenoxyhexanoic acid, PHA containing 3-hydroxy-6-phenoxyhexanoic acid and 3-hydroxy-8-phenoxyoctanoic acid units from 8-phenoxyoctanoic acid, and PHA containing 3-hydroxy-5-phenoxyvaleric acid and 3-hydroxy-7-phenoxyheptanoic acid units from 11-phenoxyunndecanoic acid. The polymer yield is as follows.

Furthermore, Can. J. Microbiol., 41, 32–43 (1995) reports that when given octanoic acid and p-cyanophenoxyhexanoic acid or p-nitrophenoxyhexanoic acid as substrates, *Pseudomonas oleovorans* ATCC29347 or *Pseudomonas*

*putida* KT2442 can produce PHA containing a monomer unit of 3-hydroxy-p-cyanophenoxyhexanoic acid or 3-hydroxy-p-nitrophenoxyhexanoic acid.

Japanese Patent No. 2989175 describes a homopolymer consisting of 3-hydroxy-5-(monofluorophenoxy)pentanoate (3H5(MFP)P) unit or 3-hydroxy-5-(difluorophenoxy) pentanoate (3H5(DFP)P) unit, a copolymer containing at least one of 3H5(MFP)P unit and 3H5(DFP)P unit, *Pseudomonas putida* which can produce such polymers; and a method of producing the above polymers by using a Pseudomonas sp.

Such productions are conducted by "2-step culture" described below. Culture period: step 1 - 24 hours; step 2 - 96 hours.

Substrates in each step and polymers obtained are as follows.
(1) Polymer obtained: 3H5(MFP)P homopolymer
   Substrates in step 1: citric acid, yeast extract
   Substrates in step 2: monofluorophenoxyundecanoic acid
(2) Polymer obtained: 3H5(DFP)P homopolymer
   Substrates in step 1: citric acid, yeast extract
   Substrates in step 2: difluorophenoxyundecanoic acid
(3) Polymer obtained: 3H5(MFP)P copolymer
   Substrates in step 1: octanoic or nonanoic acid, yeast extract
   Substrates in step 2: monofluorophenoxyundecanoic acid
(4) Polymer obtained: 3H5(MFP)P homopolymer
   Substrates in step 1: octanoic or nonanoic acid, yeast extract
   Substrates in step 2: difluorophenoxyundecanoic acid It describes that the microorganism can assimilate substituted aliphatic acids of a medium chain length to produce a polymer having phenoxy group substituted with 1 to 2 fluorine atoms at the end of a side chain, and such a polymer has stereoregularity and water repellency while keeping a high melting point and a good processibility.

It has been reported a PHA containing a cyclohexyl group in its monomer unit is expected to exhibit polymer properties differing from a PHA containing an usual aliphatic hydroxyalkanoic acid as a unit, as well as its production by *Pseudomonas oleovorans* (Macromolecules, 30, 1611–1615 (1997)).

According to this report, *Pseudomonas oleovorans* is cultured in a medium containing nonanoic acid (hereinafter referred to as NA), and 4-cyclohexylbutyric acid (hereinafter referred to as CHBA) or 5-cyclohexylvaleric acid (hereinafter referred to as CHVA) to obtain PHA made of a cyclohexyl-containing unit and a unit derived from nonanoic acid (each proportion is unknown).

By varying the ratio of CHBA to NA under the conditions that the total concentration of substrates is 20 mM, the results shown in Table 2 were obtained. In Table 2, CDW: Cell mass (dry weight) (mg/L); PDW: polymer mass (dry weight) (mg/L); and Yield: PDW/CDW (%)

In this case, however, the polymer yield per culture (w/v) was insufficient, and nonanoic acid-derived aliphatic hydroxyalkanoic acid units were present in the resultant PHA.

As described above, to produce PHA having various introduced substituents in the side chain, as with the above *Pseudomonas oleovorans*, an alkanoate having a substituent to be introduced has been utilized not only as a polymer raw material but also as a carbon source for growth.

Such a method to utilize an alkanoate having a substituent to be introduced into the polymer, not only as a raw material for the polymer but also as a carbon source for growth expects to supply the carbon source and energy source as the acetyl-CoA formed by β-oxidation of the alkanoate. In such a method, however, acetyl-CoA would not be formed by β-oxidation unless the substrate has a certain chain length, so that there is a serious problem that the alkanoate available as the substrate for PHA is limited. In general, β-oxidation generates a new substrate, of which chain length is shorter by two methylene units at a time, and they are incorporated as the monomer units of PHA, synthesized PHA is often a copolymer consisting of monomer units each differing by two methylene chains in the chain length. In the foregoing report, the produced polymer is a copolymer consisting of three monomer units, that is, 3-hydroxy-8-phenoxyoctanoic acid derived from the substrate 8-phenoxyoctanoic acid, 3-hydroxy-6-phenoxyhexanoic acid and 3-hydroxy-4-phenoxybutyric acid being metabolic by-products. Thus, PHA consisting of a single monomer unit is hard to obtain by this method. Furthermore, in the method depending on the acetyl-CoA formed by β-oxidation as the carbon and energy source, there are such problems as slow growth rate of the microorganism, slow synthesis of PHA, and low yield of PHA.

Thus, usually the microorganism is grown in a medium containing a medium-length aliphatic acid such as octanoic acid and nonanoic acid, etc. as a carbon source for growth in addition to the alkanoate having a substituent to be introduced, and then PHA is extracted.

The PHA produced by the above method, however, contains monomer units having a substituent to be introduced and monomer units derived from the carbon source for growth (for example, 3-hydroxyoctanoic acid and 3-hydroxynonanoic acid). The polymer of such a medium chain length (mcl) monomer unit is adhesive at ambient temperature, and, when mixed with the desired PHA, significantly lowers the glass transition point (Tg). Thus, to obtain a polymer being solid at ambient temperature, contamination of mcl-monomer units is undesirable. In addition, the presence of heterogeneous side chains is known to interfere with intramolecular or intermolecular interactions due to the side chain structure, and significantly affects crystallinity and orientation. In order to improve the polymer properties and endowment of functions, a mixture of such mcl-monomer units is a serious problem. One means to solve this problem is to add a purification step to separate and remove such "unintended" polymers of mcl-monomer units derived from the carbon source for growth and to obtain PHA consisting only of a monomer unit having a specific substituent. Nevertheless, operations become troublesome and a significant decrease of the yield is inevitable. A more important problem is the fact that, if the intended monomer units form a copolymer with the unintended monomer units, it is very difficult to remove the unintended monomer units only. In particular, when the PHA containing monomer units having such groups as the groups derived from unsaturated hydrocarbons, ester groups, aryl group, cyano group, nitro group, groups derived from halogenated hydrocarbons and epoxide as side chain structure, mcl-monomer units often form a copolymer with the intended monomer unit, so it is very difficult to remove mcl-monomer units after the PHA synthesis.

SUMMARY OF THE INVENTION

The present invention can solve the above problems. The object of the present invention is to provide a PHA containing monomer units of various structures having substituents useful for device materials, medical materials, etc. in the side chains. Another object of the present invention is to provide a method of producing such a PHA by utilizing microorganisms, especially a method of producing PHA with little contamination of monomer units and in a high yield. The other object of the present invention is to provide novel PHA consisting only of the desired monomer units without contamination of unintended monomer units, as well as a method of producing such a PHA by utilizing microorganisms.

In order to solve the above problems, especially to develop PHA having substituted or unsubstituted phenoxy group, phenyl group and cyclohexyl group in the side chains, being useful as device materials, medical materials, etc., the present inventor have extensively searched for novel microorganisms capable of producing and accumulating PHA in the cell, and a method of producing the desired PHA by utilizing novel microorganisms.

Further, to develop a method of obtaining efficiently the desired PHA without mixing of unintended monomer units, the present inventors made extensive study and found that by culturing the microorganism in a medium supplemented with yeast extract in addition to an alkanoate having a desired atomic group, it is possible to produce selectively only the desired PHA without being mixed with unintended monomer units or with reduced incorporation of unintended monomer units, then completed the present invention.

Thus, the method of producing novel PHA of the present invention is characterized by culturing a microorganism in a culture medium containing an alkanoate and yeast extract, which microorganism is capable of producing the object PHA by utilizing the alkanoate in the medium as a low material. In particular, the method of producing PHA of the present invention can be carried out in accordance with the embodiments described below.

According to one aspect of the present invention, there is provided a polyhydroxyalkanoate comprising one or more of monomer units represented by Formula (1),

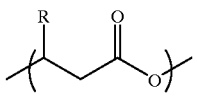
(1)

where R is at least one selected from the group represented by any one of Formulas (2), (3) and (4);

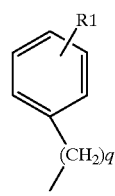
(2)

-continued

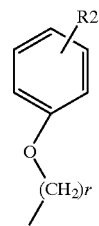
(3)

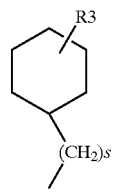
(4)

in Formula (2), R1 is selected from the group consisting of hydrogen atom (H), halogen atom, —CN, —NO$_2$, —CF$_3$, —C$_2$F$_5$ and —C$_3$F$_7$, and q is an integer of 1 to 8;

in Formula (3), R2 is selected from the group consisting of hydrogen atom (H), halogen atom, —CN, —NO$_2$, —CF$_3$, —C$_2$F$_5$ and —C$_3$F$_7$, and r is an integer of 1 to 8;

in Formula (4), R3 is selected from the group consisting of hydrogen atom (H), halogen atom, —CN, —NO$_2$, —CF$_3$, —C$_2$F$_5$ and —C$_3$F$_7$, and s is an integer of 1 to 8;

provided that following R is not selected:

when one kind of R is selected:
R being R1=H and q=2, R being R1=H and q=3 in Formula (2),
R being R2=halogen and r=2, or R being R2=—CN and r=3 and
R being R2=—NO$_2$ and r=3 in Formula (3);

when two kinds of R are selected:
a combination of R being R1=H and q=3 and 5 respectively in Formula (2),
a combination of R being R2=H and r=2 and 4 respectively,
a combination of R being R2=H and r=2 and 6 respectively, and
a combination of R being R2=halogen and r=2 and 4 respectively in Formula (3);

when three kinds of R are selected:
a combination of R being R1=H and q=3, 5 and 7 respectively in Formula (2),
a combination of R being R2=H and r=1, 3 and 5 respectively, and a combination of R being R2=H and r=2, 4 and 6 respectively in Formula (3).

According to another aspect of the present invention, there is provided a process of producing a polyhydroxyalkanoate comprising the step of:

culturing a microorganism in a culture medium containing a raw material alkanoate and an yeast extract, wherein the microorganism produces a polyhydroxyalkanoate utilizing the alkanoate.

The present invention provides a method for producing polyhydroxyalkanoate, which uses ω-substituted-straight-chain alkanoic acid, of which terminal of a chain is substituted by any one of 6-carbon ring atomic group of a substituted or unsubstituted phenyl group, a substituted or unsubstituted phenoxy group, and a substituted or unsubstituted cyclohexyl group, as the material and also which contains corresponding ω-substituted-3-hydroxy-alkanoic acid as the monomer units, and also provides microorganisms suitable for selective production of polyhydroxyalkanoate having 6-carbon ring atomic group in the terminal of these side chains. Various polyhydroxyalkanoate, of which production by microorganisms becomes first possible according to the present invention, in an inorganic culture medium containing the yeast extract and the ω-substituted-straight-chain alkanoic acid as the material, a microorganism belonging to the genus Pseudomonas, for example, is cultured to work on the ω-substituted-straight-chain alkanoic acid as the material allowing an efficient production. Therefore, polyhydroxyalkanoate useful as a functional polymer having biodegradability can be expected application thereof to various fields such as a device material and a material for a medical treatment.

BRIEF DESCRIPTION OF THE DRAWINGS

FIG. 6 is an NMR spectrum of 5-(4-fluorophenoxy) valeric acid obtained in Example C-1.

FIG. 12 is a DNA sequence of a 16s rRNA coding region of *Pseudomonas jessenii* P161; FERM BP-7376.

DETAILED DESCRIPTION OF THE PREFERRED EMBODIMENTS

Figure 1:
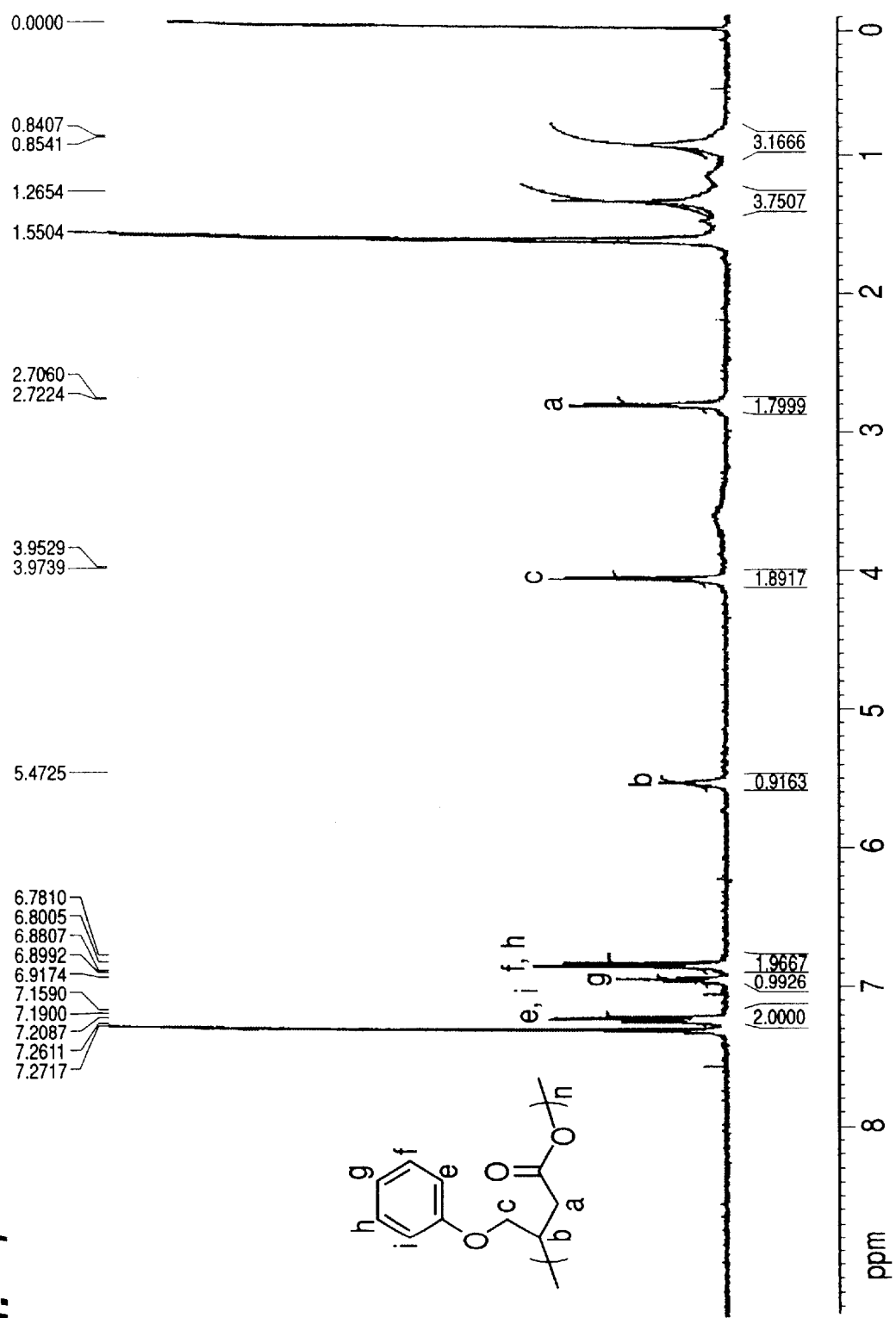
FIG. 1 is an $^1$H-NMR spectrum of PHA collected from the cultured cells of strain P91 in Example A-2.

The present invention relates to a novel polyhydroxyalkanoate (PHA) and a method of producing PHA.

The first embodiment in the method of producing PHA of the present invention is a production method characterized by incubating a microorganism in a medium containing yeast extract and an alkanoate of Formula (12)

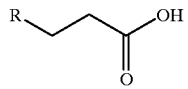

(12)

wherein R is at least one or more groups selected from group represented by any of the following general Formula (2), (3), or (4)), extracting a polyhydroxyalkanoate (PHA) from cells of the microorganism, and obtaining the PHA having a monomer unit of Formula (13),

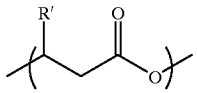

(13)

wherein R' is at least one or more groups selected from a group selected as R in Formula (12);

a group having the corresponding R1, wherein $q=q_0-2$, $q=q_0-4$, or $q=q_0-6$, provided that the group selected as R is of Formula (2), wherein $q=q_0$;

a group having the corresponding R2, wherein $r=r_0-2$, $r=r_0-4$, or $r=r_0-6$, provided that the group selected as R is of Formula (3), wherein $r=r_0$; and a group having the corresponding R3, wherein $s=s_0-2$, $s=s_0-4$, or $s=s_0-6$, provided that the group selected as R is of Formula (4), wherein $s=s_0$, provided that $q_0-2$, $r_0-2$, or $s_0-2$, $q_0-4$, $r_0-4$, or $s_0-4$, $q_0-6$, $r_0-6$, or $s_0-6$ can be only the integer of one or more),

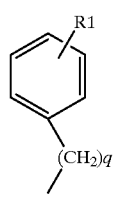

(2)

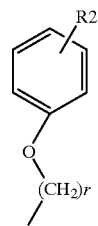

(3)

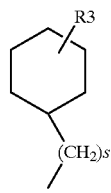

(4)

wherein R1 is a group selected from hydrogen atom (H), halogen atom, —CN, —NO$_2$, —CF$_3$, —C$_2$F$_5$, —C$_3$F$_7$, and q is selected from the integer of 1 to 8;

in Formula (3), R2 is a group selected from hydrogen atom (H), halogen atom, —CN, —NO$_2$, —CF$_3$, —C$_2$F$_5$, —C$_3$F$_7$, and r is selected from the integer of 1 to 8; and in Formula (4), R3 is a group selected from hydrogen atom (H), halogen atom, —CN, —NO$_2$, —CF$_3$, —C$_2$F$_5$, —C$_3$F$_7$, and s is selected from the integer of 1 to 8). In particular, it is the production method characterized by obtaining polyhydroxyalkanoate consisting of a monomer unit represented by the above general Formula (13).

In this method, PHA containing the corresponding monomer unit, as well as, in some cases, an accompanying secondary monomer unit having shorter carbon chain can be produced by using a single kind of alkanoate of Formula (12) as a raw material. As mentioned above, a plurality of alkanoates of Formula (12) can also be used as a raw material, and at that time, it is preferred to use an appropriate number of alkanoates, in consideration of function and property requisite for polymer to be produced. In general, the above aim can be expected to fully achieve by using up to about five different alkanoates of Formula (12) as a raw material. Furthermore, to finely control functions and properties, five or more of different raw materials can be utilized. For example, the total of more than five different raw materials can be used which consist of up to about three different alkanoates selected each from alkanoate group represented by the above general Formula (2), (3), and (4).

The substituent R1 on benzene ring in the general Formula (2) and the substituent R2 on benzene ring in the general Formula (3) can be selected from any of ortho-position (2- or 6-position), meta-position (3- or 5-position), or para-position (4-position). The resultant polyhydroxyalkanoate will contain a monomer unit having the corresponding substituted benzene ring. Which isomer is selected as a raw material is properly determined depending on intended functions and properties. When differences in the above functions and properties is not a critical problem, an alkanoate having substituent at para-position (4-position) on benzene ring can be more advantageously used similar to an unsubstituted alkanoate with respect to yield and readiness to be incorporated into polymer. Similarly, the location of substituent R3 on cyclohexyl ring of the general Formula (4) can be selected from any of 1-, 2- (or 6-), 3- (or 5-), and 4-position, and both cis- and trans-configuration can be selected. The resultant polyhydroxyalkanoate will contain monomer unit having the corresponding substituted cyclohexyl ring. Which isomer is selected as a raw material is properly determined depending on intended functions and properties. When differences in the above functions and properties is not a critical problem, an alkanoate having substituents at 4-position on cyclohexyl ring can be more advantageously used similar to an unsubstituted alkanoate with respect to yield and readiness to be incorporated into polymer. Polyhydroxyalkanoate produced by microorganisms, which has chiral center at 3-position carbon atom of monomer unit, is generally a polymer consisting only of R-body, that is, an isotactic polymer. As a result, PHA produced by the present method becomes a polymer having biodegradability.

According to the method of the present invention, microorganisms can be cultured by two steps comprising the initial culture in the medium containing alkanoate of Formula (12) and yeast extract, and subsequent culture in the medium containing the alkanoate and restricted nitrogen source. Microorganism can also be cultured in one step in the medium containing alkanoate of Formula (12) and yeast extract. Furthermore, the microorganism utilized is preferably selected from those belonging to Pseudomonas sp. As examples of advantageously available strains belonging to Pseudomonas sp., *Pseudomonas cichorii* YN2 (FERM BP-7375), *Pseudomonas cichorii* H45 (FERM BP-7374), *Pseudomonas putida* P91 (FERM BP-7373), and *Pseudomonas jessenii* P161 (FERM BP-7376) can be shown, and it is more preferred to select any of the above four strains.

These four strains have been deposited under the terms of the Budapest Treaty with the National Institute of Bioscience and Human Technology, Agency of Industrial Science and Technology, which is located at 1-3, Higashi 1-chome, Tsukaba-shi, Ibaraki-ken, 305 Japan.

The present inventors have succeeded in obtaining microorganism capable of producing poly-3-hydroxy-4-phenoxybutyric acid (PHPXB) homopolymer consisting of a monomer unit of 3-hydroxy-4-phenoxybutyric acid (3HPxB) of Formula (5):

(14)

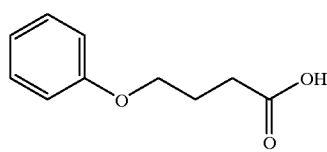

when cultured in a medium containing yeast extract and 4-phenoxybutyric acid (PxBA) of Formula (14).

(5)

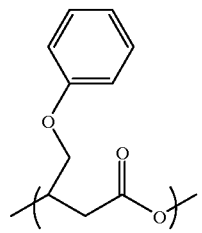

Thus, one mode included in the above first embodiment according to the method of producing polyhydroxyalkanoates of the present invention is a method characterized by having a process of incubating a microorganism capable of producing PHPxB homopolymer consisting of repeats units of 3HPxB monomer unit of Formula (5) by utilizing PxBA in the medium containing PxBA of Formula (14) and yeast extract.

There have been no reports of the production of polyhydroxyalkanoate containing a monomer unit of 3HPxB by microorganisms by using PxBA as a substrate, as well as the production of polyhydroxyalkanoate of PHPxB homopolymer by microorganisms. PHPxB obtained by the above method, therefore, is new, and is encompassed in the invention of novel polyhydroxyalkanoates, which the present invention provides.

The present inventors have also succeeded in obtaining microorganism capable of producing a homopolymer consisting of 3-hydroxy-5-phenoxyvaleric acid (3HPxV) monomer unit of Formula (6):

(15)

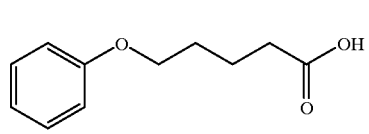

when cultured in a medium containing yeast extract and 5-phenoxyvaleric acid (PxVA) of Formula (15).

(6)

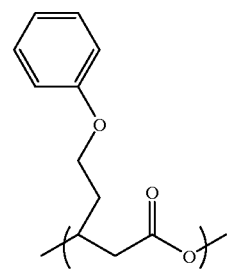

Thus, another one mode included in the above first embodiment is a method characterized by having a process of incubating a microorganism capable of producing poly-3-hydroxy-5-phenoxyvaleric acid (PHPxV) homopolymer consisting of repeats units of 3HPxV monomer unit of Formula (6) by utilizing PxVA in a medium containing PxVA of Formula (15) and yeast extract.

There have been no reports of the production of polyhydroxyalkanoates containing a monomer unit of 3HPxV by microorganisms by using PxVA as a substrate, as well as the production of polyhydroxyalkanoates of PHPxV homopolymer by microorganisms. PHPxV obtained by the above method, therefore, is new, and is encompassed in the invention of novel polyhydroxyalkanoates provided by the present invention.

The present inventors have also succeeded in obtaining microorganism capable of producing a homopolymer consisting of 3-hydroxy-5-(fluorophenoxy)valeric acid (3HFPxV) monomer unit of Formula (16):

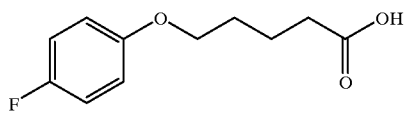

(17)

when cultured in the medium containing yeast extract and 5-(4-fluorophenoxy)valeric acid (FPxVA) of Formula (17).

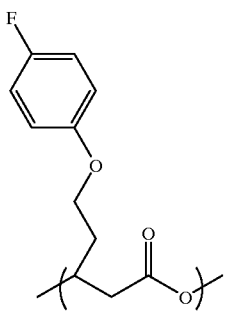

(16)

Thus, another mode included in the above first embodiment is a method characterized by having a process of incubating a microorganism capable of producing poly-3-hydroxy-5-(fluorophenoxy)valeric acid (PHFPxV) homopolymer consisting of repeats units of 3HFPxV monomer unit of Formula (16) by utilizing FPxVA in a medium containing FPxVA of Formula (17) and yeast extract.

The present inventors have also succeeded in obtaining microorganism capable of producing a copolymer consisting of 3-hydroxy-5-phenoxyvaleric acid (3HPxV) and 3-hydroxy-7-phenoxyheptanoic acid (3HPxHp) of Formula (6) and (22), respectively:

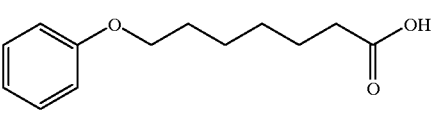

(23)

when cultured in a medium containing yeast extract 7-phenoxyheptanoic acid (PxHpA) of Formula (23).

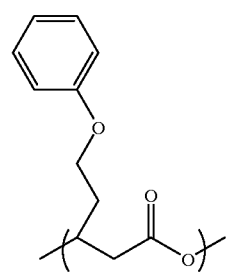

(6)

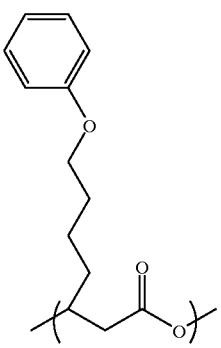

(22)

Thus, another mode included in the above first embodiment is a method characterized by having a process to culture a microorganism capable of producing a polyhydroxyalkanoate copolymer consisting of 3HPxV and 3HPxHp monomer units of Formula (6) and (22), respectively, by utilizing PxHpA in the medium containing PxHpA of Formula (23) and yeast extract.

The present inventors have also succeeded in obtaining a microorganism capable of producing a copolymer consisting of 3-hydroxy-4-phenoxybutyric acid (3HPxB), 3-hydroxy-6-phenoxyhexanoic acid (3HPxHx), and 3-hydroxy-8-phenoxyoctanoic acid (3HPxO) of Formula (5), (24), and (25), respectively:

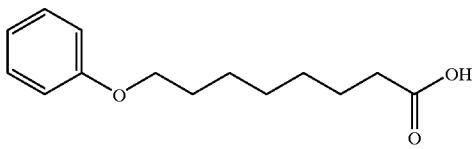

(26)

when cultured in a medium containing yeast extract and 8-phenoxyoctanoic acid (PxOA) of Formula (26).

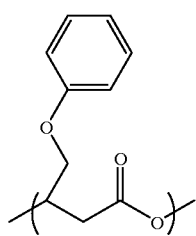

(5)

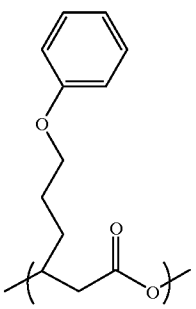

(24)

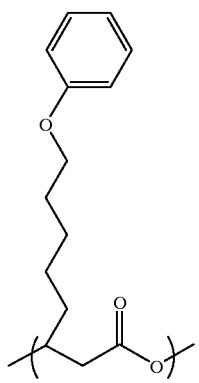

(25)

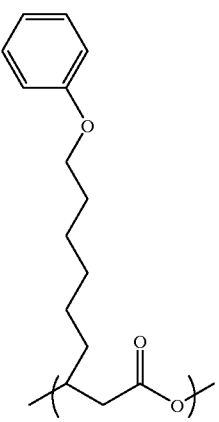

(27)

Thus, another mode included in the above first embodiment is the method characterized by having a process of incubating a microorganism capable of producing a polyhydroxyalkanoate copolymer consisting of 3HPxB, 3HPxHx, and 3HPxO monomer units of Formula (5), (24), and (25), respectively, by utilizing PxOA in the medium containing PxOA of Formula (26) and yeast extract.

A microorganism capable of producing a copolymer consisting of 3-hydroxy-5-phenoxy valeric acid (3HPxV), 3-hydroxy-7-phenoxy heptanoic acid (3HPxHp), and 3-hydroxy-9-phenoxy nonanoic acid (3HPxN) units, which are expressed by Formula, was successfully obtained.

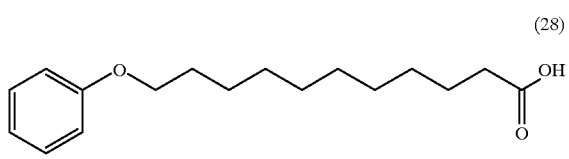

(28)

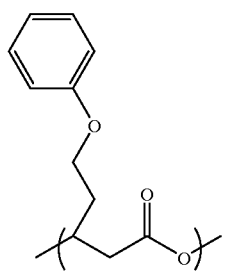

(6)

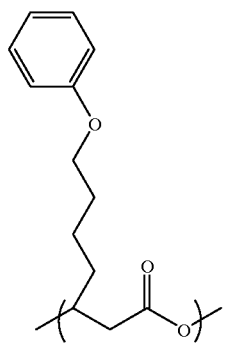

(22)

One more mode included in the above described first embodiment is a method having a step of culturing of microorganisms to produce a polyhydroxyalkanoate copolymer consisting of 3HPxV, 3HPxHp, and 3HPxN monomer units expressed by the above described Formulae (6), (22), and (27) using PxUDA in a culture medium containing PxUDA expressed by the above described Formula (28) and yeast extract.

Furthermore, in addition to the methods described in the above described series of specific forms in detail, by using an alkanoate, of Formula (12), in which a side chain having a phenoxy group is replaced with a desired group as a material of the monomer component, PHA having various corresponding side chains can be selectively produced using microorganisms. A production method for polyhydroxyalkanoate using alkanoate of Formula (12) as the material and having the monomer unit composition shown by Formula (13) is also included in the above described first embodiment by the production method for polyhydroxyalkanoate of the present invention.

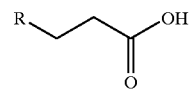

(12)

(R is at least one or more groups selected from groups expressed by Formula (3));

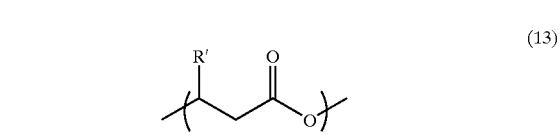

(13)

(R' is the group selected in the above described Formula (12) as R)

and in the case where expressed by the following Formula (3) and is the group of $r=r_0$, the group selected as the R has a corresponding R2 and at least one or more group selected from groups of $r=r_0-2$, $q=r_0-4$, or $r=r_0-6$.)

$r_0$–2, $r_0$–4, or $r_0$–6 can be an integer value of 1 or more;

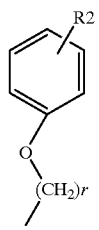
(3)

(R2 is the group selected from a hydrogen atom (H), halogen atom, —CN, —NO$_2$, —CF$_3$, —C$_2$F$_5$, and —C$_3$F$_7$ and r is selected from integers of 1 to 8.)

In many cases, when PHA is produced by containing one kind of alkanoate expressed by Formula (12) as the material and a corresponding monomner unit, in some cases, a by-produced monomer unit of which carbon chain accompanied is reduced. On the other hand, as described above, for alkanoate as the material expressed by Formula (12), a plurality of kinds can be used for culture. In consideration of a function and a physical property necessary for a polymer produced, it is preferable to use a proper number of kinds. In general, by using 3 kinds, in maximum, of alkanoate expressed by Formula (12) as the material, it is expected that the above described purpose can be sufficiently achieved. In addition, in the purpose to control finely functionality and the physical property, many kinds of materials more than three can be used.

For the material, any one of a substitution position of R2 on a benzene ring Formula (3) can be selected from an ortho position (position 2 or position 6), meta position (position 3 or position 5), or para position (position 4). Polyhydroxyalkanoate yielded is that containing the monomer unit having a corresponding substituted phenoxy group. An isomer to be selected as the material is determined appropriately according to objective functionality and physical property. In the case where a difference in the above described functionality and physical property are not become the problem, normally, that having the substitution group in the para position (position 4) on the benzene ring can be more preferably used, in a point of yield or easy uptake into the polymer, comparably to that not substituted. In polyhydroxyalkanoate produced by such microorganisms, a carbon atom of the position 3 of the monomer unit has the chiral in a center and in general, is the polymer consisting of only R-body and hence, isotactic polymer. Consequently, PHA produced by such method is the polymer having biodegradability.

In addition, the inventors successfully obtained the microorganism capable of producing a homopolymer consisting of 3-hydroxy-5-phenylvaleric acid (3HPV) monomer unit expressed by Formula (9), when cultured in a culture medium containing 5-phenylvaleric acid (PVA), expressed by Formula (18), and yeast extract.

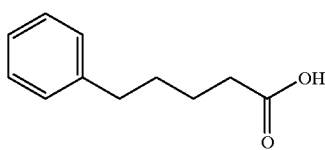
(18)

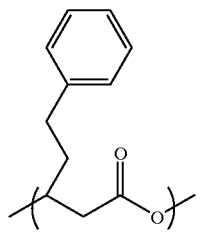
(9)

In other words, an alternative mode included in the above described first embodiment is a method characterized by having a step of culturing a microorganism which can produce a poly-3-hydroxy-5-phenylvaleric acid (PHPV) homopolymer consisting of repeated units of 3HPV monomer units expressed by the above described Formula (9), using PVA in a culture medium containing PVA of Formula (18) and yeast extract.

The inventors also successfully obtained the microorganism capable of producing the homopolymer consisting of 3-hydroxy-5-(4-fluorophenyl) valeric acid (3HFPV) monomer unit expressed by Formula (7) when cultured in a culture medium containing 5-(4-fluorophenyl) valeric acid (FPVA) of Formula (19), and yeast extract.

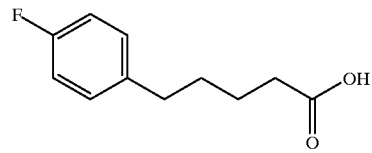
(19)

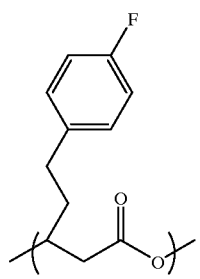
(7)

In other words, an alternative mode included in the above described first embodiment is a method characterized by having a step of cultivation of a microorganism which can produce a poly-3-hydroxy-5-(4-fluorophenyl) valeric acid (PHFPV) homopolymer consisting of repeated units of 3HFPV monomer units of Formula (7), using FPVA in a culture medium containing FPVA of Formula (19) and yeast extract.

So far, there is no report about production of polyhydroxyalkanoate, in which 3HFPV as the monomer unit, using FPVA as a substrate by microorganisms. Also, there is no report about production of polyhydroxyalkanoate being the homopolymer of PHFPV by microorganisms. Consequently, PHFPV yielded by the above described method is a new product and included in the invention a new polyhydroxyalkanoate provided by the present invention.

The inventors also successfully obtained the microorganism capable of producing the copolymer consisting of 3-hydroxy-4-phenylbutyric acid (3HPB) and 3-hydroxy-6-phenylhexanoic acid (3HPHx) units expressed by Formulas

(10) and (11) when cultured in a culture medium containing 6-phenylhexanoic acid (PHxA), expressed by Formula (21), and yeast extract,

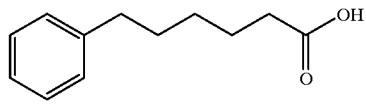
(21)

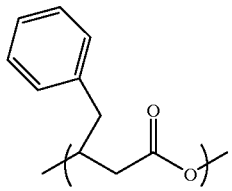
(10)

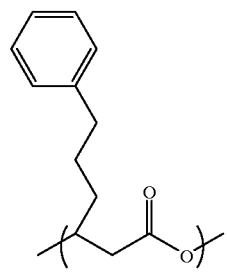
(11)

In other words, an alternative mode included in the above described first embodiment is a method characterized by having a step of cultivation of a microorganism to produce a polyhydroxyalkanoate copolymer consisting of 3HPB and 3HPHx monomer units expressed by the above described Formula (10) and (11), using PHxA in a culture medium containing PHxA, expressed by the above described Formula (21), and the yeast extract.

So far, there is no report about production of polyhydroxyalkanoate containing 3HPB and 3HPHx monomer units, using PHxA as a substrate by microorganisms. Also, there is no report about production of polyhydroxyalkanoate consisting of 3HPB and 3HPHx monomer units by microorganisms. Consequently, polyhydroxyalkanoate consisting of 3HPB and 3HPHx monomer units and yielded by the above described method is a new product and included in the invention a new polyhydroxyalkanoate provided by the present invention.

Furthermore, in addition to method described in the above described series of specific forms in detail, by using an alkanoate, of Formula (12), in which a side chain having a phenyl group is substituted to a desired group as a material of the monomer component, PHA having various corresponding side chains can be selectively produced using microorganisms. A production method for polyhydroxyalkanoate using alkanoate of Formula (12) as the material and having the monomer unit composition shown by Formula (13) is also included in the above described first embodiment by the production method for polyhydroxyalkanoate of the present invention.

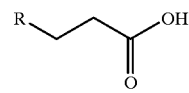
(12)

(In Formula (12), R is at least one or more groups selected from groups expressed by the following general Formula (2).)

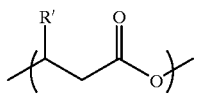
(13)

(In Formula (13), R' is the group selected as R in the above described Formula (12), and if the group selected as R is expressed by Formula (2) and is the group of $q=q_0$, has the corresponding R1 and at least one or more group selected from $q=q_0-2$, $q=q_0-4$, or $q=q_0-6$. $q_0-2$, $q_0-4$, or $q_0-6$ can be the integer value of 1 or more.)

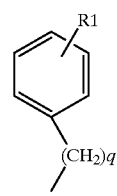
(2)

(Of Formula (2), the R1 is the group selected from the hydrogen atom (H), halogen atom, —CN, —NO$_2$, —CF$_3$, —C$_2$F$_5$, and —C$_3$F$_7$ and q is selected from integers of 1 to 8.)

In many cases, when PHA is produced by containing one kind of alkanoate expressed by Formula (12) as the material and the corresponding monomer unit, in some cases, the by-product monomer unit of which carbon chain accompanied is reduced. On the other hand, as described above, for alkanoate as the material expressed by Formula (12), the plurality of kinds can be used for culture. In consideration of the function and the physical property necessary for the polymer produced, it is preferable to use the proper number of kinds. In general, by using 3 kinds, in maximum, of alkanoate expressed by Formula (12) as the material, it is expected that the above described purpose can be sufficiently achieved. In addition, in the purpose to control finely the functionality and the physical property, many kinds of materials more than three can be used.

For the material, any one of the substitution position of R1 on the benzene ring of Formula (2) can be selected from the ortho position (position 2 or position 6), meta position (position 3 or position 5), or para position (position 4). Polyhydroxyalkanoate yielded is that containing the monomer unit having the corresponding substituted phenyl group. The isomer to be selected as the material is determined appropriately according to objective functionality and physical property. In the case where the difference in the above described functionality and physical property does not become the problem, normally, that having the substitution group in the para position (position 4) on the benzene ring can be more preferably used, in the point of yield or easy uptake into the polymer, comparably to that not substituted. In polyhydroxyalkanoate produced by such microorganisms, the carbon atom of the position 3 of the monomer unit has the chiral in the center and in general, is the polymer consisting of only R-body and hence, the isotactic polymer. Consequently, PHA produced by such method is the polymer having biodegradability.

In addition, the inventors found that when by using 4-cyclohexyl butyric acid (CHBA) as the substrate, microorganisms are cultured in the culture medium containing CHBA and yeast extract to produce polyhydroxyalkanoate to accumulate in cells; the monomer unit of polyhydroxyalkanoate contains 3-hydroxy-4-cyclohexyl butyric acid (3HCHB) in the high ratio and showed the sufficiently high yield and for polyhydroxyalkanoate containing 3HCHB yielded, found that the PHCHB homopolymer consisting of the repeated unit of 3HCHB monomer units can be separated by carrying out purification treatment.

In other words, an alternative mode included in the above described first embodiment is the method of producing poly-3-hydroxy-4-cyclohexyl butyric acid (PHCHB) consisting of 3HCHB monomer units and

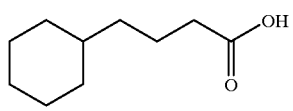

(20)

the method of producing PHCHB homopolymer consisting of 3HCHB monomer units expressed by Formula (8) and characterized by having the step of cultivation of microorganisms in the culture medium containing CHBA expressed by Formula (20) and the yeast extract.

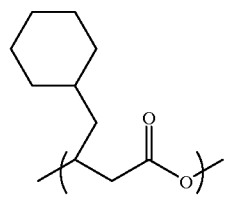

(8)

So far, there is no report about production of polyhydroxyalkanoate being the homopolymer of PHCHB by microorganisms. Consequently, PHCHB yielded by the above described method is a new product and included in the invention of a new polyhydroxyalkanoate provided by the present invention.

Furthermore, in addition to method described in the above described series of specific forms in detail, by using an alkanoate, of Formula (12), in which a side chain having a cyclohexyl group is substituted to the desired group as a material of the monomer component, PHA having various corresponding side chains can be selectively produced using microorganisms. A production method for polyhydroxyalkanoate using alkanoate of Formula (12) as the material and having the monomer unit composition shown by Formula (13) is also included in the above described first embodiment by the production method for polyhydroxyalkanoate of the present invention.

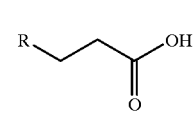

(12)

(In Formula (12), R is at least one or more groups selected from groups expressed by the following general Formula (4).)

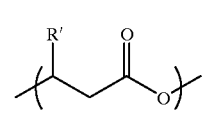

(13)

(In Formula (13), R' is the group selected as R in the above described Formula (12), and if the group selected as R is expressed by Formula (4) and is the group of $s=s_0$, it has the corresponding R3 and at least one or more group selected from $s=s_0-2$, $s=s_0-4$, or $s=s_0-6$. $s_0-2$, $s_0-4$, or $s_0-6$ can be the integer value of 1 or more.)

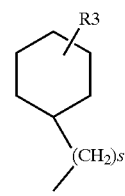

(4)

(Of Formula (4), the R3 is the group selected from the hydrogen atom (H), halogen atom, —CN, —NO$_2$, —CF$_3$, —C$_2$F$_5$, and —C$_3$F$_7$ and s is selected from integers of 1 to 8.)

In many cases, when PHA is produced by containing one kind of alkanoate expressed by Formula (12) as the material and the corresponding monomer unit, in some cases, the by-produced monomer unit of which carbon chain accompanied is reduced. On the other hand, as described above, for alkanoate as the material expressed by Formula (12), the plurality of kinds can be used for culture. In consideration of the function and the physical property necessary for the polymer produced, it is preferable to use the proper number of kinds. In general, by using 3 kinds, in maximum, of alkanoate expressed by Formula (12) as the material, it is expected that the above described purpose can be sufficiently achieved. In addition, in the purpose to control finely the functionality and the physical property, many kinds of materials more than three can be used.

For the material, any one of the substitution positions of R3 on the cyclohexyl ring of Formula (4) can be selected from position 1, position 2 (or position 6), position 3 (or position 5), and position 4. In addition, either cis configuration or trans configuration can be selected. Polyhydroxyalkanoate yielded is that containing the monomer unit having the corresponding substituted cyclohexyl ring. The isomer to be selected as the material is determined appropriately according to objective functionality and physical property. In the case where the difference in the above described functionality and physical property does not become the problem, normally, that having the substitution group in the 4 on the cyclohexyl ring can be more preferably used, in the point of yield or easy uptake into the polymer, comparably to that not substituted. In polyhydroxyalkanoate produced by such microorganisms, the carbon atom of the position 3 of the monomer unit has the chiral in the center and in general, is the polymer consisting of only R-body and hence, the isotactic polymer. Consequently, PHA produced by such method is the polymer having biodegradability.

In addition, the inventors successfully obtained a microorganism capable of producing copolymer consisting of 3-hydroxy-5-phenoxy valeric acid (3HPxV) monomer unit expressed by Formula (6) and 3-hydroxy-5-phenyl valeric acid (HPV) monomer unit expressed by Formula (9) when cultured in the culture medium containing yeast extract and 5-phenoxy valeric acid (PxVA) expressed by Formula (15),

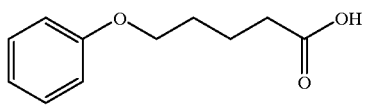

(15)

and
5-phenyl valeric acid (PVA) expressed by Formula (18).

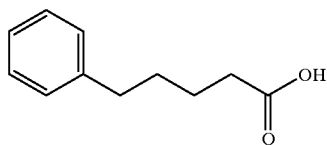

(18)

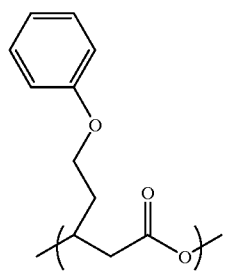

(6)

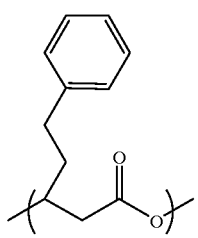

(9)

In other words, an alternative mode included in the above described first embodiment is the method of producing a poly-(3-hydroxy-5-phenoxy valeric acid/3-hydroxy-5-phenyl valeric acid) copolymer consisting of repeated units of the 3HPxV monomer unit and the 3HPV monomer units expressed by the above described Formula (6) and (9), using PxVA and PVA and characterized by having the step of cultivation of microorganisms in the culture medium containing PxVA and PVA expressed by the above described Formula (15), (18), and the yeast extract.

So far, there is no report about production of polyhydroxyalkanoate containing 3HPxV and 3HPV monomer units, using PxVA and PVA as a substrate by microorganisms. Also, there is no report about production of polyhydroxyalkanoate consisting of 3HPxV and 3HPV monomer units by microorganisms. Consequently, polyhydroxyalkanoate consisting of 3HPxV and 3HPV monomer units and yielded by the above described method is a new product and included in the invention the new polyhydroxyalkanoate provided by the present invention.

Furthermore, in addition to method described in the above described specific forms in detail, by using a plurality of kinds of alkanoate, as the material, selected from the following alkanoate of Formula (12), polyhydroxyalkanoate containing a plurality of kinds of monomer units having various corresponding side chains can be selectively produced using microorganisms. In other words, the first embodiment of the production method for polyhydroxyalkanoate of the present invention includes the specific form of production method for polyhydroxyalkanoate containing a plurality of kinds of monomer units having various corresponding side chains by using a plurality of kinds of alkanoate of as the material.

In other words, the production method is characterized in that a microorganism is cultured in a culture medium containing yeast extract and the alkanoate expressed by Formula (12):

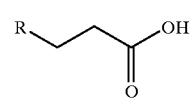

(12)

(In Formula (12), R is at least one or more group selected from groups expressed by any one of the following general Formula (2), general Formula (3), or general Formula (4)), and the microorganism is extracted to obtain polyhydroxyalkanoate expressed by Formula (13) having at least one of the monomer units represented by Formula (13):

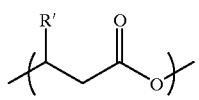

(13)

(In Formula (13), R' is the group selected as R in the above described Formula (12), and at least one or more groups selected from the groups having the corresponding R1 and being $q=q_0-2$, $q=q_0-4$, or $q=q_0-6$, if the group selected as R is expressed by Formula (2) and is the group of $q=q_0$, having the corresponding R2 and being $r=r_0-2$, $r=r_0-4$, or $r=r_0-6$, if the group selected as R is expressed by Formula (3) and is the group of $r=r_0$, and having the corresponding R3 and being $s=s_0-2$, $s=s_0-4$, or $s=s_0-6$, if the group selected as R is expressed by Formula (4) and is the group of $s=s_0$.

$q_0-2$, $r_0-2$, or $s_0-2$, or $q_0-4$, $r_0-4$, or $s_0-4$, or $q_0-6$, $r_0-6$, or $s_0-6$, can be the integer value of 1 or more.)

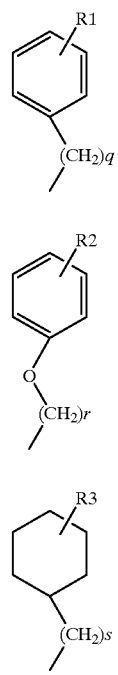

(2)

(3)

(4)

(Of Formula (2), the R1 is the group selected from the hydrogen atom (H), halogen atom, —CN, —$NO_2$, —$CF_3$, —$C_2F_5$, and —$C_3F_7$ and q is selected from integers of 1 to 8; of Formula (3) the R2 is the group selected from the hydrogen atom (H), halogen atom, —CN, —$NO_2$, —$CF_3$, —$C_2F_5$, and —$C_3F_7$ and r is selected from integers of 1 to 8; of Formula (4) the R3 is the group selected from the hydrogen atom (H), halogen atom, —CN, —$NO_2$, —$CF_3$, —$C_2F_5$, and —$C_3F_7$ and s is selected from integers of 1 to 8.) Specifically, the production method is characterized in obtaining polyhydroxyalkanoate consisting of monomer units holding side chains corresponding to at least one alkanoate as the material. In other words, the production method for polyhydroxyalkanoate having monomer units characterized by having at least one or more side chain structure, in which side chain structure of monomer units corresponds to each alkanoate, particularly, consisting of each monomer units derived from each alkanoate, is that in which a plurality of kinds of alkanoate is used as the material, as monomer units, which can be taken in polyhydroxyalkanoate, according to a plurality of kinds of alkanoate expressed by Formula (12) selected.

In this method, by using one kind of the alkanoate as the material expressed by Formula (12), PHA containing the corresponding monomer unit and in some cases, the by-produced monomer unit of, which carbon chain accompanied is reduced, can produced. On the other hand, as described above, for the alkanoate as the material expressed by Formula (12), the plurality of kinds can be used for culture. In consideration of the function and the physical property necessary for the polymer produced, it is preferable to use the proper number of kinds. In general, by using about 5 kinds, in maximum, of alkanoate expressed by Formula (12) as the material, it is expected that the above described purpose can be sufficiently achieved. In addition, in the purpose to control finely the functionality and the physical property, many kinds of materials more than five can be used. For example, it is possible to contain all three of the above described general Formula (2), general Formula (3), or general Formula (4), select three about kinds in maximum, and sum them to use more than 5 kinds of materials.

The substitution group R1 on the benzene ring in the general Formula (2) and the substitution group R2 on the benzene ring in the general Formula (3) can be selected from any one of the ortho position (position 2 or position 6), meta position (position 3 or position 5), and para position (position 4). Polyhydroxyalkanoate yielded is that containing the monomer unit having a corresponding substituted benzene ring. An isomer to be selected as the material is determined appropriately according to objective functionality and physical property. In the case where a difference in the above described functionality and physical property are not become the problem, normally, that having the substitution group in the para position (position 4) on the benzene ring can be more preferably used, in the point of yield or easy uptake into the polymer, comparably to that not substituted. Similarly, the substitution group R3 on the cyclohexyl ring in the general Formula (4) can be selected from any one of the position 1, position 2 (or position 6), position 3 (or position 5), and position 4. In addition, either cis configuration or trans configuration can be selected. Polyhydroxyalkanoate yielded is that containing the monomer unit having the corresponding substituted cyclohexyl ring. The isomer to be selected as the material is determined appropriately according to objective functionality and physical property. In the case where a difference in the above described functionality and physical property are not become the problem, normally, that having the substitution group in the position 4 on the cyclohexyl ring can be more preferably used, in the point of yield or easy uptake into the polymer, comparably to that not substituted. In polyhydroxyalkanoate produced by such microorganisms, the carbon atom of the position 3 of the monomer unit has the chiral in a center and in general, is the polymer consisting of only R-body and hence, isotactic polymer. Consequently, PHA produced by such method is the polymer having biodegradability.

As described in detail showing representative specific forms in the production method for polyhydroxyalkanoate of the present invention, polyhydroxyalkanoate having various corresponding side chains as the monomer components can be selectively produced by using microorganisms by using a derivative, which was made by substituting the side chain of alkanoate by the desired group, as the material and therefore, the present invention also provides an invention of polyhydroxyalkanoate, obtained by such method, having a monomer composition expressed by the following general Formula (1). In other words, a new polyhydroxyalkanoate according to the present invention is polyhydroxyalkanoate consisting of monomer units expressed by Formula (1).

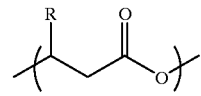

(1)

(In Formula (1), R is at least one or more group selected from groups expressed by any one of the following general Formula (2), general Formula (3), or general Formula (4)).

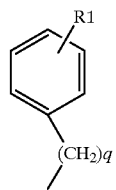

(2)

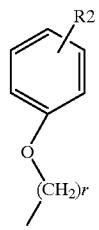

(3)

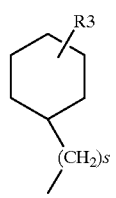

(4)

(Of Formula (2), R1 is the group selected from the hydrogen atom (H), halogen atom, —CN, —NO$_2$, —CF$_3$, —C$_2$F$_5$, and —C$_3$F$_7$ and q is selected from integers of 1 to 8; of Formula (3), the R2 is the group selected from the hydrogen atom (H), halogen atom, —CN, —NO$_2$, —CF$_3$, —C$_2$F$_5$, and —C$_3$F$_7$ and r is selected from integers of 1 to 8; of Formula (4) the R3 is the group selected from the hydrogen atom (H), halogen atom, —CN, —NO$_2$, —CF$_3$, —C$_2$F$_5$, and —C$_3$F$_7$ and s is selected from integers of 1 to 8.

Here, as R in the above described general Formula (1), if one kind of group is selected, in Formula (2), the group of q=2 in R1=H and the group of q=3 in R1=H in Formula (3), the group of r=2 in R2=halogen atom, the group of r=3 in R2=—CN, and the group of r=3 in R2=—NO$_2$ is eliminated from alternatives, if two kind of group is selected, in Formula (2), a combination of two groups of q=3 and 5 in R1=H, in Formula (3), the combination of two groups of r=1 and 3 in R2=H, the combination of two groups of r=2 and 4 in R2=H, the combination of two groups of r=2 and 6 in R2=H, and the combination of two groups of r=2 and 4 in R2=halogen atom is eliminated from alternatives, if three kind of group is selected, in Formula (2), the combination of three groups of q=3, 5, and 7 in R1=H, in Formula (3), the combination of three groups of r=1, 3, and 5 in R2=H and the combination of three groups of r=2, 4, and 6 in R2=H is eliminated from alternatives.)

Polyhydroxyalkanoate of the present invention, as described above, can contain one kind of monomer unit expressed by the general Formula (1) and also contain a plurality of kinds. In consideration of a function and a physical property necessary for the objective polymer, it is preferable to use a proper number of kinds of monomer units. In general, by selecting 10 kinds of monomer units, in total, expressed by Formula (1), it is expected that the above described purpose can be sufficiently achieved. In addition, in the purpose to control finely functionality and the physical property, many kinds of monomer units more than 10 can be contained in configuration.

For example, when polyhydroxyalkanoate is produced by containing a plurality of kinds of monomer units expressed by such general Formula (1), in addition to monomer units corresponding to alkanoate as the material, in some cases, a by-produced monomer unit of which carbon chain accompanied is reduced. Therefore, the present invention include that in which even if alkanoate itself is about 5 kinds as the material, each yields monomer unit of two kinds or more including the by-produced monomer unit and as the results, PHA contains monomer units of 10 kinds or more in total. In addition, for example, the present invention include that in which contains all of three kinds of the above described general Formula (2), general Formula (3), and general Formula (4), of which about 3 kinds in maximum are selected each, and becomes about 10 kinds of alkanoate as the material in total to yield PHA containing monomer units of 10 kinds or more containing a little numbers of the by-produced monomer unit.

Any one of the substitution position of R1 on a benzene ring Formula (2) and the substitution position of R2 on a benzene ring Formula (3) can be selected from the ortho position (position 2 or position 6), meta position (position 3 or position 5), and para position (position 4). Polyhydroxyalkanoate yielded is that containing the monomer unit having a corresponding substituted benzene group. An isomer to be selected as the material is determined appropriately according to objective functionality and physical property. In the case where a difference in the above described functionality and physical property are not become the problem, normally, that having the substitution group in the para position (position 4) on the benzene ring can be more preferably used, in a point of yield or easy uptake into the polymer, comparably to that not substituted. Similarly, for the substitution position of R3 on the cyclohexyl ring of the general Formula (4), any one of position 1, position 2, (or, position 6), position 3 (or, position 5), and position 4 can be selected and in addition, either cis configuration or trans configuration can be selected. In polyhydroxyalkanoate produced is that containing the monomer unit having the corresponding substituted cyclohexyl ring. The isomer to be selected is determined appropriately according to objective functionality and physical property. In the case where a difference in the above described functionality and physical property are not become the problem, normally, that having the substitution group in the position 4 on the cyclohexyl ring can be more preferably used, in a point of yield or easy uptake into the polymer, comparably to that not substituted. In polyhydroxyalkanoate produced by such microorganisms, the carbon atom of the position 3 of the monomer unit has the chiral in a center and in general, is the polymer consisting of only R-body and hence, isotactic polymer. Consequently, PHA producible by such method using microorganisms is the polymer having biodegradability.

The production method for PHA of the present invention is characterized in that in cultivation of microorganisms, by adding the yeast extract to alkanoate of Formula (12) as the material in the culture medium, content ratio of the objective monomer unit in PHA is increased very high or PHA consists of the objective monomer unit only in PHA produced by microorganisms to accumulate. An effect to enhance prioritization of a specified monomer unit is realized by adding only yeast extract to the culture medium as a carbon source other than alkanoate used as the material of PHA.

As an example of use of the yeast extract in the culture medium in production of PHA by microorganisms, the method described on the Japanese Patent Application Laid-Open No.5-49487 and using microorganisms belonging to the genus Rhodobacter is exemplified. However, this conventional method is the method for production of common PHB and PHV by using hydroxyalkanoic acid having no substitution group as the monomer unit. It has been known that a biosynthetic path of the objective PHA of the present invention is an independent path from the biosynthetic path to produce PHB and PHV. In the Japanese Patent Application Laid-Open No. 5-49487, there is no mention about the effect of the yeast extract in the PHA biosynthetic path of the object of the present invention. In addition, it has been evidently described about the effect of the yeast extract that for PHB and PHV commonly produced by microorganisms, addition of the yeast extract shows the effect to increase in PHA accumulation simply in cells and the yeast extract is not added for cell proliferation. The present invention carries out production and accumulation of PHA as well as proliferation by coexistence of alkanoate of Formula (12) with the yeast extract and thus, the yeast extract expresses a quite different effect. In addition, prioritization, being the effect of the present invention, of the specified monomer unit was never mentioned and therefore, in the composition of PHA produced by microorganisms, the effect, found in the present invention, of prioritization of the specified monomer unit having phenoxy group, phenyl group, and cyclohexyl group as the substitution group was not shown.

As an example using the yeast extract for PHA production by microorganisms, the method, described on the above described Japanese Patent No. 2989175, using *Pseudomonas putida* is exemplified. The production method for PHA disclosed in this patent uses the two-step cultivation and it is disclosed that PHA accumulation is carried out in only the cultivation of a second step under limitation of a nutrient source other than carbon source. In this point, this method quite differs in configuration and effect from the method of the present invention, in which cultivation is one step only in the culture medium containing alkanoate of Formula (12) and the yeast extract to perform biosynthesis and accumulation of the desired PHA. The effect of the yeast extract in Japanese Patent No. 2989175 simply aims proliferation of microorganisms used for cultivation of the second step in the first step cultivation in using the two-step cultivation and it has been evidently described that the first step cultivation is carried out under a nutrient rich condition. Here, the substrate of PHA does not coexist with the first step cultivation. The effect of the yeast extract in the two-step cultivation of the present invention is that doing production and accumulation of PHA as well as cell proliferation in the first step cultivation by coexisting of alkanoate of Formula (12) and the yeast extract in the first step cultivation, and the effect expressed by the yeast extract in the first step cultivation is quite different. In addition, in Japanese Patent No. 2989175, any one of citric acid, octanoic acid, nonanoic acid coexists as the carbon source in the first step cultivation and hence, it also differs in configuration from the present invention, in which alkanoate of Formula (12) and the yeast extract coexist.

As an example of a report of a microorganism, which can produce PHA, containing 3HPxB in the present invention as the monomer unit, to accumulated in the cell, there is the method using *Pseudomonas oleovorans* described on Macromolecules 29, 3432–3435, 1996. However, the method using *Pseudomonas oleovorans* uses only 8-phenoxyoctanoic (PxOA) as the substrate and therefore, it has an essential difference in which it cannot produce acetyl-Co A by β-oxidation, for example, of the present invention and it quite differs from the method using PxBA as the substrate together with the yeast extract. For PHA biosynthesized, the copolymer, which consists of three kinds of monomers of 3-hydroxy-8-phenoxy octanoic acid derived from PxOA as the substrate, 3-hydroxy-6-phenoxy hexanoic acid being the by-product derived from a metabolite, and 3HPxB, is produced. In contrast, in the present invention, use of the yeast extract allows production of PHA containing only 3HPxB derived from PxBA as the monomer unit containing the phenoxy group. PHA itself to be produced differs clearly between the above described reported and the present invention. In addition, there is no report of the production of PHA, containing 3HPxB as the monomer unit, by microorganisms using PxBA as the substrate. In addition, there is no report of the production of PHA, containing only 3HPxB as the monomer unit containing the phenoxy group, by microorganisms using PxBA as the substrate.

The production method of the present invention will be described below in detail.

Microorganisms used for the present invention may be any microorganisms, which is microorganisms capable of production of PHA from the alkanoate to accumulate using the alkanoate of Formula (12) as the substrate. According to the inventors' study, bacteria of Pseudomonas is good and among them, we found that *Pseudomonas cichorii* YN2, FERM BP-7375; *Pseudomonas cichorii* H45, FERM BP-7374; *Pseudomonas putida* P91, FERM BP-7373; and *Pseudomonas jessenii* P161 FERM BP-7376 are preferable microorganisms. Also using cells other than these strains, by cultivation using the alkanoate as the substrate, by carrying out screening of bacteria belonging to, for example, the genus Pseudomonas, microorganisms usable for the production method for PHA, of the present invention, can be obtained. For example, as bacteria belonging to the genus Pseudomonas, using *Pseudomonas oleovorans* is possible. In addition to microorganisms belonging to the genus Pseudomonas, use of microorganisms, which belongs to the genera Aeromonas, Comamonas, and Burkholderia and, by using the alkanoate as the material (substrate), produce PHA containing corresponding 3-hydroxyalkanoate as the monomer unit, is possible. However, in consideration of productivity, the above described 4 strains can be recommended as the most preferable strains.

The details of strains YN2, H45, P91, and P161 will be listed below.

<Bacteriological Properties of Strain YN2>

Cultivation temp.: 30° C.

Morphology:
    Cell form: rod, 0.8 μm×(1.5 to 2.0) μm
    Gram staining: negative
    Spore formation: negative
    Mobility: motile
    Form of colony: circular, entire smooth margin, low convex, smooth surface, glossy, translucent Physiological properties:
    Catalase: positive
    Oxidase: positive
    O/F test: non-fermentable
    Nitrate reduction: negative Indole production: positive
Glucose acidification: negative
Arginine dihydrolase: negative
Urease: negative
Esculin hydrolysis: negative
Gelatin hydrolysis: negative
β-galactosidase: negative
Substrate assimilation:
   Glucose: positive
   L-arabinose: positive
   D-mannose: negative
   D-mannitol: negative
   N-acetyl-D-glucosamine: negative
   Maltose: negative
   Potassium gluconate: positive
   n-capric acid: positive
   Adipic acid: negative
   dl-malic acid: positive
   Sodium citrate: positive
   Phenyl acetate: positive
Production of fluorescence on King's B agar: positive
Growth in 4% NaCl: positive (weak)
Accumulation of poly-β-hydroxy butyric acid: negative (determined by staining with Sudan Black a colony grown on a nutrient agar)
Hydrolysis of Tween 80: positive <Bacteriological Properties of Strain H45>
Morphological characteristics:
   Cell shape and size: rod, 0.8 μm×(1.0 to 1.2) μm
   Cell polymorphism: absent
   Mobility: positive
   Spore formation: negative
   Gram staining: negative
   Form of colony: circular, entire margin smooth, low convex, smooth surface, glossy, and cream color
Physiological properties:
   Catalase: positive
   Oxidase: positive
   O/F test: oxidative
   Nitrate reduction: negative
   Indole production: negative
   Glucose acidification: negative
   Arginine dihydrolase: negative
   Urease: negative
   Esculin hydrolysis: negative
   Gelatin hydrolysis: negative
   β-galactosidase: negative
   Production of fluorescence on King's B agar: positive:
   Growth in 4% NaCl: negative
   Accumulation of poly-β-hydroxy butyric acid: negative
Substrate assimilation:
   Glucose: positive
   L-arabinose: negative
   D-mannose: positive
   D-mannitol: positive
   N-acetyl-D-glucosamine: positive
   Maltose: negative
   Potassium gluconate: positive
   n-capric acid: positive
   Adipic acid: negative
   dl-malic acid: positive
   Sodium citrate: positive
   Phenyl acetate: positive <Bacteriological Properties of Strain P91>
Morphological characteristics:
   Cell shape and size: rod, 0.6 μm×1.5 μm
   Cell polymorphism: absent
   Mobility: positive
   Spore formation: negative
   Gram staining: negative
   Form of colony: circular, entire margin smooth, low convex, smooth surface, glossy, creamy color
Physiological properties:
   Catalase: positive
   Oxidase: positive
   O/F test: oxidative
   Nitrate reduction: negative
   Indole production: negative
   Glucose acidification: negative
   Arginine dihydrolase: positive
   Urease: negative
   Esculin hydrolysis: negative
   Gelatin hydrolysis: negative
   β-galactosidase: negative
   Production of fluorescence on King's B agar: positive:
Substrate assimilation:
   Glucose: positive
   L-arabinose: negative
   D-mannose: negative
   D-mannitol: negative
   N-acetyl-D-glucosamine: negative
   Maltose: negative
   Potassium gluconate: positive
   n-capric acid: positive
   Adipic acid: negative
   dl-malic acid: positive
   Sodium citrate: positive
   Phenyl acetate: positive <Bacteriological Properties of Strain P161>
Morphological characteristics:
   Cell shape and size: coccus, diameter 0.6 μm or bacillus 0.6 μm×1.5 to 2.0 μm
   Cell polymorphism: elongation
   Mobility: positive
   Spore formation: negative
   Gram staining: negative
   Form of colony: circular, entire margin smooth, low convex, smooth surface, and light yellow
Physiological properties:
   Catalase: positive
   Oxidase: positive
   O/F test: oxidative
   Nitrate reduction: positive
   Indole production: negative
   Glucose acidification: negative
   Arginine dihydrolase: positive Urease: negative
Esculin hydrolysis: negative
Gelatin hydrolysis: negative
β-galactosidase: negative
Production of fluorescence on King's B agar: positive
Substrate assimilation:
Glucose: positive
L-arabinose: positive
D-mannose: positive
D-mannitol: positive
N-acetyl-D-glucosamine: positive
Maltose: negative
Potassium gluconate: positive
n-capric acid: positive
Adipic acid: negative
dl-malic acid: positive
Sodium citrate: positive
Phenyl acetate: positive From the above described bacteriological properties, according to identification based on the Bergey's Manual of Systematic Bacteriology, Vol. 1 (1984) and Bergey's Manual of Determinative Bacteriology, 9th Ed. (1994), strains YN2 and H45 are identified to belong to *Pseudomonas cichorii* and strain P91 to *Pseudomonas putida*, respectively. Therefore, we gave names these strains as *Pseudomonas cichorii* YN2, *Pseudomonas cichorii* H45, and *Pseudomonas putida* P91.

On the other hand, though strain P161 was identified as to belong to the genus Pseudomonas, taxonomic identification was impossible on the basis of bacteriological properties. Then, in order to attempt identification based on genetic criteria, the DNA sequence, as shown in the FIG. 12, of 16s rRNA of P 161 was determined (SEQ ID NO:1) to test the homology with the DNA sequences of 16s rRNA of known microorganisms of genus Pseudomonas. As the result, a very high homology was found between sequences of the strain P161 and *Pseudomonas jessenii*. In addition, a high similarity was found between bacteriological properties of *Pseudomonas jessenii*, described on System. Appl. Microbiol. 20:137–149 (1997) and System. Appl. Microbiol. 22:45–58 (1999), and bacteriological properties of the strain P161. From the above described results, the strain P161 can be justifiably identified as *Pseudomonas jessenii* and hence, we named the strain P161 as *Pseudomonas jessenii* P161.

The strains YN2, H45, P91 and P161 are deposited in National Institute of Bioscience and Human-Technology, Agency of Industrial Science and Technology, the Japanese Ministry of International Trade and Industry by receiving identification code of FERM BP-7375, FERM BP-7374, FERM BP-7373, and FERM BP-7376, respectively.

By culturing these microorganisms using a material for introducing the desired monomer unit and a culture medium containing an alkanoate of the general Formula (12) and yeast extract, the objective PHA can be produced.

For normal cultivation microorganisms used for the production method for PHA of the present invention, for example, cultivation for preparation of a preservation of cell strain and keeping of cell number and active condition, excluding that influencing badly to growth and survival of microorganisms, any kinds of culture medium, for example, a general culture medium and an synthetic culture medium to which the nutrient source has been added, can be used. A cultivation condition such as temperature, aeration, and stirring is properly adjusted in accordance with the microorganism used.

On the other hand, in the case where production and accumulation of PHA is carried out by microorganisms, as the culture medium for PHA production, an inorganic culture medium containing at least alkanoate of the corresponding general Formula (12) can be used. It is the feature that in this case, as carbon or energy source other than alkanoate as the material of PHA, only the yeast extract is added.

As the inorganic culture medium used for the above described culture method, any one containing necessary components, such as a phosphor source (for example, phosphate salt) and nitrogen source (for example, ammonium salt and nitrate salt), for proliferation of microorganisms can be used. For example, as a representative inorganic culture medium, can be exemplified by MSB medium, E medium (J. Biol. Chem. 218: 97–106 (1956)), and M9 medium.

The composition of the M9 culture medium used in Examples of the present invention is as follows.

| | |
|---|---|
| $Na_2HPO_4$: | 6.2 g |
| $KH_2PO_4$: | 3.0 g |
| NaCl: | 0.5 g |
| $NH_4Cl$: | 1.0 g |

(for one liter culture medium; pH 7.0)

As the cultivation condition, shaking culture and stirring culture under 15 to 40° C., preferably 20 to 35° C., and aerobic condition are exemplified.

For cultivation steps, any method, used for normal microorganisms, such as batch system, fluidized batch system, semi-continuous culture, continuous culture, and reactor type can be used. A multi-step system by connecting a plurality of these steps may be utilized.

For example, as the method including the two steps of culture steps, in the first step, as the carbon source for cell proliferation, employing the inorganic culture medium containing about 0.1 wt % to 1.0 wt % of the yeast extract and about 0.01 wt % to 0.5 wt % of alkanoate of Formula (12), cultivation is conducted from the late stage of the logarithmic growth period to the point of a standing state period and in the second step, cells after completion of cultivation in the first step are collected by a centrifugation followed by a further cultivation in the inorganic culture medium containing about 0.01 wt % to 0.5 wt % of alkanoate of Formula (12) as the material and lacking any nitrogen source and after completion of cultivation, cells are collected to extract desired PHA.

There is the method in which cultivation is conducted in the inorganic culture medium to which about 0.1 wt % to 1.0 wt % of the yeast extract and about 0.01 wt % to 0.5 wt % of alkanoate of Formula (12) and at the point from the late stage of the logarithmic growth period to a standing state period, cells are collected to extract desired PHA.

In this case, a concentration of the yeast extract to be added to the culture medium is properly chosen in accordance with the kind of alkanoate of Formula (12), species and genus of the microorganism, a density of cells, or culture method. Normally, it is preferable to choose from a range from about 0.1 wt % to 1.0 wt % of content ratio in the culture medium in order to add it. On the other hand, for the yeast extract, any one of commercialized yeast extract generally used for cultivation of microorganisms can be preferably used. In addition, in replacement to the yeast extract, that prepared by pulverizing a lyophilized yeast product, which naturally contains the components of the yeast extract, can be also used. On the other hand, the concentration of alkanoate of Formula (12) as the material is properly chosen in accordance with species and genus of the microorganism, a density of cells, or culture method. Normally, it is preferable to choose from a range from about 0.01 wt % to 0.5 wt % of content ratio in the culture medium in order to add it.

In the case where any one of the strains YN2, H45, P91 and P161 previously described are used, in replacing to the yeast extract, a middle chain fatty acid of C6 to C12 (for example, octanoic acid, nonanoic acid, and the like), for example, is used as the carbon source for cell proliferation, PHA yielded is that in which the monomer unit derived from the middle chain fatty acid, which has been added, is mixed. Specifically, the case employing the method is exemplified, in which employing the inorganic culture medium, in which as the carbon source for cell proliferation, the middle chain fatty acid such as octanoic acid, nonanoic acid, and the like are added and also alkanoate of Formula (12) is added as the material, cultivation is conducted from the late stage of the logarithmic growth period to the point of a standing state period, cells are collected by centrifugation and then, the middle chain fatty acid and alkanoate of Formula (12) are added to carry out further cultivation in the inorganic culture medium lacking the nitrogen source. Or, the case employing the method is exemplified, in which the concentration of the nitrogen source is limited to $\frac{1}{10}$ in the inorganic culture medium, cultivation is carried out in the culture medium to which the middle chain fatty acid and alkanoate of Formula (12) are added, cells are collected in the period from the late stage of the logarithmic growth period to the point of a standing state period to extract the desired PHA. In the case where these methods, in which the middle chain fatty acid is added to the culture medium as the carbon source for cell proliferation, is applied, PHA yielded is becomes PHA, to which the monomer unit, derived from the middle chain fatty acid is added as the carbon source for cell proliferation, has been mixed.

In contrast, in the present invention, as described above, by cultivation of the above described microorganisms in the culture medium containing the yeast extract, alkanoate of Formula (12), and no other carbon source, the desired PHA, which contains a little amount of or no amount of any unnecessary monomer unit other than the monomer unit derived from the objective alkanoate of Formula (12), is produced and accumulated.

Collection of PHA from cells in the method according to the present invention is most conveniently carried out by extraction using such organic solvent as chloroform normally used. However, in an environment, in which the organic solvent is difficultly used, the method to collect PHA by removing cell components other than PHA by treatment with such surfactant as SDS, treatment with such enzyme as lysozyme, and treatment with such reagent as EDTA, sodium hypochlorite, and ammonium can be used.

The cultivation of microorganisms, production of PHA by microorganisms and accumulation in cells, and collection of PHA from cells are not restricted to the above described methods.

For example, and microorganisms used for production method of PHA, according to the present invention, microorganisms, other than the above described 4 bacterial strains, having productivity of PHA production, according to the present invention and similar to that of these 4 bacterial strains, can be used.

By using the above described methods, PHA having repeated units expressed by Formula (1) can be yielded. It is preferable that a number average molecular weight of this PHA is at least 10000 or more and a range of 10000 to 200000 is more preferable. In other words, to get stably a desired characteristic as a polymer, specifically, it is preferable that the PHA has repetition number to make the number average molecular weight to at least about 10000 to make characteristics, such as a glass transition temperature, softening point, melting point, crystallinity, and orientation which are designated by a structure of the monomer unit composing the monomer, to a specified range. On the other hand, for processing and the like, in consideration of convenience of processing such as dissolving operation, the number average molecular weight is preferably under about 200000. Usually, the range from 10000 to 100000 is more preferable. The number average molecular weight of PHA yielded by the production method according to the present invention is 10000 or more and about 20000 or more and is within the range expectable sufficiently of a stable expression of a physical property of the above described polymer.

EXAMPLES

Specific example will be presented below and the present invention will be explained in more detail. These specific examples are examples of the best mode according to the present invention. However, the present invention is not restricted to the following specific examples.

A

An example, in which the production method for polyhydroxyalkanoate according to the present invention is applied to the production of polyhydroxyalkanoate: poly-3-hydroxy-4-phenoxy butyric acid (PHPxB) consisting of the monomer unit, which is derived from 3-hydroxy-4-phenoxy butyric acid (3HPxB) expressed by Formula (5) using 4-phenoxy butyric acid (PxBA) of Formula (14) as the material, will be shown.

Example A-1

The strain P 91 was inoculated in a 200 ml of the M9 culture medium containing the yeast extract of 0.5% and PxBA of 0.1% and subjected to shaking-cultivation at 30° C. and 125 strokes/min. After 24 hours, cells were collected by centrifugation, suspended again in a 200 ml of the M9 culture medium containing a 0.1% PxBA and lacking the nitrogen source ($NH_4Cl$), and subjected to the shaking-cultivation at 30° C. and 125 strokes/min. After 24 hours, cells were collected by centrifugation, washed with cold methanol once, and subjected to freeze-dry.

This lyophilized pellet was suspended in chloroform of 100 ml and PHA was extracted by stirring at 60° C. for 20 hours. An extracted fluid was filtered using a membrane filter with a pore size of 0.45 $\mu$m followed by concentration by a rotary evaporator and then, concentrated fluid was precipitated again in cold methanol and precipitation only was collected and dried in vacuo to yield PHA. PHA yielded was subjected to methanolysis by a routine method followed by analysis by a gas chromatography mass spectrometry apparatus (GC-MS, Shimadzu QP-5050, EI method) and a methyl esterified product of the PHA monomer unit was identified. On the other hand, the molecular weight of this PHA was measured by gel permeation chromatography (GPC; Toso, HLC-8020, column: Polymer Laboratory, PLgel-MIXED-C (5 $\mu$m), solvent: chloroform, polystyrene converted molecular weight.)

Table 3 shows the result of identification and an average molecular weight. It is known that PHA yielded contains only monomer unit derived from 3-hydroxy-4-phenoxy butyric acid expressed by Formula (5) as the monomer unit and is a poly-3-hydroxy-4-phenoxy butyric acid.

Example A-2

The strain P 91 was inoculated in a 200 ml of the M9 culture medium containing the yeast extract of 0.5% and PxBA of 0.2% and subjected to shaking-cultivation at 30° C. and 125 strokes/min. After 48 hours, cells were collected by centrifugation, washed with cold methanol once, and subjected to freeze-drying.

This lyophilized pellet was suspended in chloroform of 100 ml and PHA was extracted by stirring at 60° C. for 20 hours. An extracted fluid was filtered using a membrane filter with a pore size of 0.45 μm followed by concentration by a rotary evaporator and then, concentrated fluid was precipitated again in cold methanol and precipitation only was collected and dried in vacuo to yield PHA. PHA yielded was subjected to methanolysis by a routine method followed by analysis by a gas chromatography mass spectrometry apparatus (GC-MS, Shimadzu QP-5050, EI method) and a methyl esterified product of the PHA monomer unit was identified. Table 4 shows the result of identification. It is known that PHA yielded contains only monomer unit derived from 3-hydroxy-4-phenoxy butyric acid expressed by Formula (5) as the monomer unit and is a poly-3-hydroxy-4-phenoxy butyric acid.

Example A-3

PHA collected from cultured cells of the strain P 91 was analyzed by using a nuclear magnetic resonance apparatus (FT-NMR: Bruker DPX400) under the following conditions.

Nuclear species for measurement: 1H, solvent used: heavy chloroform (containing TMS)

FIG. 1 shows the result of measurement and a Table 5 shows the result of analysis (attribute) of each signal. Table 5 shows the result of 3-hydroxy-4-phenoxy butyric acid described below. From the result, PHA contains only monomer unit derived from 3-hydroxy-4-phenoxy butyric acid expressed by Formula (5) and is confirmed that it is poly-3-hydroxy-4-phenoxy butyric acid.

B

The example, in which the production method for polyhydroxyalkanoate according to the present invention is applied to the production of polyhydroxyalkanoate: poly-3-hydroxy-5-phenoxy valeric acid (PHPxV) consisting of the monomer unit, which is derived from 3-hydroxy-5-phenoxy valeric acid (HPxVA) expressed by Formula (6) using 5-phenoxy valeric acid (PxVA) of Formula (15) as the material, will be shown.

Example B-1

Synthesis of PxVA

Dehydrated acetone of 240 ml was put in a 3-necked round-bottom flask, potassium iodide (0.06 mol), potassium carbonate (0.11 mol), and phenol (0.07 mol) were added to stir sufficiently. In this solution, 5-bromo valeric acid ethyl ester (0.06 mol) was dropped in a nitrogen atmosphere and refluxed at 60±5° C. to react for 24 hours. After completion of the reaction, a reaction solution was exsiccated to condensation using an evaporator, and dissolved again in methylene chloride, and water was added to the solution to separate and an organic layer was dehydrated by using magnesium sulfate anhydride followed by exsiccation for condensation using the evaporator. Hot methanol was added to a dried matter (reactant) yielded to dissolve and cooled slowly to precipitate again, resulting in a yield of 5-phenoxy valeric acid ethyl ester (PxVA). At this point, the yield ratio of this ester to 5-bromo valeric acid ethyl ester was 72 mol %.

Reactant (ester) yielded was dissolved in ethanol water (9:1 (v/v)) to make 5 wt %, potassium hydroxide of 10 times mol was added to react at 0 to 4° C. for 4 hours to carry out hydrolysis of the ester. This reaction solution was added to 0.1 mol hydrochloric acid aqueous solution of 10 times volume and then, precipitation was collected by filtration. The precipitation (reactant) collected was dried under a reduced pressure under a room temperature for 36 hours. The dried matter yielded was dissolved in a small volume of hot methanol, the solution was gradually cooled to precipitate again, and the precipitation was dried under a reduced pressure under the room temperature for 24 hours resulting in yield of 5-phenoxy valeric acid, the objective compound. The yield ratio of this objective compound to 5-bromo valeric acid ethyl ester was 53 mol %.

The analysis of the compound yielded was conducted by the nuclear magnetic resonance apparatus (NMR) under the following conditions.

<Instruments Used>
FT-NMR: Bruker DPX400
$^1$H resonance frequency: 400 MHZ
<Condition of Measurement>
Nuclear species for measurement: 1H
Solvent used: $CDCl_3$
Reference: sealed in a capillary tube $TMS/CDCl_3$
Temp. for measurement: room temp.

Figure 2:
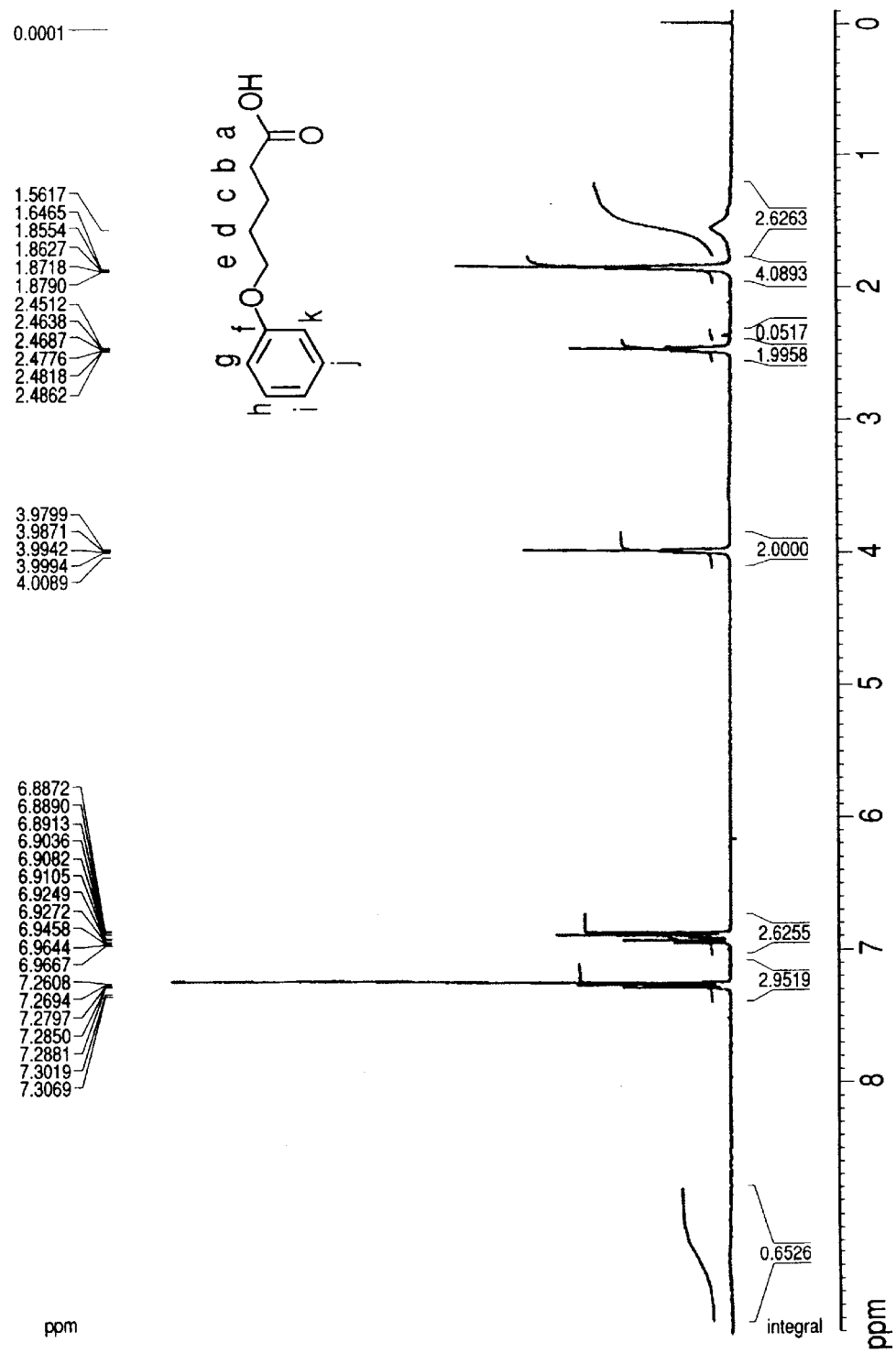
FIG. 2 is an NMR spectrum of 5-phenoxy valeric acid obtained in Example B-1.

FIG. 2 shows a chart of the spectrum and Table 6 shows the result of identification.

From the result, synthesis of the desired PxVA was confirmed.

Example B-2

Production of PHPxV Homopolymer by Strain P91.

The strain P 91 was inoculated in a 200 ml of the M9 culture medium containing the yeast extract (DIFCO made) of 0.5 wt % and PxVA of 0.1 wt % and subjected to shaking-cultivation at 30° C. and 125 strokes/min. After 24 hours, cells were collected by centrifugation, suspended again in 200 ml of the M9 culture medium containing 0.1% PxVA and lacking any nitrogen source ($NH_4Cl$), and further subjected to the shaking cultivation at 30° C. and 125 strokes/min. After 24 hours, cells were collected by centrifugation, washed with cold methanol once, and subjected to freeze-drying and weighing.

This lyophilized pellet was suspended in chloroform of 100 ml and PHA was extracted by stirring at 60° C. for 20 hours. The extracted fluid was filtered using a membrane filter with the pore size of 0.45 μm followed by concentration by the rotary evaporator and then, concentrated fluid was precipitated again in cold methanol and precipitation only was collected and dried in vacuo to yield PHA and weigh. Table 7 shows the yields of cells and the polymer.

Figure 3A:
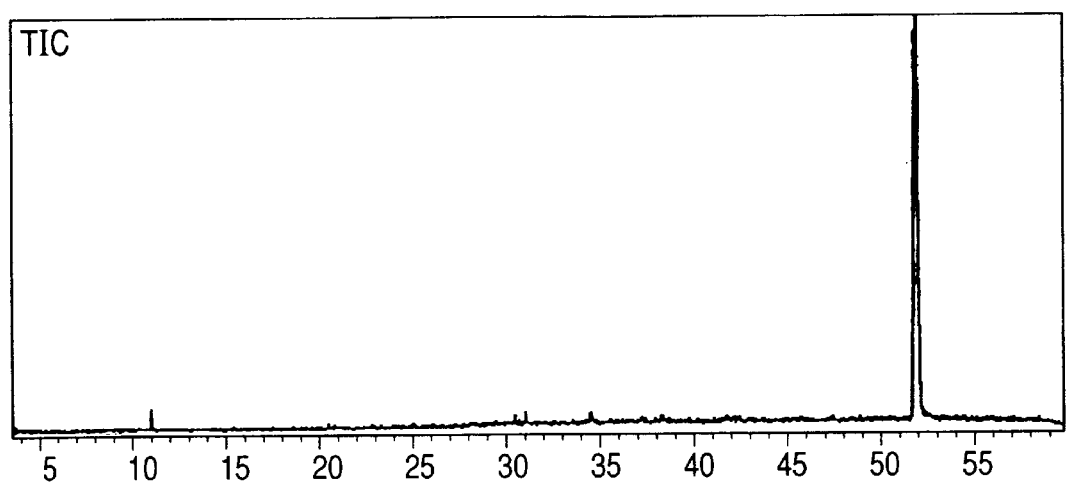
FIG. 3A is a total ion chromatogram (TIC) of GC-MS measurement of a methyl esterified compound of the monomer unit composing PHA obtained in Example B-2.
Figure 3B:
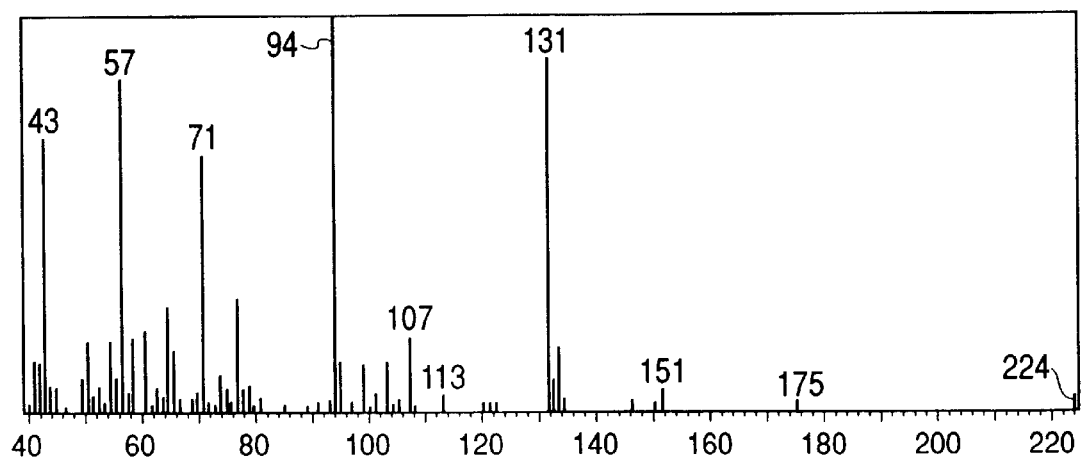
FIG. 3B is a mass spectrum of a main peak in the TIC.

A composition of PHA yielded was analyzed according to the following steps. PHA sample of 5 mg was put in an egg-shaped flask of 25 ml volume, methanol of 2 ml containing chloroform of 2 ml and sulfuric acid of 3% (v/v) was added to reflux at 100° C. for 3.5 hours, and water was added to separate, and then, the organic layer was analyzed by the gas chromatography mass spectrometry apparatus (GC-MS, Shimadzu QP-5050, DB-WAXETR (J & W Co. made), EI method) and a methyl esterified product of the PHA monomer unit was identified. As the result, there was a single main peak. From the mass spectrum thereof, it was known as methyl esterified compound of 3-hydroxy-5-phenoxy valeric acid. In addition, other small components had no relation with the monomer unit of PHA. FIGS. 3A and 3B show the total ion chromatogram (TIC) of GC-MS and the mass spectrum of the main peak.

The polymer yielded was subjected to NMR analysis under the following condition.
<Instruments Used>
FT-NMR: Bruker DPX400
$^1$H resonance frequency: 400 MHz
<Condition of Measurement>
Nuclear species for measurement: 1H
Solvent used: $CDCl_3$
Reference: sealed in a capillary tube $TMS/CDCl_3$
Temp. for measurement: room temp.

Figure 4:
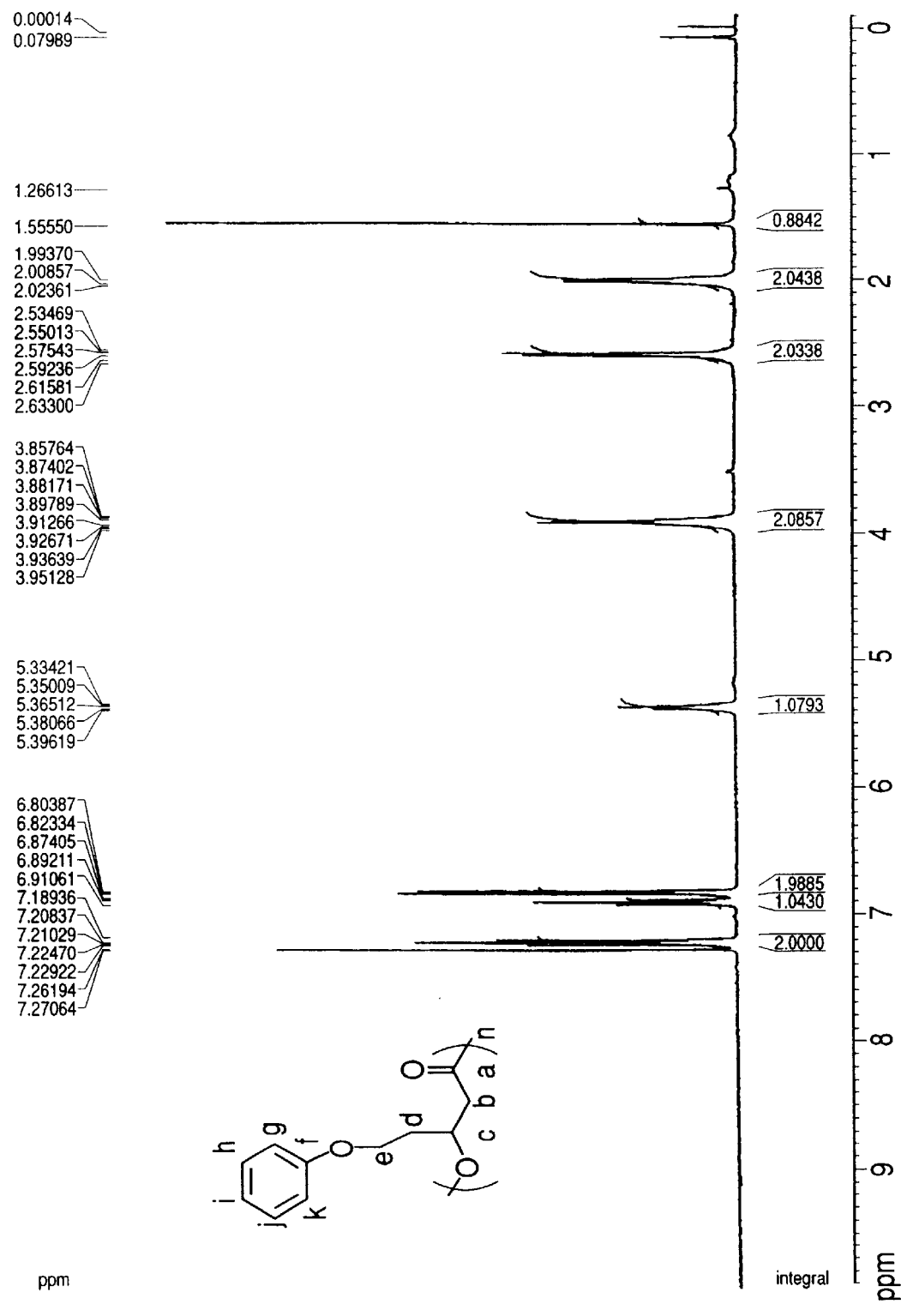
FIG. 4 is an NMR spectrum of PHA obtained in Example B-2.

FIG. 4 shows the chart of the spectrum and Table 8 shows the result of identification.

In addition, the molecular weight of the PHA yielded was measured by gel permeation chromatography (GPC; Toso, HLC-8020, column: Polymer Laboratory, PLgel-MIXED-C (5 μm), solvent: chloroform, polystyrene conversion). The result was Mn=70000 and Mw=121000.

As the above described result, according to the present invention, the homopolymer of poly-3-hydroxy-5-phenoxy valeric acid using PxVA as the material and production method thereof were shown.

Example B-3

Production of PHPxV Homopolymer by the Strain H45.

The strain H45 was inoculated in a 200 ml of the M9 culture medium containing the yeast extract (DIFCO made) of 0.5 wt % and PxVA of 0.1 wt % and subjected to shaking-cultivation at 30° C. and 125 strokes/min. After 24 hours, cells were collected by centrifugation, washed with cold methanol once, and subjected to freeze-drying and weighing.

This lyophilized pellet was suspended in chloroform of 100 ml and PHA was extracted by stirring at 60° C. for 20 hours. The extracted fluid was filtered using a membrane filter with the pore size of 0.45 μm followed by concentration by the rotary evaporator and then, concentrated fluid was precipitated again in cold methanol and precipitation only was collected and dried in vacuo to yield PHA and weigh. Table 9 shows the yields of cells and the polymer.

Figure 5A:
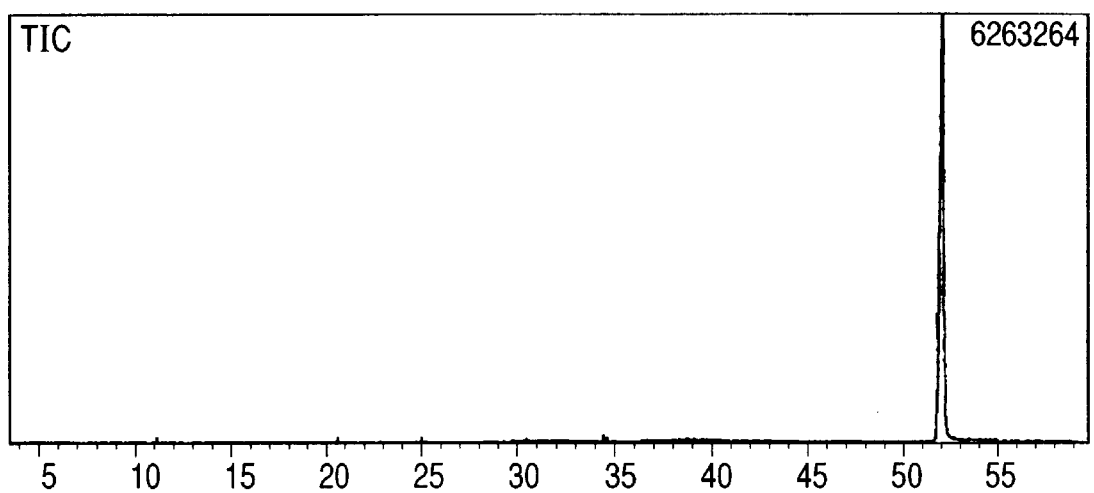
FIG. 5A is a total ion chromatogram (TIC) of GC-MS measurement of a methyl esterified compound of the monomer unit composing PHA obtained in Example B-3.
Figure 5B:
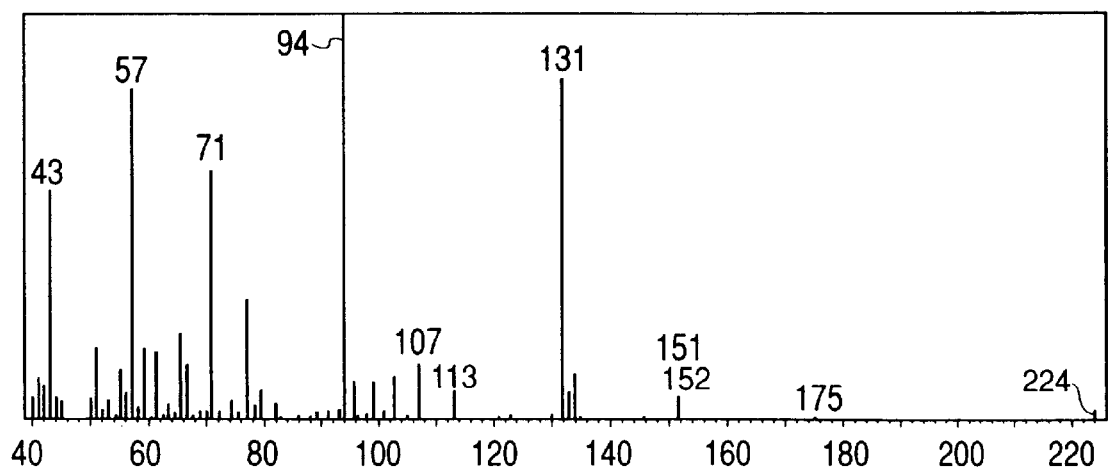
FIG. 5B is a mass spectrum of a main peak in the TIC.

The composition of PHA yielded was analyzed according to the following steps. PHA sample of 5 mg was put in the egg-shaped flask of 25 ml volume, methanol of 2 ml containing chloroform of 2 ml and sulfuric acid of 3% (v/v) was added to reflux at 100° C. for 3.5 hours, and water was added to separate, and then, the organic layer was analyzed by the gas chromatography mass spectrometry apparatus (GC-MS, Shimadzu QP-5050, DB-WAXETR (J & W Co. made), EI method) and the methyl esterified product of the PHA monomer unit was identified. As the result, there was a single main peak. From the mass spectrum thereof, it was known as methyl esterified compound of 3-hydroxy-5-phenoxy valeric acid. In addition, other small components had no relation with the monomer unit of PHA. FIGS. 5A and 5B show the total ion chromatogram (TIC) of GC-MS and the mass spectrum of the main peak.

In addition, the molecular weight of the PHA yielded was measured by gel permeation chromatography (GPC; Toso, HLC-8020, column: Polymer Laboratory, PLgel-MIXED-C (5 μm), solvent: chloroform, polystyrene conversion.) The result was Mn=64000 and Mw=116000.

As the above described result, according to the present invention, the homopolymer of poly-3-hydroxy-5-phenoxy valeric acid using PxVA as the material and production method thereof were shown.

C

The example, in which the production method for polyhydroxyalkanoate according to the present invention is applied to the production of polyhydroxyalkanoate: poly-3-hydroxy-5-(4-fluorophenoxy) valeric acid (PHFPxV) consisting of the monomer unit, which is derived from 3-hydroxy-5-(4-fluorophenoxy) valeric acid (HFPxVA) expressed by Formula (16) using 5-(4-fluorophenoxy) valeric acid (FPxVA) of Formula (17) as the material, will be shown.

Example C-1

Synthesis of FPxVA

Sodium iodide (0.06 mol), potassium carbonate (0.11 mol), and 4-fluorophenol (0.07 mol) were added to 240 ml of dehydrated acetone in a three-neck round-bottom flask and the mixture was stirred fully. To the solution was dripped 5-bromovaleric acid ethyl ester (0.06 mol) in a nitrogen atmosphere and the mixture was refluxed at 60±5° C. and allowed to react for 24 hours. After the completion of reaction, the reactant solution was concentrated to dryness using an evaporator. The residue was dissolved in methyl chloride again and water added, followed by separation. The separated organic solvent layer was dehydrated with anhydrous magnesium sulfate and concentrated to dryness using an evaporator to obtain the reactant.

Hot water was added to dissolve the obtained reactant and the solution gradually cooled to precipitate 5-(4-fluorophennoxy) valeric acid ethyl ester again. Here, the yield rate of the compound to 5-bromo valeric acid ethyl ester was 68 mol %.

The obtained reactant (ester) was dissolved in ethanol-water (9:1 (v/v)) to make a 5 wt % solution, 10 times the mol of potassium hydroxide added, and the mixture allowed to react at 0 to 4° C. for 4 hours to hydrolyze the ester.

The reactant solution was added in 10 times the volume of 0.1 M hydrochloric acid and the precipitate collected by filtration. The collected precipitate (the reactant) was dried under decreased pressure at room temperature for 36 hours. The dried reactant was dissolved in a small amount of hot ethanol and the solution gradually cooled for reprecipitation. The precipitate was dried under decreased pressure at room temperature for 24 hours to obtain the goal compound 5-(4-fluorophenoxy) valeric acid expressed as Equation (17). The yield rate of this compound to 5-bromo valeric acid ethyl ester was 49 mol %.

The obtained compound was analyzed using NMR under the following conditions.
<Instrument>
FT-NMR: Bruker DPX400
$^1$H resonance frequency: 400 MHZ
<Measurement Conditions>
Nuclide: $^1$H
Solvent: $CDCl_3$
Reference: $TMS/CDCl_3$ sealed into a capillary
Temperature: Room temperature FIG. 6 shows the $^1$H-NMR spectrum chart and Table 10 indicates the results of identification.

From the above-mentioned results, it was confirmed that the goal FPxVA was synthesized.

Example C-2

Production of PHFPxV Homopolymer Using Strain P91

The strain P91 was inoculated in 200 ml of M9 medium containing 0.5 wt % yeast extract (DIFCO) and 0.1 wt % FPxVA and subjected to shake culture at 30° C. and at 125 strokes/min. After 24 hours, the bacterial cells were collected by centrifugation and suspended again in 200 ml of M9 medium containing 0.1 wt % FPxVA without a nitrogen source ($NH_4Cl$), followed by shake culture at 30° C. and at 125 strokes/min. After 24 hours, the bacterial cells were collected by centrifugation, washed with cold methanol once, lyophilized, and weighed.

The lyophilized pellet was suspended in 100 ml of chloroform and stirred at 60° C. for 20 hours to extract PHA. The extract solution was filtered with a 0.45-μm membrane filter and concentrated using a rotary evaporator. The concentrate was reprecipitated in cold methanol and the precipitate was collected and vacuum-dried to obtain PHA. The obtained PHA was weighed. Table 11 shows the yields of the bacterial cell and polymer.

Figure 7A:
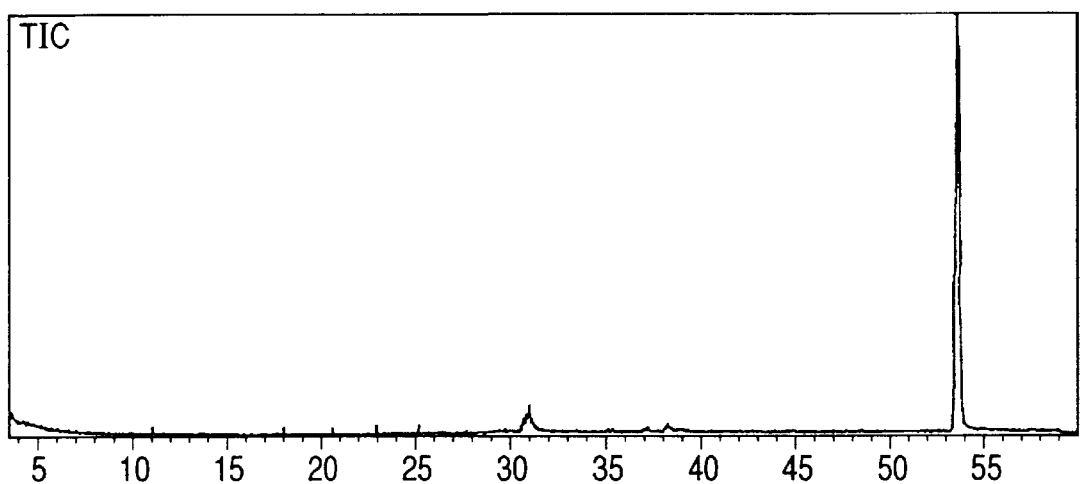
FIG. 7A is a total ion chromatogram (TIC) of GC-MS measurement of a methyl esterified compound of the monomer unit composing PHA obtained in Example C-2.
Figure 7B:
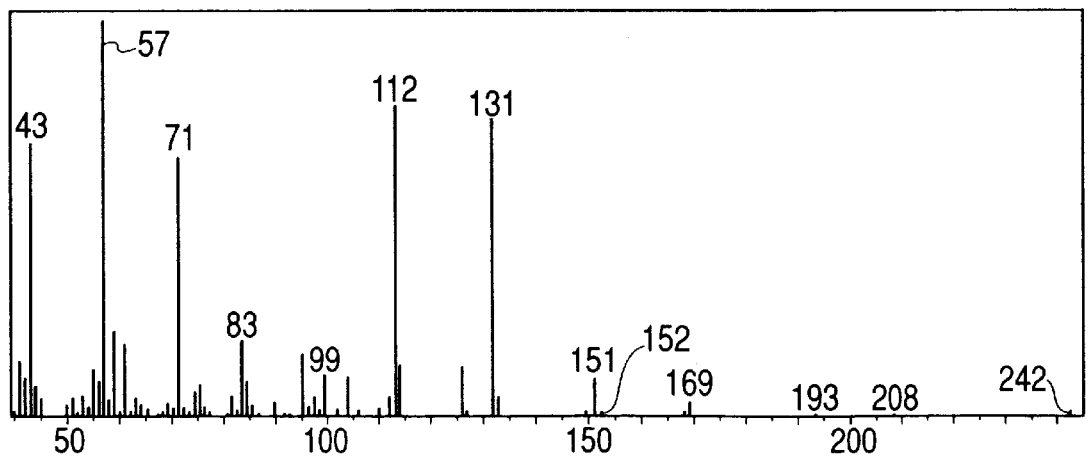
FIG. 7B is a mass spectrum of a main peak in the TIC.

The obtained PHA was analyzed for composition as follows: 5 mg of the PHA sample was put in a 25-ml eggplant-type flask, 2 ml of chloroform and 2 ml of methanol containing 3% (v/v) sulfuric acid added, the mixture refluxed at 100° C. for 3.5 hours, and water added for separation. After separation, the organic solvent layer was analyzed using gas chromatography-mass spectrometry (GC-MS, Shimadzu QP-5050, column: DB-WAXETR (J & W Co.), EI method) to identify the methyl ester of PHA monomer unit. Consequently, only one main peak was shown and identified as the methyl ester of 3-hydroxy-5-(4-fluorophenoxy) valeric acid by mass spectrometry. The other trace components were unrelated to the PHA monomer unit. FIGS. 7A and 7B show the TCI and mass spectrum of the methyl ester of 3-hydroxy-5-(4-fluorophenoxy) valeric acid.

The molecular weight of the obtained PHA was determined using gel permeation chromatography (GPC; Toso HLC-8020, column: Polymer Laboratory PLgel MIXED-C (5 μm), solvent: chloroform, polystyrene conversion): Mn=68000 and Mw=120000.

Figure 8:
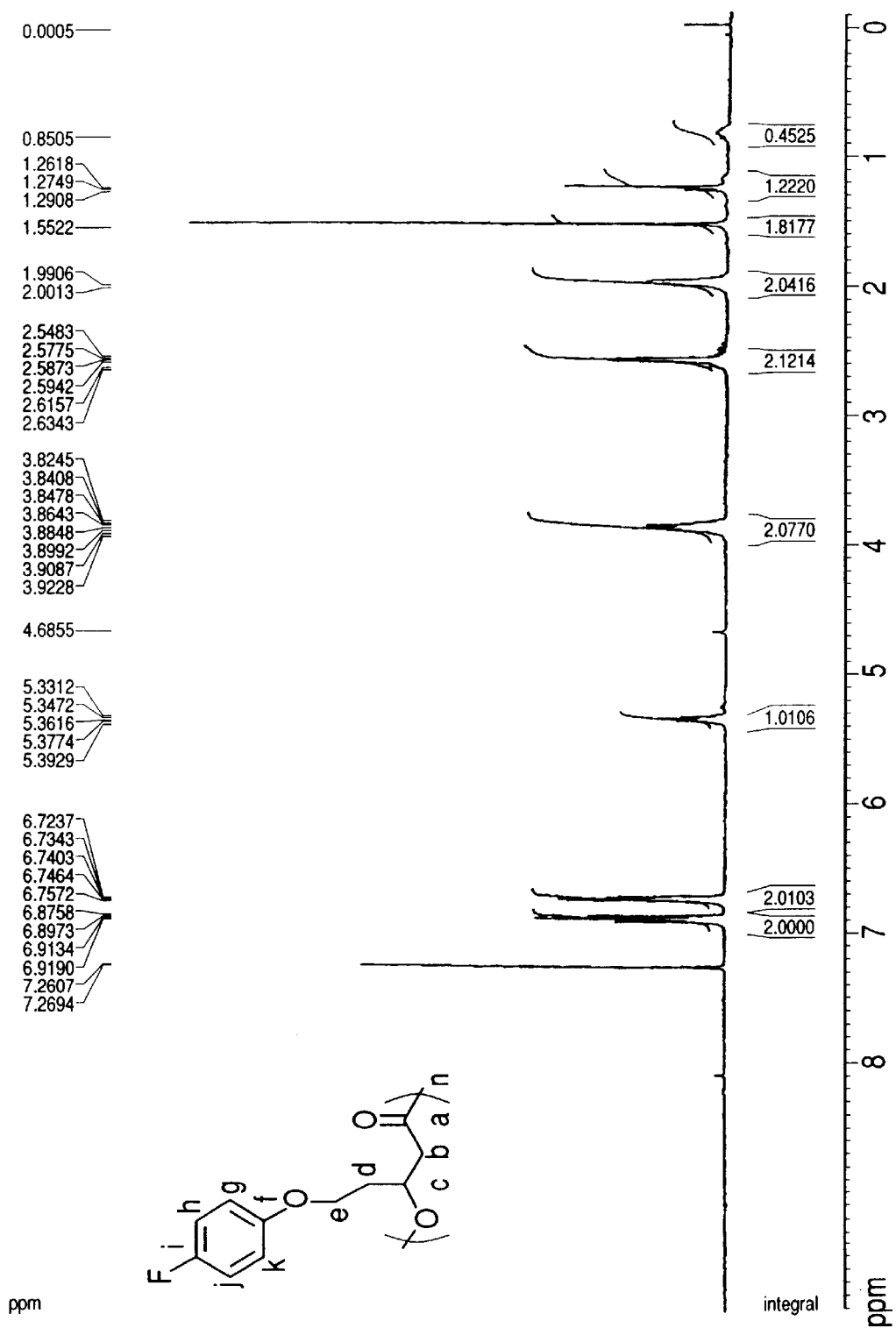
FIG. 8 is an NMR spectrum of PHA obtained in Example C-2.

The obtained PHA was further analyzed for structure using nuclear magnetic resonance (NMR) under the following conditions.
<Instrument>
FT-NMR: Bruker DPX400
$^1H$ Resonance frequency: 400 MHz
<Measurement Conditions>
Nuclide: $^1H$
Solvent: $CDCl_3$
Reference: $TMS/CDCl_3$ sealed in capillary
Temperature: Room temperature FIG. 8 shows the $^1H$-NMR spectrum chart and Table 12 the results of the identification.

Consequently, the poly-3-hydroxy-5-(4-fluorophenoxy) valerate homopolymer using FPxVA as the material and its production method according to this invention have been shown.

Example C-3

Production of PHFPxV Homopolymer Using Strain H45

The cells of strain H45 were inoculated in 200 ml of M9 medium containing 0.5 wt % yeast extract (DIFCO) and 0.1 wt % FPxVA and subjected to shake culture at 30° C. and at 125 strokes/min. After 24 hours, the bacterial cells were collected by centrifugation, washed with cold methanol once, lyophilized, and weighed.

The lyophilized pellet was suspended in 100 ml of chloroform and stirred at 60° C. for 20 hours to extract PHA. The extract was filtered with a 0.45-μm membrane filter and concentrated using a rotary evaporator. The concentrate was reprecipitated in cold methanol and the precipitate was collected and vacuum-dried to obtain and weigh PHA. Table 13 shows the yields of the bacterial cells and polymer.

Figure 9A:
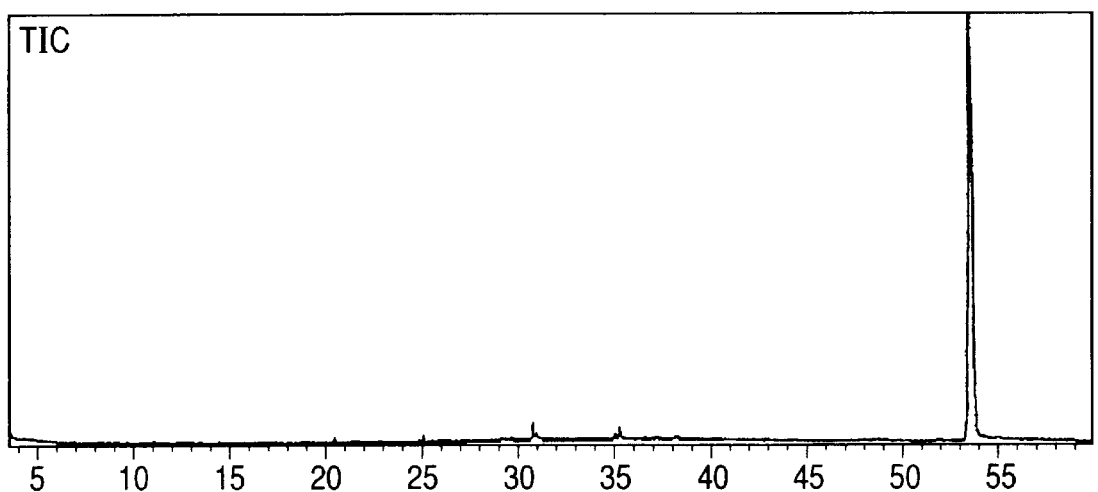
FIG. 9A is a total ion chromatogram (TIC) of GC-MS measurement of a methyl esterified compound of the monomer unit composing PHA obtained in Example C-3.
Figure 9B:
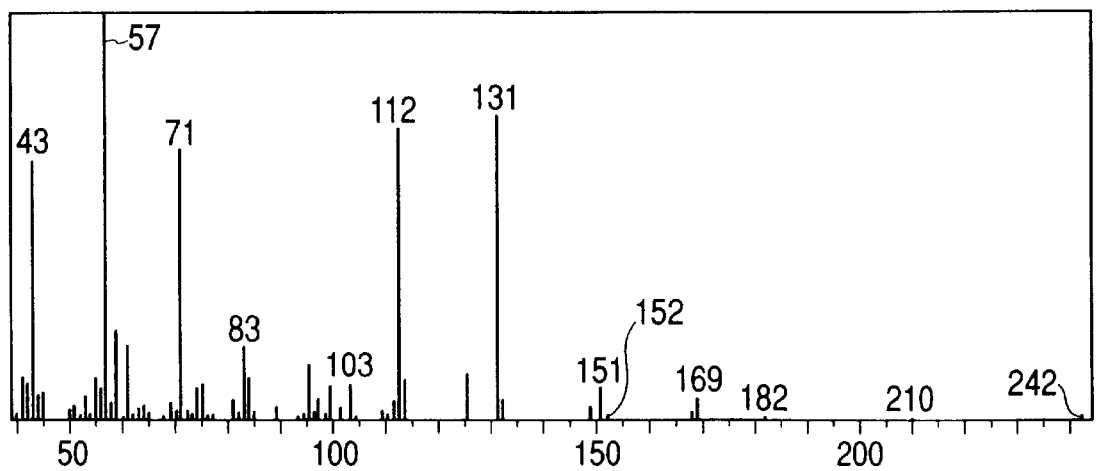
FIG. 9B is a mass spectrum of a main peak in the TIC.

The obtained PHA was analyzed for composition as follows: 5 mg of the PHA sample was put in a 25-ml eggplant-type flask, 2 ml of chloroform and 2 ml of methanol containing 3% (v/v) sulfuric acid added, the mixture refluxed at 100° C. for 3.5 hours, and water added for separation. After separation, the organic solvent layer was analyzed using gas chromatography-mass spectrometry (GC-MS, Shimadzu QP-5050, column: DB-WAXETR (J & W Co.), EI method) to identify the methyl ester of PHA monomer unit. Consequently, only one main peak was shown and identified as the methyl ester of 3-hydroxy-5-(4-fluorophenoxy) valeric acid by mass spectrometry. FIGS. 9A and 9B show the GC-MS total ion chromatogram (TIC) and mass spectrum of the main peak.

The molecular weight of the obtained PHA was determined using gel permeation chromatography (GPC; Toso HLC-8020, column: Polymer Laboratory PLgel MIXED-C (5 μm), solvent: chloroform, polystyrene conversion): Mn=67000 and Mw=119000.

Consequently, the poly-3-hydroxy-5-(4-fluorophenoxy) valerate homopolymer using FPxVA as the material and its production method according to this invention have been shown.

D

There are given examples of the production method for polyhydroxyalkanoate according to this invention applied to the production of polyhydroxyalkanoate composed of the monomer unit derived from 3-hydroxy-5-phenyl valeric acid (HPVA) expressed as Equation (9), for which the material is 5-phenyl valeric acid (PVA) expressed as Equation (18): poly-3-hydroxy-5-phenyl valerate (PHPV).

Example D-1

The strain H45 was inoculated in 200 ml of medium M9 containing 0.5% yeast extract (Difco Co.) and 0.05% PVA and subjected to shake culture at 30° C. and at 125 strokes/min. After 24 hours, the bacterial cells were collected by centrifugation, washed with cold methanol once, and lyophilized.

The lyophilized pellet was suspended in 100 ml of chloroform and stirred at 60° C. for 20 hours to extract PHA. The extract solution was filtered with a 0.45-μm membrane filter and concentrated using a rotary evaporator. The concentrate was reprecipitated in cold methanol and the precipitate was collected and vacuum-dried to obtain PHA. The obtained PHA was subjected to -methanolysis by the usual method and analyzed using gas chromatography-mass spectrometry (GC-MS, Shimadzu QP-5050, EI method) to identify the methyl ester of the PHA monomer unit. The molecular weight of the PHA was determined using gel permeation chromatography (GPC: Toso HLC-8020, column: Polymer Laboratory•PLgel•MIXED-C•5 μm, solvent; chloroform, polystyrene-converted molecular weight). Table 14 shows the results of identification, average molecular weight, and the yield and yield rate of the lyophilized pellet and collected polymer.

As shown in Table 14, the polymer, extracted and collected from the bacterial cells has been confirmed to contain only the monomer unit derived from 3-hydroxy-5-phenyl valeric acid expressed as Equation (9) as the PHA monomer unit.

Example D-2

The strain H45 was inoculated in 200 ml of M9 medium containing 0.5% yeast extract (Difco Co.) and 0.1% PVA and subjected to shake culture at 30° C. and at 125 strokes/min. After 24 hours, the bacterial cells were collected by centrifugation, suspended again in 200 ml of medium M9 containing 0.2% PVA without a nitrogen source ($NH_4Cl$), and subjected to shake culture at 30° C. and at 125 strokes/min. After 24 hours, the bacterial cells were collected by centrifugation, washed with cold methanol once, and lyophilized.

The lyophilized pellet was suspended in 100 ml of chloroform and stirred at 60° C. for 20 hours to extract PHA. The extract solution was filtered with a 0.45-$\mu$m membrane filter and concentrated using a rotary evaporator. The concentrate was reprecipitated in cold methanol and the precipitate was collected and vacuum-dried to obtain PHA. The obtained PHA was subjected to methanolysis by the usual method and analyzed using gas chromatography-mass spectrometry (GC-MS, Shimadzu QP-5050, EI method) to identify the methyl ester of PHA monomer unit. The molecular weight of the PHA was determined using gel permeation chromatography (GPC: Toso HLC-8020, column: Polymer Laboratory•PLgel•MIXED-C•5 $\mu$m, solvent: chloroform, polystyrene-converted molecular weight). Table 15 shows the results of identification, average molecular weight, and the yield and yield rate of lyophilized pellet and collected polymer.

As shown in Table 15, the polymer, extracted and collected from the bacterial cells has been confirmed to contain only the monomer unit derived from 3-hydroxy-5-phenyl valeric acid expressed as Equation (9), as the PHA monomer unit.

Example D-3

The strain P91 was inoculated in 200 ml of M9 medium containing 0.5% yeast extract (Difco Co.) and 0.1% PVA and subjected to shake culture at 30° C. and at 125 strokes/min. After 24 hours, the bacterial cells were collected by centrifugation, suspended again in 200 ml of M9 medium containing 0.1% PVA without a nitrogen source ($NH_4Cl$), and subjected to shake culture at 30° C. and at 125 strokes/min. After 24 hours, the bacterial cells were collected by centrifugation, washed with cold methanol once, and lyophilized.

The dried pellet was suspended in 100 ml of chloroform and stirred at 60° C. for 20 hours to extract PHA. The extract solution was filtered with a 0.45-$\mu$m membrane filter and concentrated using a rotary evaporator. The concentrate was reprecipitated in cold methanol and the precipitate was collected and vacuum-dried to obtain PHA. The PHA was subjected to methanolysis by the usual method and analyzed using gas chromatography-mass spectrometry (GC-MS, Shimadzu QP-5050, EI method) to identify the methyl ester of PHA monomer unit. Table 16 shows the results of identification and the yield and yield rate of the lyophilized pellet and collected polymer.

As shown in Table 16, the polymer, extracted and collected from the bacterial cells has been confirmed to contain only the monomer unit derived from 3-hydroxy-5-phenyl valeric acid expressed as Equation (9), as the PHA monomer unit.

Example D-4

The strain P161 was inoculated in 200 ml of medium M9 containing 0.5% yeast extract (Difco Co.) and 0.1% PVA and subjected to shake culture at 30° C. and at 125 strokes/min. After 24 hours, the bacterial cells were collected by centrifugation, suspended again in 200 ml of M9 medium containing 0.1% PVA without a nitrogen source ($NH_4Cl$), and subjected to shake culture at 30° C. and at 125 strokes/min. After 24 hours, the bacterial cells were collected by centrifugation, washed with cold methanol once, and lyophilized.

This lyophilized pellet was suspended in 100 ml of chloroform and stirred at 60° C. for 20 hours to extract PHA. The extract solution was filtered with a 0.45-$\mu$m membrane filter and concentrated using a rotary evaporator. The concentrate was reprecipitated in cold methanol and the precipitate was collected and vacuum-dried to obtain PHA. The obtained PHA was subjected to methanolysis by the usual method and then analyzed using gas chromatography-mass spectrometry (GC-MS, Shimadzu QP5050, EI method) to identify the methyl ester of PHA monomer unit. The molecular weight of the obtained PHS was determined by gel permeation chromatography (GPC; Toso•HLC-8020, column: Polymer Laboratory•PLgel•Mixed-C•5 $\mu$m, solvent: chloroform, polystyrene-concerted molecular weight). Table 17 shows the results of identification, average molecular weight, and the yield and yield rate of lyophilized pellet and collected polymer.

As shown in Table 17, the polymer, extracted and collected from the bacterial cells has been confirmed to contain only the monomer unit derived from 3-hydroxy-5-phenyl valeric acid, expressed as Equation (9), as the PHA monomer.

Example D-5

Figure 10:
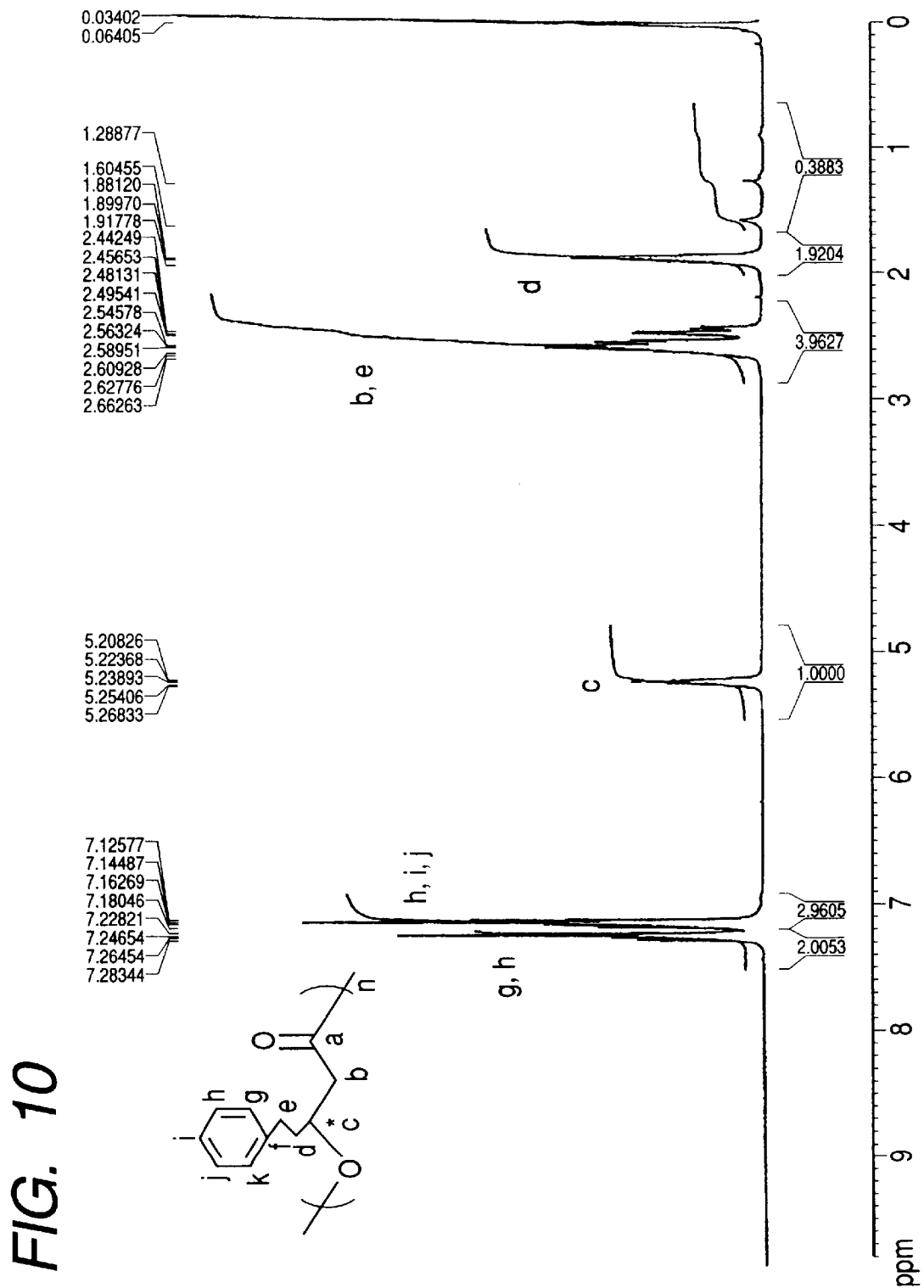
FIG. 10 is an $^1$H-NMR spectrum of poly-3-hydroxy-5-phenyl valeric acid produced by strain H45 in Example D-5.
Figure 11:
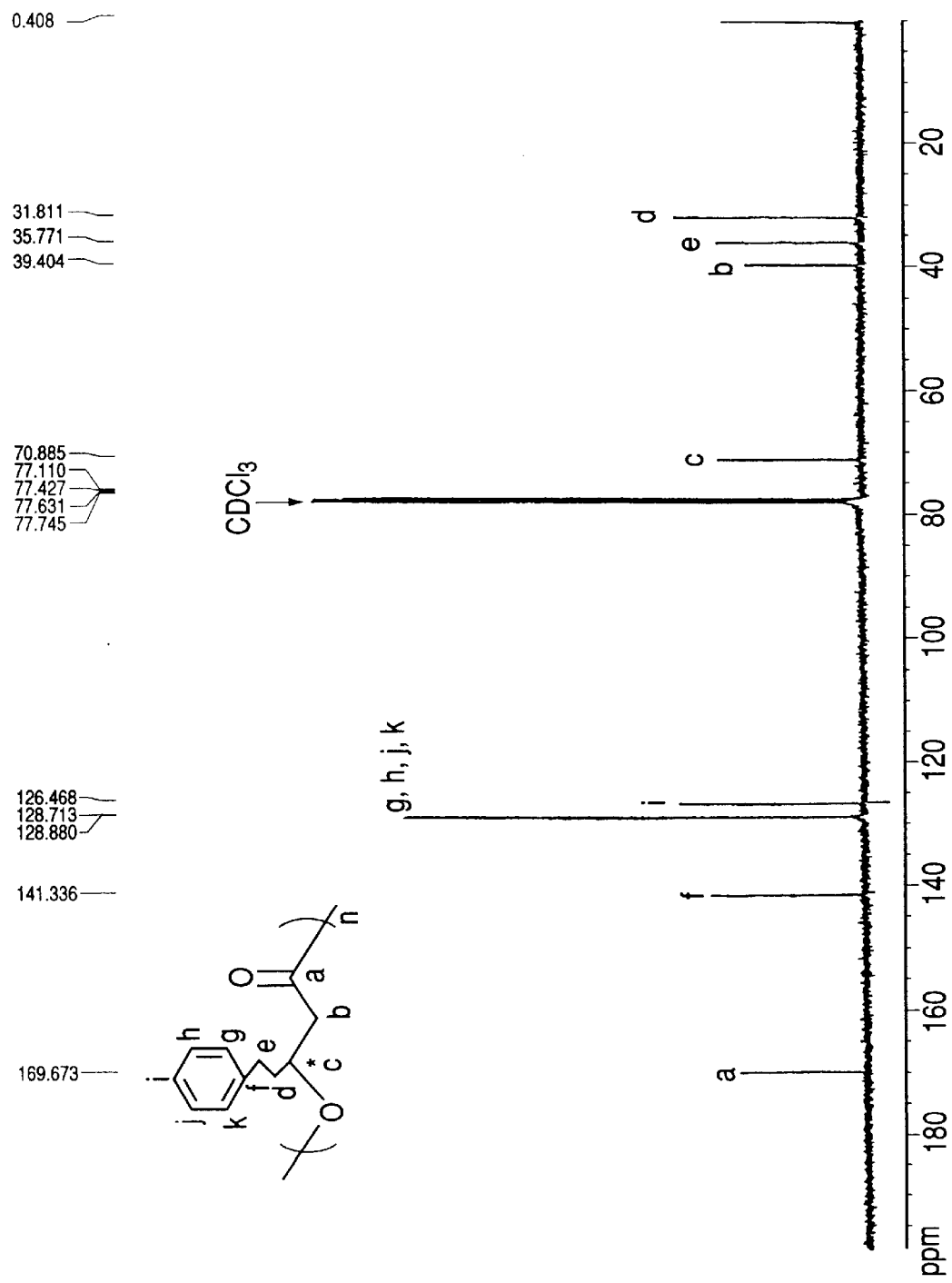
FIG. 11 is a $^{13}$C-NMR spectrum of poly-3-hydroxy-5-phenyl valeric acid produced by strain H45 in Example D-5.

PHPV, produced through the strain H45 was analyzed using nuclear magnetic resonance (FT-NMR: Bruker DPX400) under the following conditions: nuclide: $^1$H and $^{13}$C, solvent: heavy chloroform (containing TMS). FIG. 10 shows the $^1$H-NMR spectrum chart and Table 18 lists the identification of each peak. FIG. 11 shows the $^{13}$C-NMR spectrum chart and Table 19 lists the identification of each peak.

Consequently, the polymer, extracted and collected from the bacterial cells, has been shown to be poly-3-hydroxy-5-phenyl valeric acid containing only the monomer unit derived from 3-hydroxy-5-phenyl valeric acid expressed as Equation (9), as the PHA monomer unit.

E

There are given examples of the production method for polyhydroxyalkanoate according to this invention applied to the production of polyhydroxyalkanoate consisting of the monomer unit derived from 3-hydroxy-5-(4-fluorophenyl) valeric acid (HFPVA) expressed as Equation (7) for which the material is 5-(4-fluorophenyl) valeric acid (FPVA) expressed as Equation (19): poly-3-hydroxy-5-(4-fluorophenyl) valerate (PHFPV).

Example E-1

The substrate FPVA was synthesized first through Grignard reaction as shown in Macromolecules, 29, 1762–1766

(1996) and 27, 45–49 (1994): 5-bromo valeric acid was dissolved in anhydrous tetrahydrofuran (THF) and a 3M methylmagnesiumchloride THF solution was added by dripping at −20° C. in an argon atmosphere. After stirring for 15 minutes, a THF solution of 1-bromo-4-fluorobenzene and magnesium was further dripped and a 0.1M $Li_2CuCl_4$ THF solution added (the temperature was kept at −20° C.). The temperature of the reaction solution was returned to the room temperature. The solution was stirred overnight, then poured in 20% ice-cooled sulfuric acid and stirred. The water layer was collected and saturated with sodium chloride, followed by extraction with ether. The extract was further extracted with 100 ml of deionized water including 50 g of potassium hydroxide and oxidized with 20% sulfuric acid, followed by collection of the precipitate.

Figure 13:
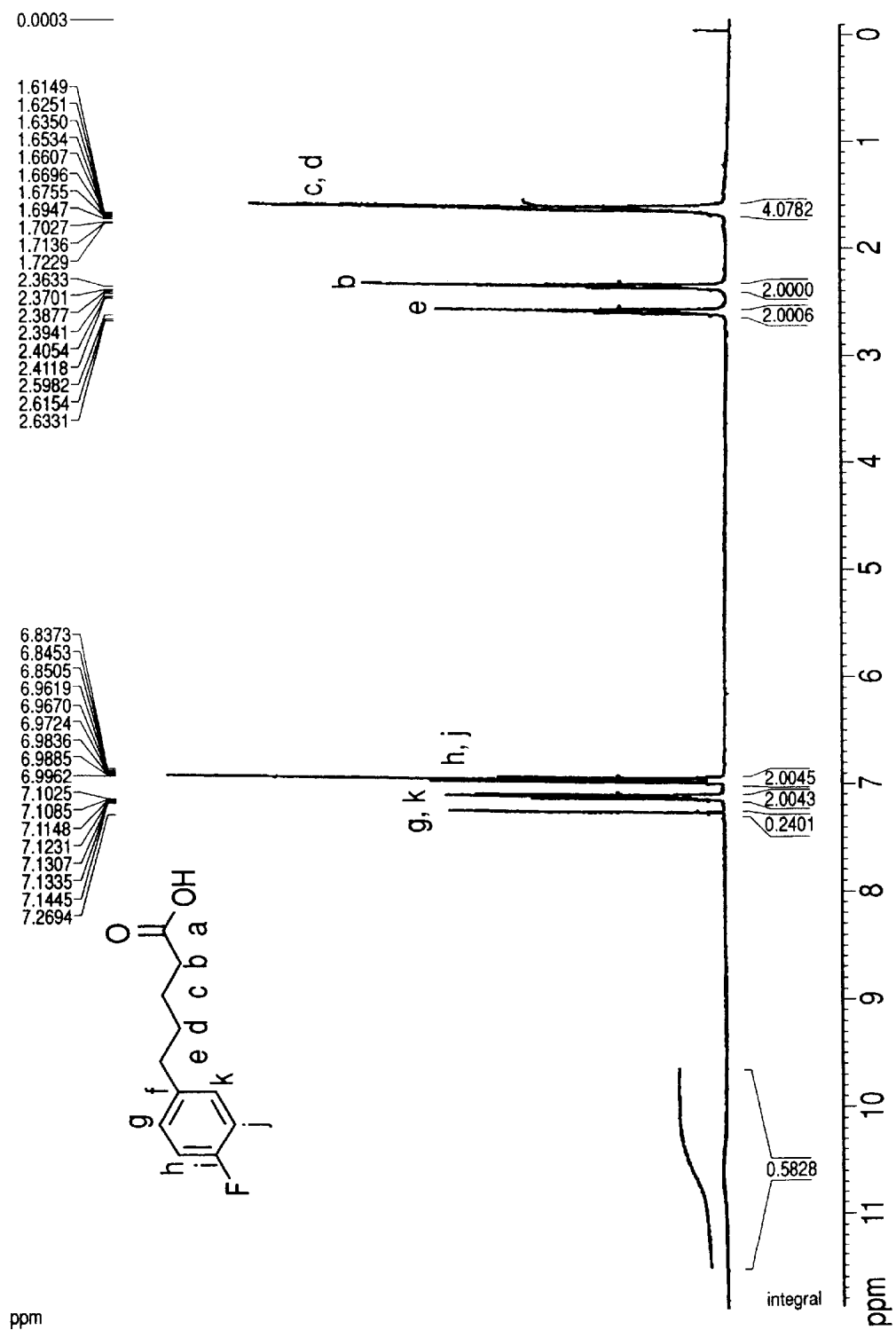
FIG. 13 is an NMR spectrum of FPVA biosynthesized as alkanoate as the material in Example E-1.

This precipitate was analyzed using nuclear magnetic resonance (FT-NMR: Bruker DPX400) under the following conditions: nuclide: 1H and 13C, solvent: heavy chloroform (containing TMS). FIG. 13 and Table 20 indicate the results of the analysis.

Example E-2

The strain H45 was inoculated in 200 ml of M9 medium containing 0.5% yeast extract (Difco Co.) and 0.1% FPVA and subjected to shake culture at 30° C. and at 125 strokes/min. After 24 hours, the bacterial cells were collected by centrifugation, washed with cold methanol once, and lyophilized.

This lyophilized pellet was suspended in 100 ml of chloroform and stirred at 60° C. for 20 hours to extract PHA. The extract solution was filtered with a 0.45-μm membrane filter and concentrated using a rotary evaporator. The concentrate was reprecipitated in cold methanol and the precipitate was collected and vacuum-dried to obtain PHA. The obtained PHA was subjected to methanolysis by the usual method and analyzed using gas chromatography-mass spectrometry (GC-MS, Shimadzu QP-5050, EI method) to identify the methyl ester of PHA monomer unit. Table 21 shows the results.

Example E-3

The P91 strain was inoculated in 200 ml of M9 medium containing 0.5% yeast extract (Difco Co.) and 0.1% FPVA and subjected to shake culture at 30° C. and at 125 strokes/min. After 24 hours, the bacterial cells were collected by centrifugation, suspended again in 200 ml of M9 medium containing 0.1% FPVA without a nitrogen source ($NH_4Cl$), and subjected to shake culture at 30° C. and 125 strokes/min. After 24 hours, the bacterial cells were collected by centrifugation, washed with cold methanol once, and lyophilized.

The lyophilized pellet was suspended in 100 ml of chloroform and stirred at 60° C. for 20 hours to extract PHA. The extract solution was filtered with a 0.45-μm membrane filter and concentrated using a rotary evaporator. The concentrate was reprecipitated in cold methanol and the precipitate was collected and vacuum-dried to obtain PHA. The obtained PHS was subjected to methanolysis by the usual method and analyzed using gas chromatography-mass spectrometry (GC-MS, Shimadzu QP-5050, EI method) to identify the methyl ester of PHS monomer unit. Table 22 lists the results.

Example E-4

The P161 strain was inoculated in 200 ml of M9 medium containing of 0.5% yeast extract (Difco Co.) and 0.1% FPVA and subjected to shake culture at 30° C. and 125 strokes/min. After 24 hours, the bacterial cells were collected by centrifugation, suspended again in 200 ml of M9 medium containing 0.1% FPVA without a nitrogen source ($NH_4Cl$), and subjected to shake culture at 30° C. and 125 strokes/min. After 24 hours, the bacterial cells were collected by centrifugation, washed with cold methanol once, and lyophilized.

The lyophilized pellet was suspended in 100 ml of chloroform and stirred at 60° C. for 20 hours to extract PHA. The extract solution was filtered with a 0.45-μm membrane filter and concentrated using a rotary evaporator. The concentrate was reprecipitated in cold methanol and the precipitate was collected and vacuum-dried to obtain PHA. The obtained PHA was subjected to methanolysis by the usual method, and analyzed using gas chromatography-mass spectrometry (GC-MS, Shimadzu QP-5050, EI method) to identify the methyl ester of PHA monomer unit. Table 23 shows the results.

Example E-5

Figure 14:
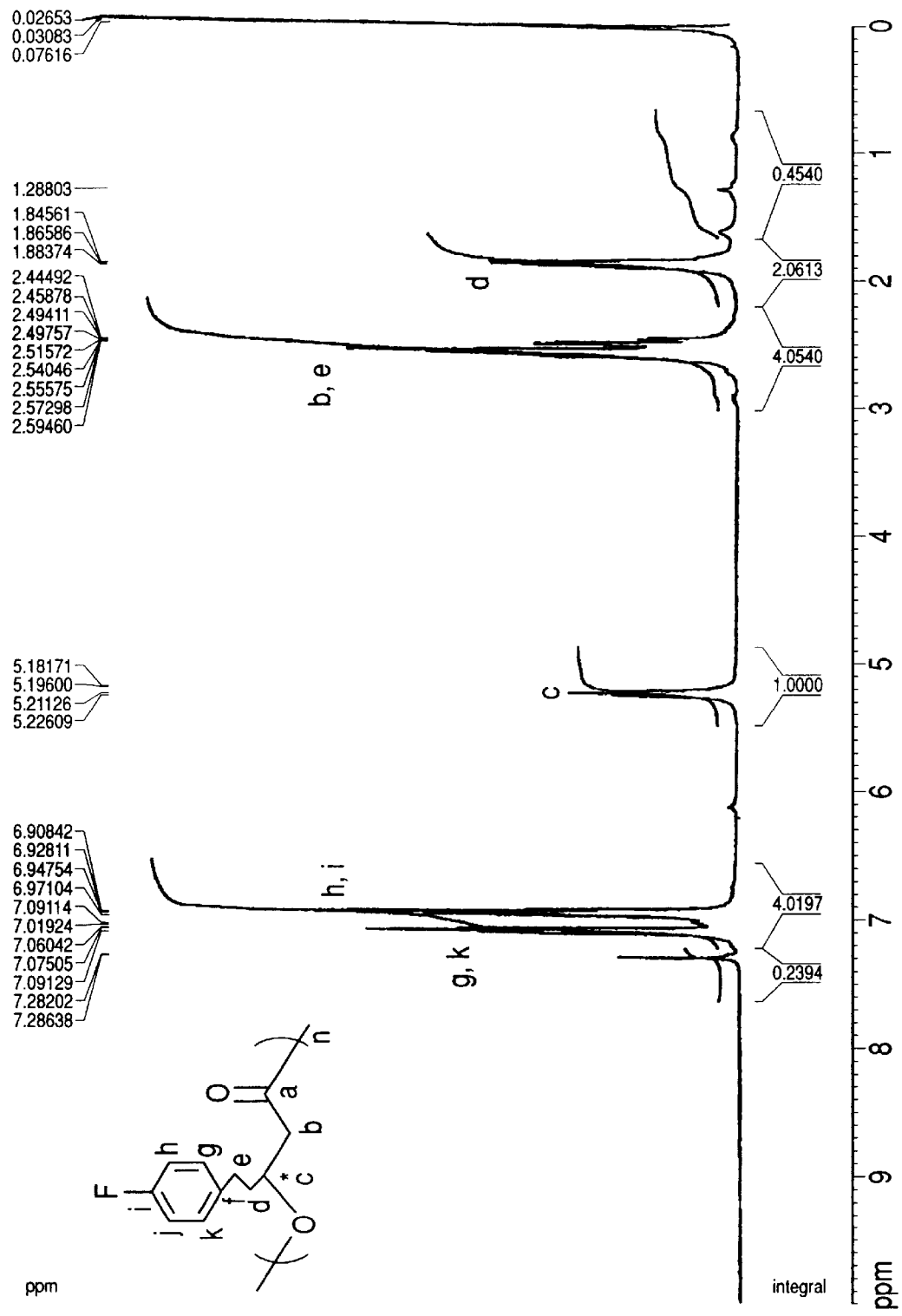
FIG. 14 is a $^1$H-NMR spectrum of PHA obtained by the production method of the present invention using FPVA as the material in Example E-5.
Figure 15:
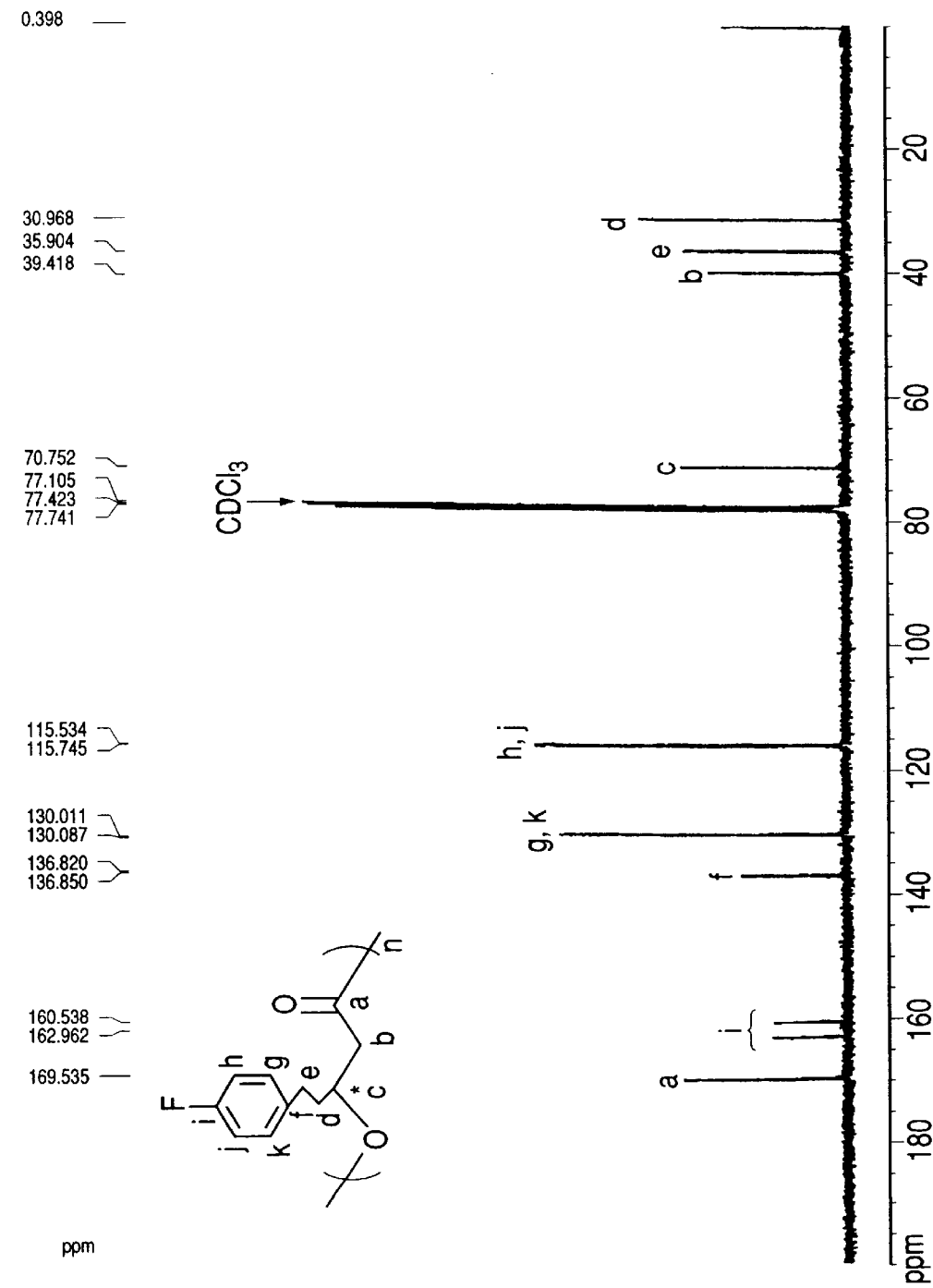
FIG. 15 is a $^{13}$C-NMR spectrum of PHA obtained by in Example E-5 using FPVA as the material.

We analyzed PHFPV derived from strain H45, using nuclear magnetic resonance spectrometer (FT-NMR: Bruker DPX400) under the following conditions: measured nuclides, $^1H$, $^{13}C$: used solvent, heavy chloroform (containing TMS). The results are shown in FIG. 14, Table 24, FIG. 15 and Table 25.

F

Following is an example of the process of the invention for producing polyhydroxyalkanoate consisting of 3-hydroxy-4-cyclohexylbutyric acid (3-HCHBA) monomer unit (Formula 8) by using 4-cyclohexylbutyric acid (CHBA, Formula 20) as a raw material.

Example F-1

Production of PHA Containing 3-hydroxy-4-cyclohexylbutyric Acid as a Monomer Unit by Strain YN2 (One-step Culture)

Colonies of strain YN2 grown on an M9 agar medium supplemented with 0.1% yeast extract were inoculated in 200 ml of a liquid M9 medium supplemented with 0.5% yeast extract and 0.1% 4-cyclohexylbutyric acid, and then cultured at 30° C. After 24 hours, the cells were collected by centrifugation, washed with methanol and then lyophilized.

After weighing, the lyophiled pellet was suspended in 100 ml of chloroform to extract PHA at 60° C. for 20 hours with mixing. Then the mixture was filtered through a 0.45 μm filter, the filtrate was concentrated by an evaporator. Cold methanol was added to the concentrate to reprecipitate the polymer material. The polymer was then vacuum-dried at room temperature and weighed. Table 26 shows the weight of the obtained lyophilized pellet and collected polymer and the yield of the polymer (CDW: cell mass (dry weight), PDW: polymer (dry weight)).

In the above mentioned prior art (Table 2), the yield of PHA comprised of 3-HCHBA unit was 89.1 mg/l culture. On the other hand, the result of the above example of the invention shows that the yield is 2.5 times higher than that. Moreover, the yield per dried cell mass was improved significantly.

The composition of the obtained PHA was analyzed as follows:

About 10 mg of PHA was put into a 25 ml eggplant type flask and dissolved in 2 ml of chloroform, then 2 ml of methanol containing 3% sulfuric acid was added to the solution and reacted for 3, 5 hours under reflux at 100° C. Upon completion of the reaction, 10 ml of deionized water was added to the solution and shaken vigorously for 10 minutes. Subsequently, the separated lower chloroform layer was taken out and dried over magnesium sulfate, The methylesterified PHA components in the chloroform layer were identified by using a gas chromatograph-mass spectrometer (GC-MS, Shimadzu QP-5050, EI method). As a result, 98% of the PHA monomer units were 3-HCHBA of Formula (8), and 2% of them were 3-hydroxybutyric acid. A small amount of cyclohexyl methanol was also present.

As shown above, according to the production process of the invention, PHA containing 3-HCHBA at a significantly high level can be obtained. The effect of the yeast extract addition in the process of the invention was verified. The production process was a highly efficient method of high yield per unit volume of culture or weight of cell mass. Thus, it was verified that the present production process is highly efficient in both the high content of 3-HCHBA unit and the high yield.

Production of PHA containing 3-hydroxy-4-cyclohexylbutyric acid as a monomer unit by strain H45 (one-step culture).

Colonies of strain H45 grown on an M9 agar medium supplemented with 0.1% yeast extract were inoculated in 200 ml of a liquid M9 medium supplemented with 0.5% yeast extract and 0.1% 4-cyclohexylbutyric acid, and then cultured at 30° C. After 24 hours, the cells were collected by centrifugation, washed with methanol and then lyophilized.

After weighing, the lyophiled pellet was suspended in 100 ml of chloroform to extract PHA at 60° C. for 20 hours with mixing. Then the mixture was filtered through a 0.45 μm filter, the filtrate was concentrated by an evaporator. Cold methanol was added to the concentrate to reprecipitate the polymer material. The polymer was then vacuum dried at room temperature and weighed. Table 27 shows the weight of the obtained lyophilized pellet (CDW) and collected polymer (PDW) and the yield of the polymer.

In the above mentioned prior art (Table 2), the yield of PHA comprised of a 3-HCHBA unit was 89.1 mg/l culture. On the other hand, the result of the above example of the invention shows that the yield is 1.3 times higher than that. Moreover, the yield per unit dried cell mass was improved significantly.

The composition of the obtained PHA was analyzed as follows:

About 10 mg of PHA was put into a 25 ml eggplant type flask and dissolved in 2 ml of chloroform, then 2 ml of methanol containing 3% sulfuric acid was added to the solution and reacted for 3, 5 hours under reflux at 100° C. Upon completion of the reaction, 10 ml of deionized water was added to the solution and shaken vigorously for 10 minutes. Subsequently, the separated lower chloroform layer was taken out and dried over magnesium sulfate, The methylesterified PHA components in the chloroform layer were identified by using a gas chromatograph-mass spectrometer (GC-MS, Shimadzu QP-5050, EI method). As a result, 97% of the PHA monomer units were 3-HCHBA of Formula (8), and 3% of them were 3-hydroxybutyric acid. A small amount of cyclohexyl methanol was also present.

As shown above, according to the production process of the invention, PHA containing 3-HCHBA at a significantly high level can be obtained by strain H45 as well.

Production of PHA containing 3-hydroxy-4-cyclohexylbutyric acid as a monomer unit by strain P161 (one-step culture)

Colonies of strain H45 grown on an M9 agar medium supplemented with 0.1% yeast extract were inoculated in 200 ml of a liquid M9 medium supplemented with 0.5% yeast extract and 0.1% 4-cyclohexylbutyric acid, and then cultured at 30° C. After 24 hours, the cells were collected by centrifugation, washed with methanol and then lyophilized.

After weighing, the lyophiled pellet was suspended in 100 ml of chloroform to extract PHA at 60° C. for 20 hours with mixing. Then the mixture was filtered through a 0.45 μm filter, the filtrate was concentrated by an evaporator. Cold methanol was added to the concentrate to reprecipitate the polymer material. The polymer was then vacuum dried at room temperature and weighed. Table 28 shows the weight of the obtained lyophilized pellet and collected polymer and the yield of the polymer.

In the above mentioned prior art (Table 2), the yield of PHA comprised of 3-HCHBA unit was 89.1 mg/l culture. On the other hand, the result of the above example of the invention shows that the yield is 1.5 times higher than that. Moreover, the yield per dried cell mass was improved significantly.

The composition of the obtained PHA was analyzed as follows:

About 10 mg of PHA was put into a 25 ml eggplant type flask and dissolved in 2 ml of chloroform, then 2 ml of methanol containing 3% sulfuric acid was added to the solution and reacted for 3, 5 hours under reflux at 100° C. Upon completion of the reaction, 10 ml of deionized water was added to the solution and shaken vigorously for 10 minutes. Subsequently, the separated lower chloroform layer was taken out and dried over magnesium sulfate, The methylesterified PHA components in the chloroform layer were identified by using a gas chromatograph-mass spectrometer (GC-MS, Shimadzu QP-5050, EI method). As a result, 94% of the PHA monomer units were 3-HCHBA of Formula (8), and 6% of them were 3-hydroxybutyric acid. A small amount of cyclohexyl methanol was also present.

As shown above, according to the production process of the invention, PHA containing 3-HCHBA at a significantly high level can be obtained by strain P161 as well.

Example F-2

Production of PHA Containing 3-hydroxy-4-cyclohexylbutyric Acid Units Using Strain YN2 (Two Step Cultivation).

Strain YN2 colonies grown on an M9 agar medium containing 0.1% yeast extract were inoculated in an M9 liquid medium (200 mL) containing 0.5% yeast extract and 0.1% 4-cyclohexylbutyric acid, and then cultured at 30° C. After 24 hours, the cells were collected by centrifugation. Subsequently, the cells were transferred into a fresh M9 medium containing 0.1% 4-cyclohexylbutyric acid but free from NaCl and NH$_4$Cl, and cultured for 21 hours at 30° C. Subsequently, the cells were washed once with methanol and lyophilized.

This lyophilized pellet was weighed, and then the polymer was collected through the same process as that conducted in Example F-1. This polymer was vacuum dried at room temperature and weighed. The obtained amounts of the lyophilized pellet (CDW) and the collected polymer (PDW) and the yield are shown in Table 29.

While the yielded amount of PHA containing the units derived from 3-hydroxy-4-cycrohexylbutyric acid in the above mentioned ordinary report (Table 2) was 89.1 mg per liter of the culture medium, the example of the invention resulted in obtaining approximately 3.2 times of the yielded amount. And the yield per dry cell mass is also improved significantly.

The composition of the obtained PHA was evaluated with the same process as that conducted in Example of the invention F-1. Consequently, 99% of them were derived from units of 3-hydroxy-4-cyclohexylbutyric acid expressed as Formula (8) and 1% of them were units of 3-hydroxybutyric acid. A little amount of cyclohexyl methanol was also existed.

The molecular weight of the obtained polymer was determined as Mn=49000 and Mw=100000, with using GPC (TOSOH HLC-8020, column: Polymer laboratory PLgel MIXED-C (5 µm), solvent: chloroform, conversion into polystyrene).

The above mentioned results show that the production process using this invention enables obtaining PHA containing significantly high level of units derived from 3-hydroxy-4-cyclohexylbutyric acid expressed as the equation (8). The effect of adding yeast extract to the medium in the process of this invention was verified. Additionally, the yield per unit medium and the yield per unit cell mass were sufficiently improved. Thus the method of the invention is verified to be a highly efficient production method in both the high content of 3-hydroxy-4-cyclohexylbutyric acid unit in the polymer and the high yield.

Example F-1 and this Example were compared and then it was verified that the obtained PHA can also contain a significantly high level of 3-hydroxy-4-cyclohexylbutyric acid unit by using a process where the cells are cultured in a mineral medium containing yeast extract and 4-cyclohexylbutyric acid, and then transferred and cultured in a mineral medium not containing yeast extract.

Example F-3

Purification and NMR Analysis of PHA Consisting of 3-hydroxy-4-cyclohexylbutyric Acid Units The following purifying process was conducted in order to remove PHB (poly 3-hydroxybutyric acid) component that was mixed in and the component considered as cyclohexylmethanol from the polymer obtained in Example F-2.

The polymer was suspended in acetone, and extraction was conducted for 24 hours at 60° C. Supernatant liquid was collected with centrifugation and extraction from the precipitated segment with acetone was conducted again. This operation was repeated 5 times, and then the collected supernatant liquid was condensed and dried thoroughly with an evaporator. The thoroughly dried sample was dissolved in a small amount of chloroform, and then precipitated again in cold methanol. This operation was repeated 3 times, and then the obtained polymer was vacuum dried. The obtained dried polymer was weighed as 281 mg.

Figure 16:
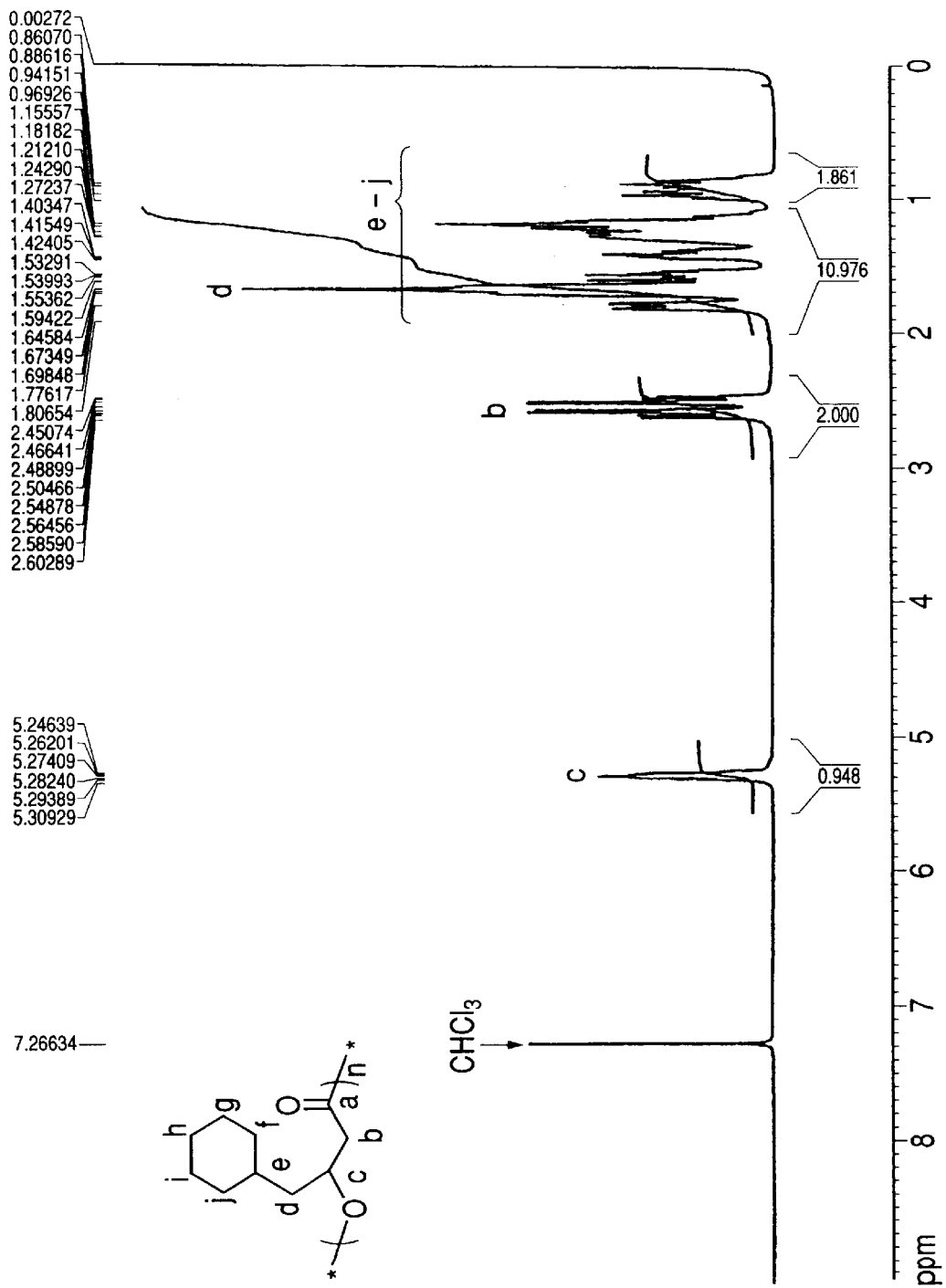
FIG. 16 is a $^1$H-NMR spectrum of PHA consisting of 3-hydroxy-4-cyclohexyl butyric acid unit purified in Example F-3.
Figure 17:
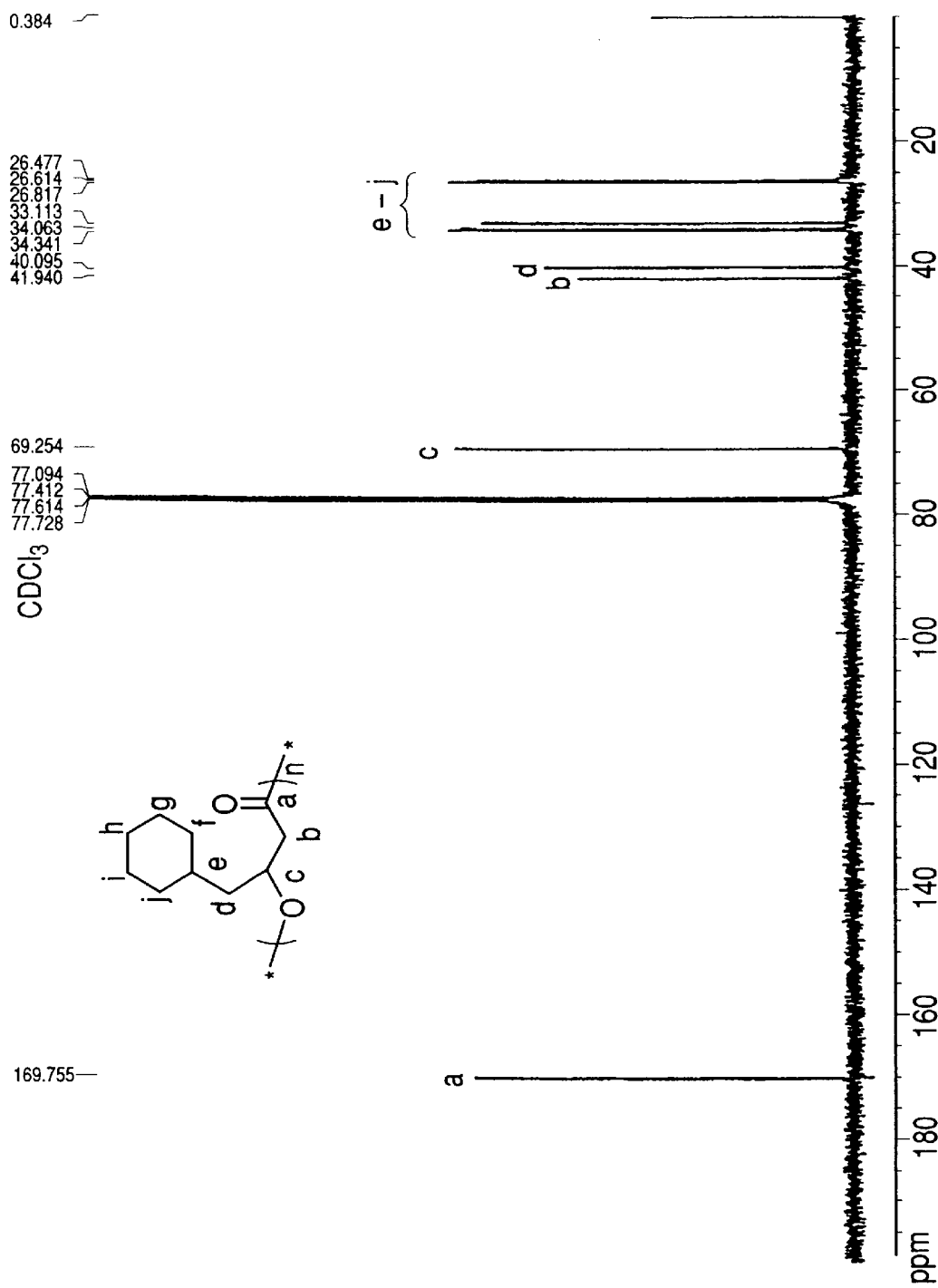
FIG. 17 is a $^{13}$C-NMR spectrum of PHA consisting of 3-hydroxy-4-cyclohexyl butyric acid unit purified in Example F-3.

$^1$H-NMR and $^{13}$C-NMR analyses of the polymer were conducted (FT-NMR: Bruker DPX 400, used solvent heavy chloroform (containing TMS). The chart of $^1$H-NMR is shown in FIG. 16, the assignments are in Table 30, and the chart of $^{13}$C-NMR is in FIG. 17, and the assignments are in Table 31.

From this evaluation, it is judged that PHB (poly 3-hydroxylbutyric acid) component that was mixed in and the component considered as cyclohexylmethanol were removed and PHA consisting of 3-hydroxy-4-cyclohexylbutyric acid was collected.

G

One example in which the production process of polyhydroalkanoate described in this invention is applied for production of the following compounds: polyhydroxyalkanoate consisting of the monomer units including 3-hydroxy-7-phenoxyheptanoic acid (3HPxHp) and 3-hydroxy-5-phenoxyvaleric acid (3HPxV) with using 7-phenoxyheptanoic acid as a material, which is the copolymer consisting of 3-hydroxy-7-phenoxyheptanoic acid (3HPxHp) and 3-hydroxy-5-phenoxyvaleric acid (3HPxV).

Example G-1

Production of the P (HPxV/HPxHp) Polymer with Using Strain YN2 (Yeast Extract - One Step Cultivation)

Strain YN2 was inoculated into 200 mL of M9 medium containing 0.5% yeast extract (produced by Difco) and 0.1% 7-phenoxyheptanoic acid (PxHpA), and shake-cultured with 125 strokes per minute and at 30° C. After 64 hours, cells were collected by centrifugation, washed once with cold methanol, lyophilized and weighed.

This lyophilized pellet was suspended into 100 mL of acetone and the polymer was extracted through mixing for 72 hours at the room temperature (23° C.). The extract was filtrated through a membrane-filter of 0.45 µm pore size and then concentrated by a rotary evaporator. Subsequently, the concentrate was reprecipitated in cold methanol and then the precipitate was collected. The obtained polymer was vacuum-dried and weighed.

The molecular weight of the obtained polymer was determined by gel permeation chromatography (GPC: Toso HLC-8020, column: Polymer laboratory•PLgel•MIXED-C•5 µm, solvent: chloroform, molecular weight converted in polystyrene).

Figure 18:
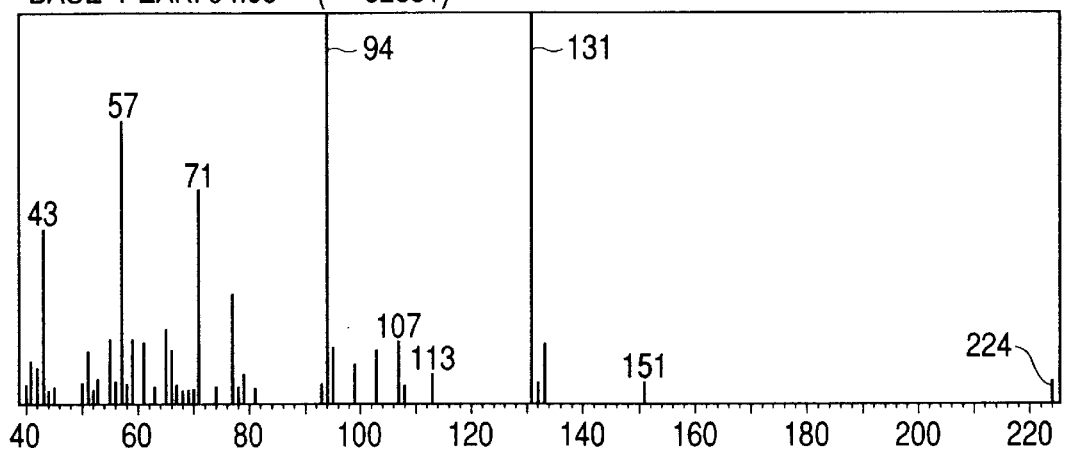
FIG. 18 is a mass spectrum of a 3-hydroxy-5-phenoxyvaleric acid (3HPxV) methyl ester obtained by GC-MS of the polymer produced in Example G-1.
Figure 19:
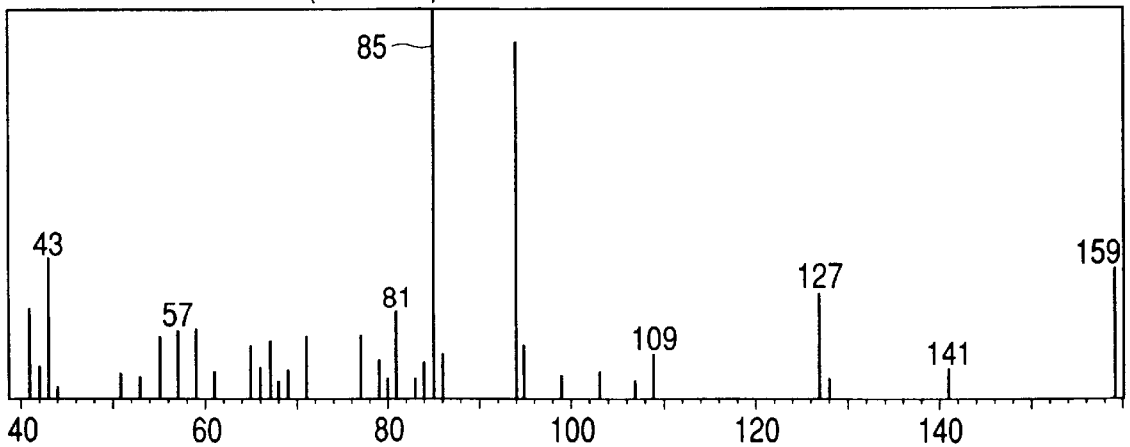
FIG. 19 is a mass spectrum of 3-hydroxy-7-phenoxyheptanoic acid (3HPxHp) methyl ester obtained by GC-MS of the polymer produced in Example G-1.

The composition of the obtained polymer unit was analyzed with the following process: the 5 mg of the polymer sample was put into the 25 mL eggplant shaped flask, 2 mL of chloroform and 2 mL of methanol containing 3% sulfuric acid (v/v) were added to the solution, and reflux for 3.5 hours at 100° C. was conducted. Separating occurred by adding water to the solution. Then the organic layer was analyzed with a gas chromatograph-mass spectrometer (GC-MS, Shimadzu QP-5050, column: DB-WAXETR (produced by J & W), EI method) and identification for methylesterified compounds of PHA monomer unit was conducted. The yield rate of the cells and the polymer and results of analysis of monomer units are shown in Table 32. The mass spectra of 3-hydroxy-5-phenoxyvaleric acid (3HPxV) methyl ester and 3-hydroxy-7-phenoxyheptanoic acid (3HPxHp) methyl ester, which were obtained using GC-MS, are shown in FIG. 18 and FIG. 19, respectively.

Consequently, it was suggested that using strain YN2, PHA copolymer consisting of only 2 units of 3-hydroxy-5-phenoxyvaleric acid (3HPxV) and 3-hydroxy-7-phenoxyheptanoic acid (3HPxHp), with 7-phenoxyheptanoic acid as a substrate, could be produced.

Example G-2

Production of P (HPxV/HPxHp) Polymer by Using Strain H45 (Yeast Extract Single-step Culture)

Strain H45 was inoculated in a 200 ml M9 culture medium containing 0.5% yeast extract (produced by Difco Co.) and 0.1% 7-phenoxyheptanoic acid (PxHpA), and shake-cultured at 30° C., 125 stroke/min. After 64 hr, cells were collected by centrifugation, washed once with cold methanol, lyophilized and weighed.

This lyophilized pellet was suspended in 100 ml of acetone, and a polymer was extracted by mixing for 72 hr at a room temperature (23° C.). The fluid extract was filtered by a membrane filter of 0.45 μm pore size, and condensed by a rotary evaporator. The condensed fluid was reprecipitated in cold methanol, and then the precipitate was collected and vacuum-dried to obtain a polymer to be weighed.

The molecular weight of the polymer obtained was measured by gel permeation chromatography (GPC: Toso, HLC-8020; Column: Polymer Laboratory, PLgel MIXED-C, 5 μm; Solvent: chloroform; Polystyrene-converted molecular weight).

Figure 20:
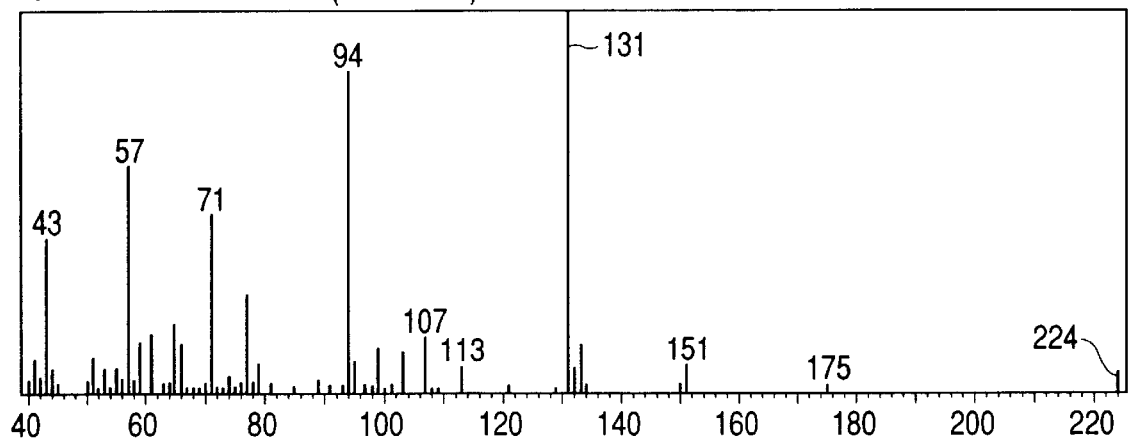
FIG. 20 is a mass spectrum of 3-hydroxy-5-phenoxyvaleric acid (3HPxV) methyl ester obtained by GC-MS of the polymer produced in Example G-2.
Figure 21:
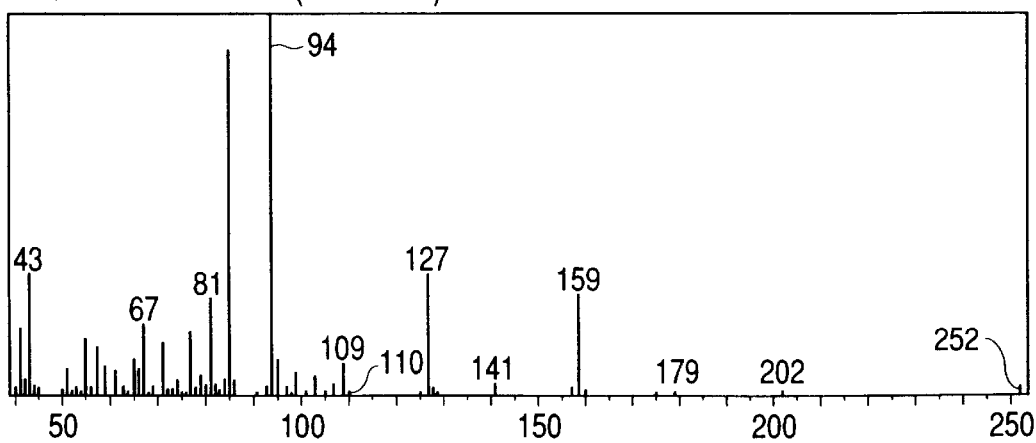
FIG. 21 is a mass spectrum of 3-hydroxy-7-phenoxyheptanoic acid (3HPxHp) methyl ester obtained by GC-MS of the polymer produced in Example G-2.

The unit composition of the polymer obtained was analyzed as follows: Five milligram of polymer sample put into a 25 ml eggplant-type flask was added with 2 ml of chloroform and 2 ml of methanol containing 3% (v/v) sulfuric acid, and was refluxed for 3.5 hr at 100° C. After addition of water for phase separation, the organic layer was analyzed by a gas-chromatograph-mass spectrometer (GC-MS: Shimadzu QP-5050; Column: DB-WAXETR (produced by J & W Co); EI method) to identify the methyl esterified compound of PHA monomer unit. The yield of the cells and polymer, and the result of analysis of monomer unit are shown in Table 33. The mass spectrum of 3-hydroxy-5-phenoxyvaleic acid (3HPxV) methyl ester and 3-hydroxy-7-phenoxyheptanoic acid (3HPxHp) methyl ester, which were obtained by GC-MS measurement, are shown in FIG. 20 and FIG. 21, respectively.

From the above result, it was shown that strain H45 can produce PHA copolymer composed of only two units of 3-hydroxy-5-phenoxyvaleic acid (3HPxV) and 3-hydroxy-7-phenoxyheptanoic acid (3HPxHp) by using 7-phenoxyheptanoic acid as substrate.

H

An example of the production method of polyhydroxyalkanoate in the present invention by using 8-phenoxyoctanoic acid (PxOA) as the raw material is shown here, where this method was applied to the production of a polyhydroxyalkanoate which is composed of monomer units derived from three kinds of substances including 3-hydroxy-4-phenoxybutyric acid (3HPxB), 3-hydroxy-6-phenoxyhexanoic acid (3HPxHx) and 3-hydroxy-8-phenoxyoctanoic acid (3HPxO), and is a copolymer composed of 3-hydroxy-4-phenoxybutyric acid (3HPxB), 3-hydroxy-6-phenoxyhexanoic acid (3HPxHx) and 3-hydroxy-8-phenoxyoctanoic acid (3HPxO).

Example H-1

Production of P (HPxB/HPxHx/HPxO) Polymer by Using Strain YN2 (Yeast Extract, Single-step Culture)

Strain YN2 was inoculated in 200 ml of an M9 medium containing 0.5% yeast extract (produced by Difco Co) and 0.1% 8-phenoxyoctanoic acid (PxOA), and shaking cultured at 30° C., 125 stroke/min. After 24 hr, cells were collected by centrifugation, washed once with cold methanol, lyophilized and weighed.

This lyophilized pellet was suspended in 100 ml of acetone, and the polymer was extracted by mixing for 72 hr at a room temperature (23° C.). The liquid extract was filtered by a membrane filter of 0.45 μm pore size, and condensed by a rotary evaporator. The concentrate was reprecipitated in cold methanol, and then the precipitate was collected and vacuum-dried to obtain a polymer to be weighed.

The molecular weight of the polymer obtained was measured by gel permeation chromatography (GPC: Toso HLC-8020; Column: Polymer Laboratory, PLgel MIXED-C, 5 μm; Solvent: chloroform; Polystyrene-converted molecular weight).

Figure 22:
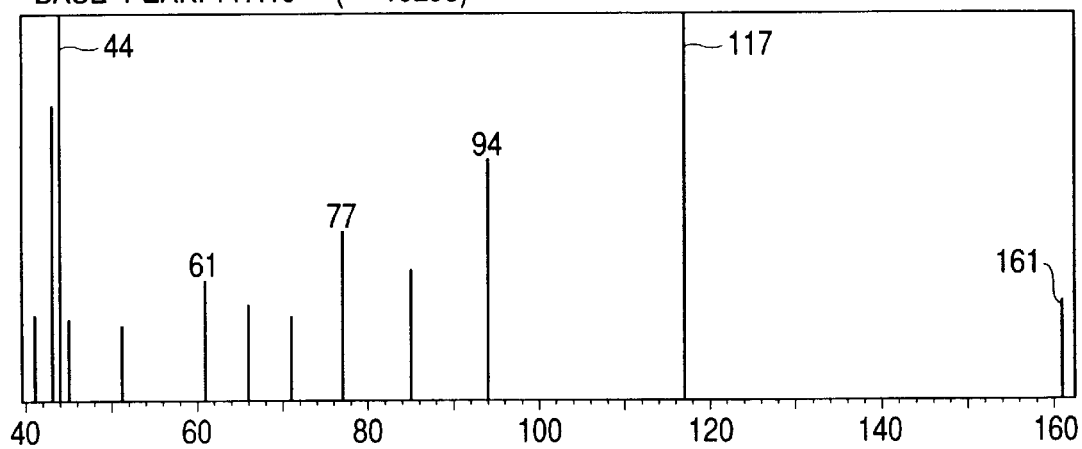
FIG. 22 is a mass spectrum of 3-hydroxy-4-phenoxy butyric acid (3HPxB) methyl ester obtained by GC-MS of the polymer produced in Example H-1.
Figure 23:
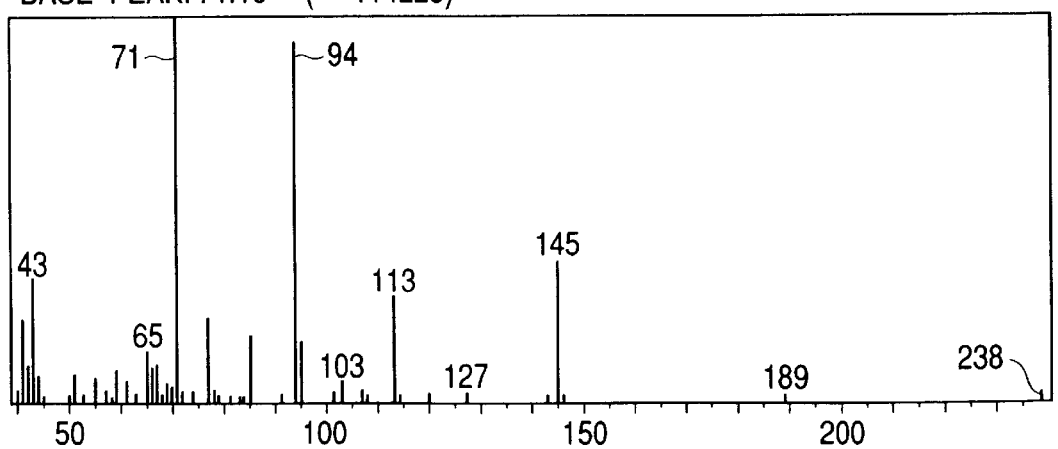
FIG. 23 is a mass spectrum of 3-hydroxy-6-phenoxy hexanoic acid (3HPxHx) methyl ester obtained by GC-MS of the polymer produced in Example H-1.
Figure 24:
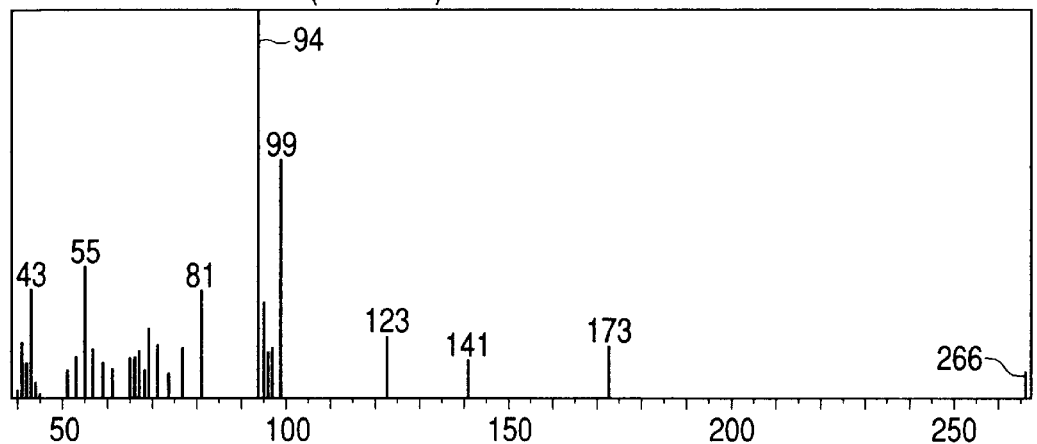
FIG. 24 is a mass spectrum of 3-hydroxy-8-phenoxy octanoic acid (3HPxO) methyl ester obtained by GC-MS of the polymer produced in Example H-1.

The unit composition of the polymer obtained was analyzed as follows: Five milligram of polymer sample put into a 25 ml eggplant-type flask was added with 2 ml of chloroform and 2 ml of methanol containing 3% (v/v) sulfuric acid, and was refluxed for 3.5 hr at 100° C. After addition of water for phase separation, the organic layer was analyzed by a gas-chromatograph-mass spectrometer (GC-MS: Shimadzu QP-5050; Column: DB-WAXETR (produced by J & W Co); EI method) to identify the methyl esterified compound of PHA monomer unit. The yield of the cells and polymer, and the result of analysis of monomer unit are shown in Table 34. The mass spectrum of 3-hydroxy-4-phenoxybutyric acid (3HPxB) methyl ester, 3-hydroxy-6-phenoxyhexanoic acid (3HPxHx) and 3-hydroxy-8-phenoxyoctanoic acid (3HPxO) methyl ester, which were obtained by GC-MS measurement, are shown in FIG. 22, FIG. 23 and FIG. 24, respectively.

From the above result, it was shown that strain YN2 can produce PHA copolymer composed of only three units of 3-hydroxy-4-phenoxybutyric acid (3HPxB), 3-hydroxy-6-phenoxyhexanoic acid (3HPxHx) and 3-hydroxy-8-phenoxyoctanoic acid (3HPxO) by using 8-phenoxyoctanoic acid as substrate.

Example H-2

Production of P (HPxB/HPxHx/HPxO) Polymer by Using Strain H45 (Yeast Extract Single-step Culture)

strain H45 was inoculated on M9 culture medium, 200 ml in volume, including 0.5% yeast extract (produced by Difco Co) and 0.1% 8-phenoxyoctanoic acid (PxOA), and its shaking culture was done at 30° C., 125 stroke/min. After 24 hr, cells were collected by centrifugation, washed once with cold methanol, lyophilized and weighed.

This lyophilized pellet was suspended in 100 ml of acetone, and a polymer was extracted by mixing for 72 hr at a room temperature (23° C.). The fluid extract was filtered by a membrane filter with 0.45 μm pore diameter, and was condensed by a rotary evaporator. The condensed fluid was reprecipitated in cold methanol, and then the precipitate alone was collected and vacuum-dried to obtain a polymer to be weighed.

The molecular weight of the polymer obtained was measured by gel permeation chromatography (GPC: Toso, HLC-8020; Column: Polymer Laboratory, PLgel MIXED-C, 5 μm; Solvent: chloroform; Polystyrene-converted molecular weight).

Figure 25:
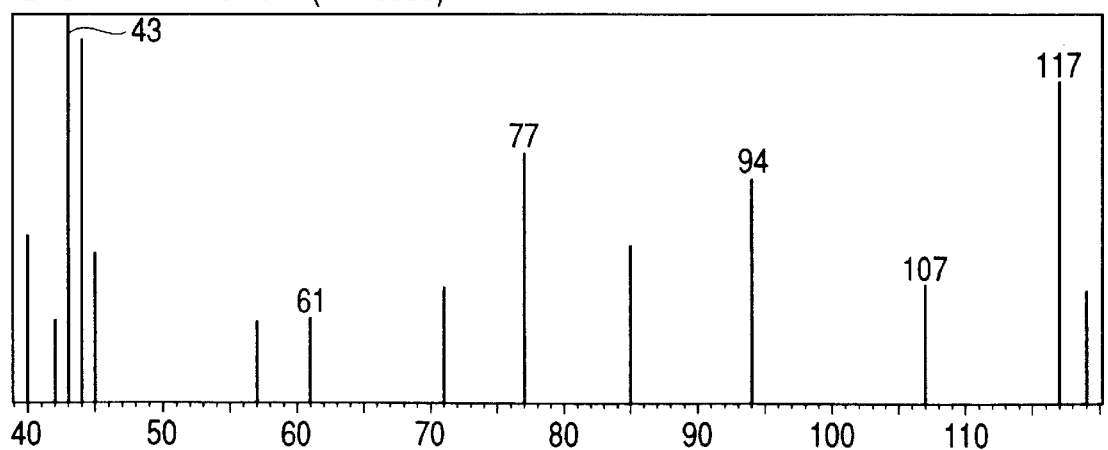
FIG. 25 is a mass spectrum of 3-hydroxy-4-phenoxy butyric acid (3HPxB) methyl ester obtained by GC-MS of the polymer produced in Example H-2.
Figure 26:
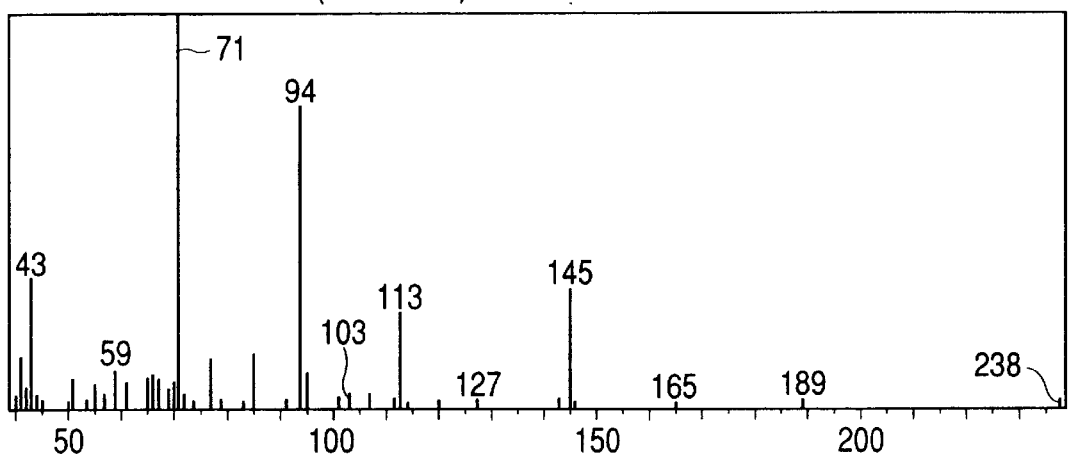
FIG. 26 is a mass spectrum of 3-hydroxy-6-phenoxy hexanoic acid (3HPxHx) methyl ester obtained by GC-MS of the polymer produced in Example H-2.
Figure 27:
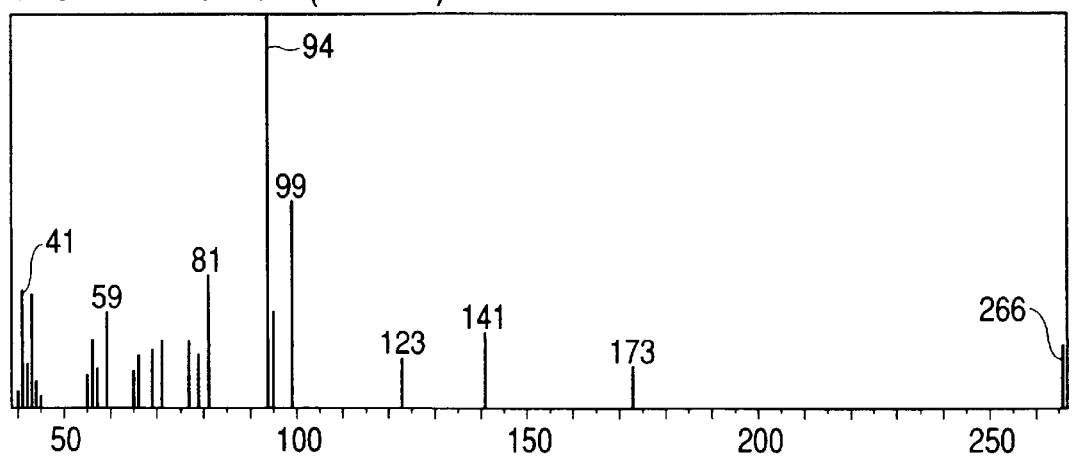
FIG. 27 is a mass spectrum of 3-hydroxy-8-phenoxy octanoic acid (3HPxO) methyl ester obtained by GC-MS of the polymer produced in Example H-2.

The unit composition of the polymer obtained was analyzed as follows: Five milligram of polymer sample put into a 25 ml eggplant-type flask was added with 2 ml of chloroform and 2 ml of methanol containing 3% (v/v) sulfuric acid, and was refluxed for 3.5 hr at 100° C. After addition of water for phase separation, the organic layer was analyzed by a gas-chromatograph-mass spectrometer (GC-MS: Shimadzu QP-5050; Column: DB-WAXETR (produced by J & W Co); EI method) to identify the methyl esterified compound of PHA monomer unit. The yield of the cells and polymer, and the result of analysis of monomer unit are shown in Table 35. The mass spectrum of 3-hydroxy-4-phenoxybutyric acid (3HPxB) methyl ester, 3-hydroxy-6-phenoxyhexanoic acid (3HPxHx) and 3-hydroxy-8-phenoxyoctanoic acid (3HPxO) methyl ester, which were obtained by GC-MS measurement, are shown in FIG. 25, FIG. 26 and FIG. 27, respectively.

From the above result, it was shown that strain H45 can produce PHA copolymer composed of only three units of 3-hydroxy-4-phenoxybutyric acid (3HPxB), 3-hydroxy-6-phenoxyhexanoic acid (3HPxHx) and 3-hydroxy-8-phenoxyoctanoic acid (3HPxO) by using 8-phenoxyoctanoic acid as substrate.

I

An example of the production method of polyhydroxyalkanoate in the present invention by using 11-phenoxyundecanoic acid (PxUDA) as the raw material is shown here, where this method was applied to the production of a polyhydroxyalkanoate which is composed of monomer units derived from three kinds of substances including 3-hydroxy-5-phenoxyvaleric acid (3HPxV), 3-hydroxy-7-phenoxyheptanoic acid (3HPxHp) and 3-hydroxy-9-phenoxynonanoic acid (3HPxN), and is a copolymer composed of 3-hydroxy-5-phenoxyvaleric acid (3HPxV), 3-hydroxy-7-phenoxyheptanoic acid (3HPxHp) and 3-hydroxy-9-phenoxynonanoic acid (3HPxN).

Example I-1

Production of P (HPxN/HPxHp/HPxV) Polymer by Using Strain YN2 (Yeast Extract, Single-step Culture)

Strain YN2 was inoculated in 200 ml of an M9 medium containing 0.5% yeast extract (produced by Difco Co) and 0.1% 11-phenoxyundecanoic acid (PxUDA), and cultured at 30° C. with shaking at 125 stroke/min. After 64 hr, the cells were collected by centrifugation, washed once with cold methanol, lyophilized and weighed.

This lyophilized pellet was suspended in 100 ml of acetone, and the polymer was extracted by mixing for 72 hr at a room temperature (23° C.). The extract was filtered by a membrane filter of 0.45 μm pore size and was condensed by a rotary evaporator. The condensate was reprecipitated in cold methanol, and then the precipitate was collected and vacuum-dried to obtain a polymer to be weighed.

The molecular weight of the polymer obtained was measured by gel permeation chromatography (GPC: Toso, HLC-8020; Column: Polymer Laboratory, PLgel MIXED-C, 5 μm; Solvent: chloroform; Polystyrene-converted molecular weight).

Figure 28:
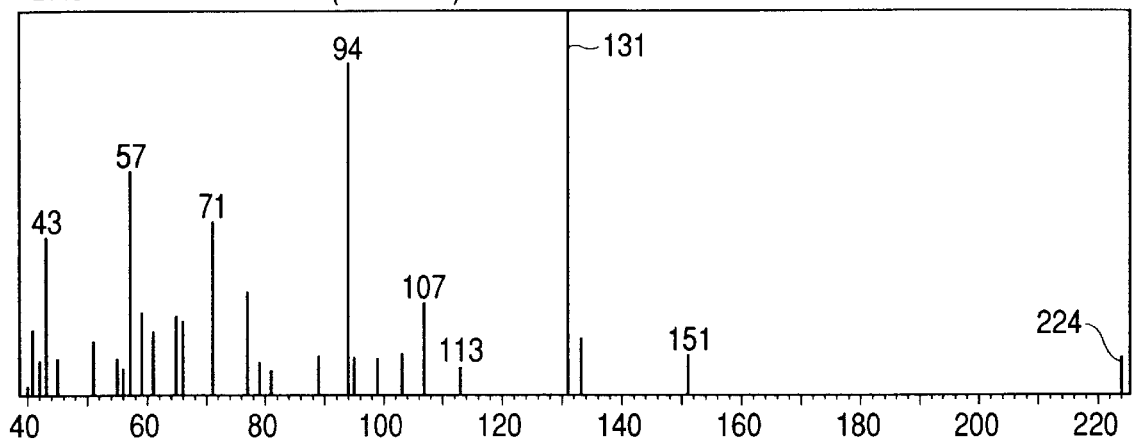
FIG. 28 is a mass spectrum of 3-hydroxy-5-phenoxyvaleric acid (3HPxV) methyl ester obtained by GC-MS of the polymer produced in Example I-1.
Figure 29:
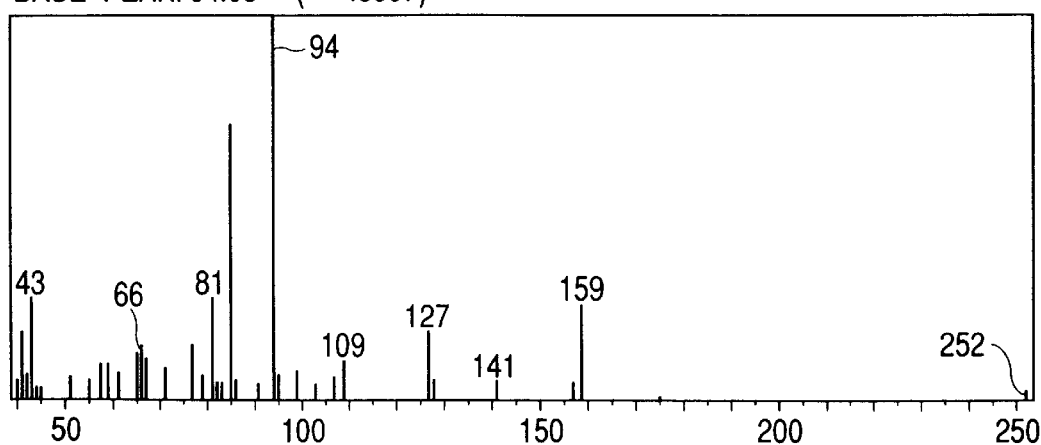
FIG. 29 is a mass spectrum of 3-hydroxy-7-phenoxyheptanoic acid (3HPxHp) methyl ester obtained by GC-MS of the polymer produced in Example I-1.
Figure 30:
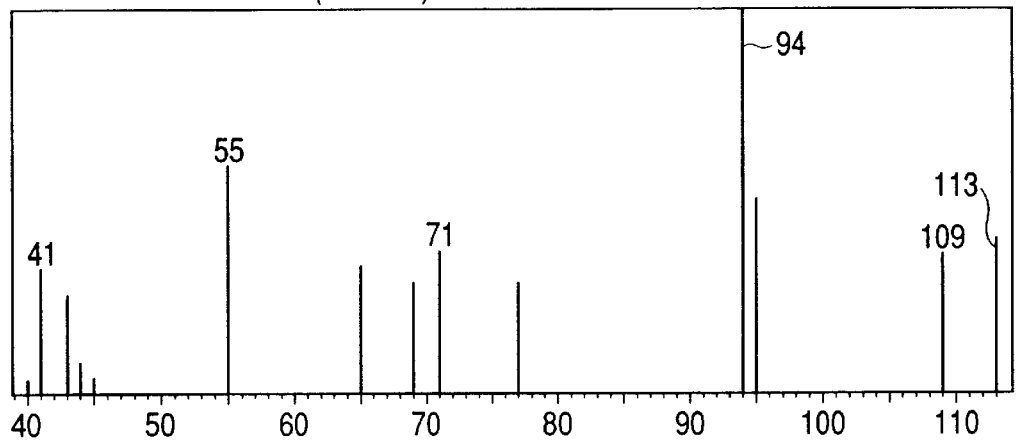
FIG. 30 is a mass spectrum of 3-hydroxy-9-phenoxy nonanoic acid (3HPxN) methyl ester obtained by GC-MS of the polymer produced in Example I-1.

The unit composition of the polymer obtained was analyzed as follows: Five milligram of polymer sample put into a 25 ml eggplant-type flask was added with 2 ml of chloroform and 2 ml of methanol containing 3% (v/v) sulfuric acid, and was refluxed for 3.5 hr at 100° C. After addition of water for phase separation, the organic layer was subjected to the analysis by gas-chromatograph-mass spectrometer (GC-MS: Shimadzu QP-5050; Column: DB-WAXETR (produced by J & W Co); EI method) to identify the methyl esterified compound of PHA monomer unit. The yield of the cells and polymer, and the result of analysis of the monomer unit are shown in Table 36. The mass spectrum of 3-hydroxy-5-phenoxyvaleric acid (3HPxV) methyl ester, 3-hydroxy-7-phenoxyheptanoic acid (3HPxHp) and 3-hydroxy-9-phenoxynonanoic acid (3HPxN) methyl ester, which were obtained by GC-MS measurement, are shown in FIG. 28, FIG. 29 and FIG. 30, respectively.

From the above result, it was shown that strain YN2 can produce PHA copolymer composed of only three units of 3-hydroxy-5-phenoxyvaleric acid (3HPxV), 3-hydroxy-7-phenoxyheptanoic acid (3HPxHp) and 3-hydroxy-9-phenoxynonanoic acid (3HPxN) by using 11-phenoxyundecanoic acid as substrate.

Example I-2

Production of P (HPxN/HPxHp/HPxV) Polymer by Using Strain H45 (Yeast Extract, Single-step Culture)

Strain H45 was inoculated in 200 ml of an M9 medium containing 0.5% yeast extract (produced by Difco Co) and 0.1% 11-phenoxyundecanoic acid (PxUDA), and cultured at 30° C., with shaking at 125 stroke/min. After 64 hr, the cells were collected by centrifugation, washed once with cold methanol, lyophilized and weighed.

This lyophilized pellet was suspended in 100 ml of acetone, and the polymer was extracted by mixing for 72 hr at a room temperature (23° C.). The extract was filtered by a membrane filter of 0.45 μm pore size and was condensed by a rotary evaporator. The condensed fluid was reprecipitated in cold methanol, and then the precipitate was collected and vacuum-dried to obtain a polymer to be weighed.

The molecular weight of the polymer obtained was measured by gel permeation chromatography (GPC: Toso, HLC-8020; Column: Polymer Laboratory, PLgel MIXED-C, 5 μm; Solvent: chloroform; Polystyrene-converted molecular weight).

Figure 31:
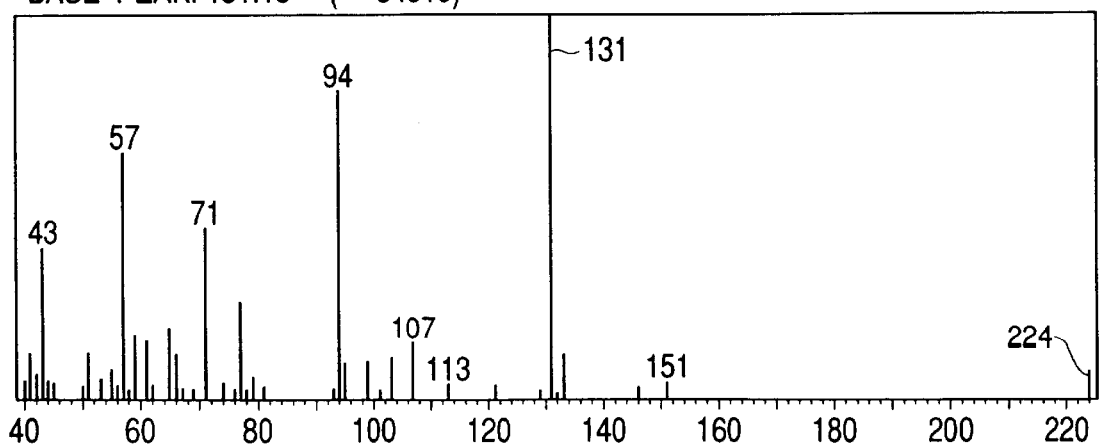
FIG. 31 is a mass spectrum of 3-hydroxy-5-phenoxyvaleric acid (3HPxV) methyl ester obtained by GC-MS of the polymer produced in Example I-2.
Figure 32:
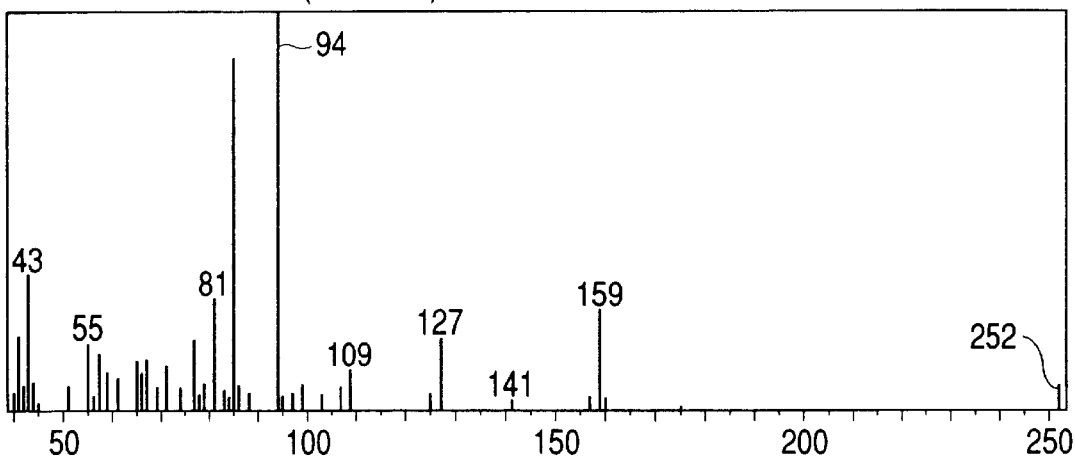
FIG. 32 is a mass spectrum of 3-hydroxy-7-phenoxyheptanoic acid (3HPxHp) methyl ester obtained by GC-MS of the polymer produced in Example I-2.
Figure 33:
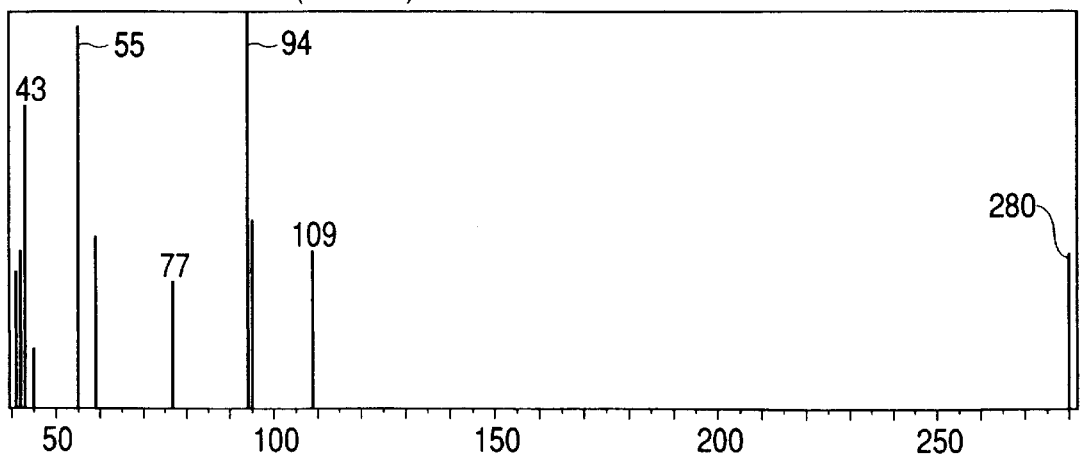
FIG. 33 is a mass spectrum of 3-hydroxy-9-phenoxy nonanoic acid (3HPxN) methyl ester obtained by GC-MS of the polymer produced in Example I-2.

The unit composition of the polymer obtained was analyzed as follows: Five milligram of polymer sample put into a 25 ml eggplant-type flask was added with 2 ml of chloroform and 2 ml of methanol containing 3% (v/v) sulfuric acid, and was refluxed for 3.5 hr at 100° C. After addition of water for phase separation, the organic layer was analyzed by a gas-chromatograph-mass spectrometer (GC-MS: Shimadzu QP-5050; Column: DB-WAXETR (produced by J & W Co); EI method) to identify the methyl esterified compound of PHA monomer unit. The yield of the cells and polymer, and the result of analysis of monomer unit are shown in Table 37. The mass spectrum of 3-hydroxy-5-phenoxyvaleric acid (3HPxV) methyl ester, 3-hydroxy-7-phenoxyheptanoic acid (3HPxHp) and 3-hydroxy-9-phenoxynonanoic acid (3HPxN) methyl ester, which were obtained by GC-MS measurement, are shown in FIG. 31, FIG. 32 and FIG. 33, respectively.

From the above result, it was shown that strain H45 can produce PHA copolymer composed of only three units of 3-hydroxy-5-phenoxyvaleric acid (3HPxV), 3-hydroxy-7-phenoxyheptanoic acid (3HPxHp) and 3-hydroxy-9-phenoxynonanoic acid (3HPxN) by using 11-phenoxyundecanoic acid as substrate.

J

An example of the production method of polyhydroxyalkanoate in the present invention by using 6-phenylhexanoic acid (PHxA) as the raw material is shown here, where this method was applied to the production of a polyhydroxyalkanoate composed of monomer units derived from 3-hydroxy-6-phenylhexanoic acid (3HPHx), that is, poly-3-hydroxy-6-phenylhexanoic acid (PHPHx), or to the production of a polyhydroxyalkanoate which is composed of monomer units derived from 3-hydroxy-6-phenylhexanoic acid (3HPHx) and 3-hydroxy-4-phenylbutyric acid (3HPB), and is a copolymer composed of 3-hydroxy-6-phenylhexanoic acid (3HPHx) and 3-hydroxy-4-phenylbutyric acid (3HPB).

Example J-1

Production of PHPHX Polymer by Using Strain YN2 (Yeast Extract, Single-step Culture)

Strain YN2 was inoculated in 200 ml of an M9 medium containing 0.5% yeast extract (produced by Difco Co) and 0.1% 6-phenylhexanoic acid (PHxA), and cultured at 30° C. with shaking at 125 stroke/min. After 27 hr, cells were collected by centrifugation, washed once with cold methanol, lyophilized and weighed.

This lyophilized pellet was suspended in 100 ml of acetone, and the polymer was extracted by mixing for 72 hr at room temperature (23° C.). The extract was filtered by a membrane filter of 0.45 μm pore size, and was condensed by a rotary evaporator. The condensed fluid was reprecipitated in cold methanol, and then the precipitate alone was collected and vacuum-dried to obtain a polymer to be weighed.

The molecular weight of the polymer obtained was measured by gel permeation chromatography (GPC: Toso, HLC-8020; Column: Polymer Laboratory, PLgel MIXED-C, 5 μm; Solvent: chloroform; Polystyrene-converted molecular weight).

Figure 34:
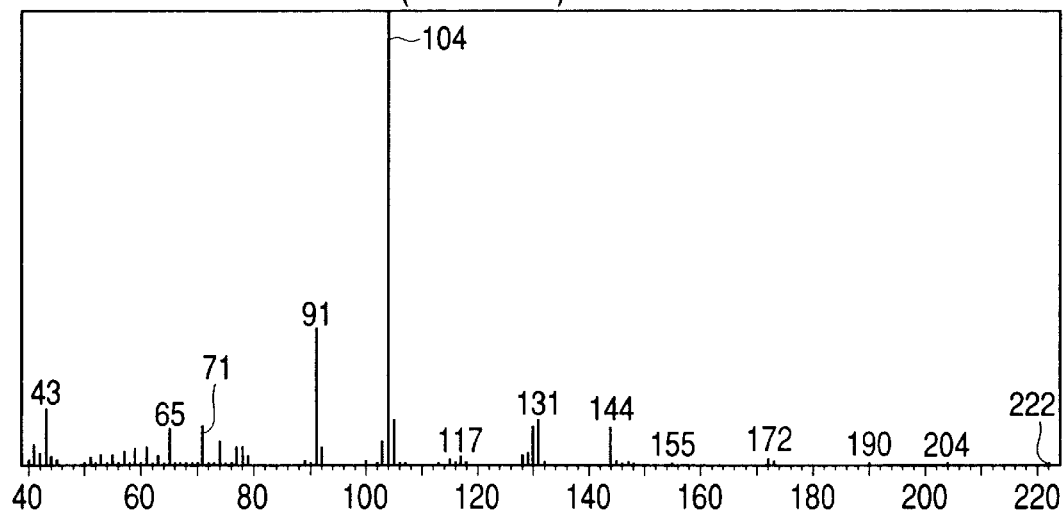
FIG. 34 is a mass spectrum of 3-hydroxy-6-phenyl hexanoic acid (3HPHx) methyl ester obtained by GC-MS of the polymer produced in Example J-1.

The unit composition of the polymer obtained was analyzed as follows: Five milligram of polymer sample put into a 25 ml eggplant-type flask was added with 2 ml of chloroform and 2 ml of methanol containing 3% (v/v) sulfuric acid, and was refluxed for 3.5 hr at 100° C. After addition of water and fractional separation of the fluid, the organic layer was analyzed by a gas-chromatograph-mass spectrometer (GC-MS: Shimadzu QP-5050; Column: DB-WAXETR (produced by J & W Co); EI method) to identify the methyl esterified compound of PHA monomer unit. The yield of cells and polymer, and the result of analysis of monomer unit are shown in Table 38. The mass spectrum of 3-hydroxy-6-phenylhexanoic acid (3HPHx) methyl ester obtained by GC-MS measurement is shown in FIG. 34.

From the above result, it was shown that strain YN2 can produce PHA polymer consisted of 3-hydroxy-6-phenylhexanoic acid (3HPHx) alone by using 6-phenylhexanoic acid as substrate.

Example J-2

Production of P (HPHx/HPB) Polymer by Using Strain H45 (Yeast Extract Single-step Culture)

Strain H45 was inoculated in 200 ml of an M9 culture medium containing 0.5% yeast extract (produced by Difco Co) and 0.1% 6-phenylhexanoic acid (PHxA), and was cultured at 30° C., with shaking at 125 stroke/min. After 27 hr, cells were collected by centrifugation, washed once with cold methanol, lyophilized and weighed.

This lyophilized pellet was suspended in 100 ml of acetone, and a polymer was extracted by mixing for 72 hr at a room temperature (23° C.). The extract was filtered by a membrane filter of 0.45 μm pore size, and was condensed by a rotary evaporator. The condensed fluid was reprecipitated in cold methanol, and then the precipitate alone was collected and vacuum-dried to obtain a polymer to be weighed.

The molecular weight of the polymer obtained was measured by gel permeation chromatography (GPC: Toso, HLC-8020; Column: Polymer Laboratory, PLgel MIXED-C, 5 μm; Solvent: chloroform; Polystyrene-converted molecular weight).

Figure 35:
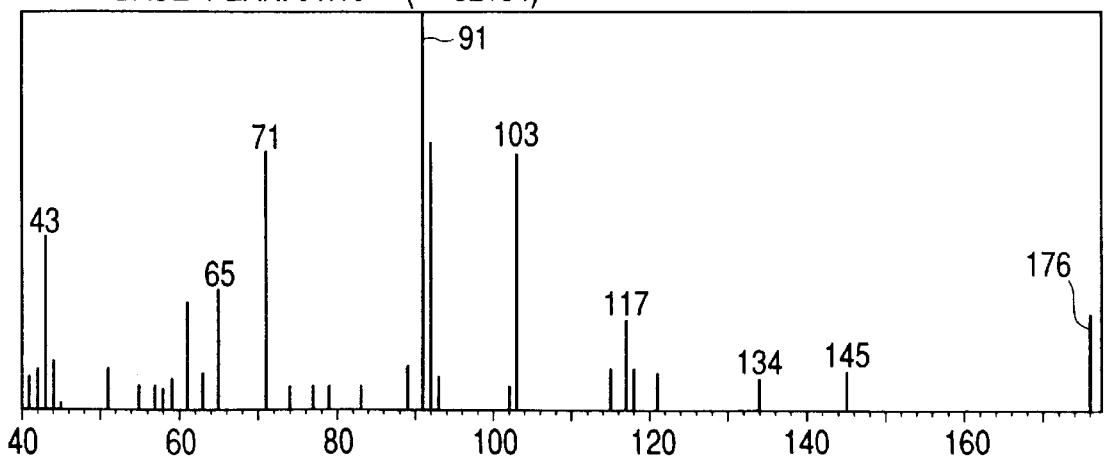
FIG. 35 is a mass spectrum of 3-hydroxy-4-phenyl butyric acid (3HPB) methyl ester obtained by GC-MS of the polymer produced in Example J-2.
Figure 36:
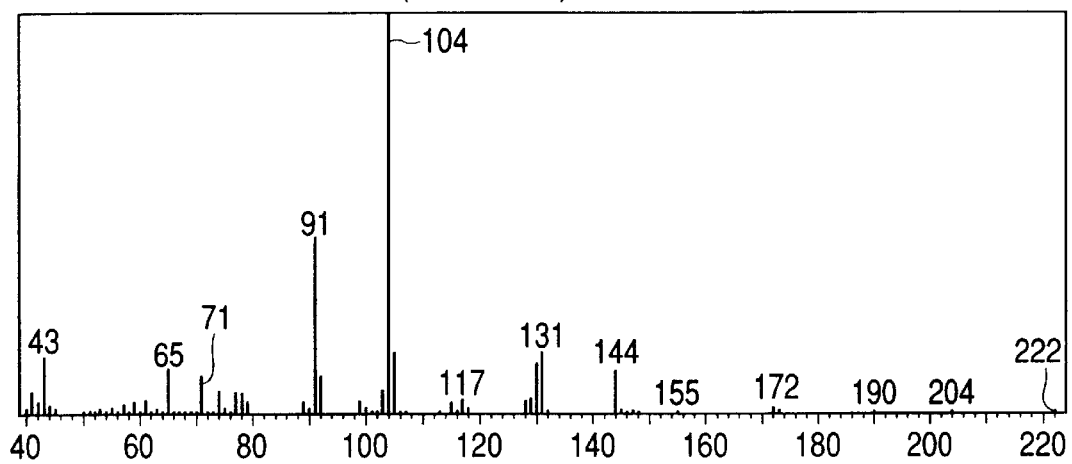
FIG. 36 is a mass spectrum of 3-hydroxy-6-phenyl hexanoic acid (3HPHx) methyl ester obtained by GC-MS of the polymer produced in Example J-2.

The unit composition of the polymer obtained was analyzed as follows: Five milligram of polymer sample put into a 25 ml eggplant-type flask was added with 2 ml of chloroform and 2 ml of methanol containing 3% (v/v) sulfuric acid, and was refluxed for 3.5 hr at 100° C. After addition of water for phase separation, the organic layer was analyzed by a gas-chromatograph-mass spectrometer (GC-MS: Shimadzu QP-5050; Column: DB-WAXETR (produced by J & W Co); EI method) to identify the methyl esterified compound of PHA monomer unit. The yield of cells and polymer, and the result of analysis of monomer unit are shown in Table 39. The mass spectrum of 3-hydroxy-4-phenylbutyric acid (3HPB) methyl ester and 3-hydroxy-6-phenylhexanoic acid (3HPHx), which were obtained by GC-MS measurement, are shown in FIG. 35 and FIG. 36, respectively.

From the above result, it was shown that strain H45 can produce PHA copolymer composed only of 3-hydroxy-4-phenylbutyric acid (3HPB) and 3-hydroxy-6-phenylhexanoic acid (3HPHx) by using 6-phenylhexanoic acid as substrate.

K

An example of the production method of polyhydroxyalkanoate in the present invention by using both 5-phenylvaleric acid (PVA) and 5-phenoxyvaleric acid (PXVA) as the raw materials is shown here, where this method was applied to the production of a polyhydroxyalkanoate which is composed of monomer units of 3-hydroxy-5-phenylvaleric acid (3HPV) and 3-hydroxy-5-phenoxyvaleric acid (3HPxV), and is a copolymer composed of 3-hydroxy-5-phenylvaleric acid (3HPV) and 3-hydroxy-5-phenoxyvaleric acid (3HPxV).

Example K-1

Production of P (HPV/HPxV) Polymer by Using Strain YN2 (Yeast Extract, Single-step Culture)

Strain YN2 was inoculated in 200 ml of an M9 culture medium containing 0.5% yeast extract (produced by Difco Co), 0.05% 5-phenylvaleric acid (PVA) and 0.05% 5-phenoxyvaleric acid (PxVA), and cultured at 30° C., with shaking at 125 stroke/min. After 24 hr, cells were collected by centrifugation, washed once with cold methanol, lyophilized and weighed.

This lyophilized pellet was suspended in 100 ml of acetone, and the polymer was extracted by mixing for 72 hr at room temperature (23° C.). The extract was filtered by a membrane filter with 0.45 μm pore size, and was concentrated by a rotary evaporator. The concentrate was reprecipitated in cold methanol, and then the precipitate was collected and vacuum-dried to obtain a polymer to be weighed.

The molecular weight of the polymer obtained was measured by gel permeation chromatography (GPC: Toso, HLC-8020; Column: Polymer Laboratory, PLgel MIXED-C, 5 μm; Solvent: chloroform; Polystyrene-converted molecular weight).

Figure 37:
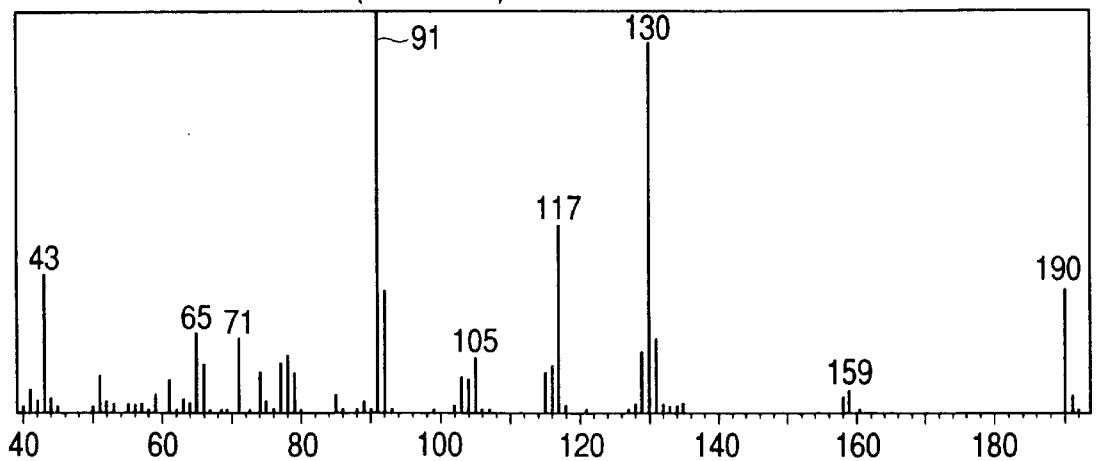
FIG. 37 is a mass spectrum of 3-hydroxy-5-phenyl valeric acid (3HPV) methyl ester obtained by GC-MS of the polymer produced in Example K-1.
Figure 38:
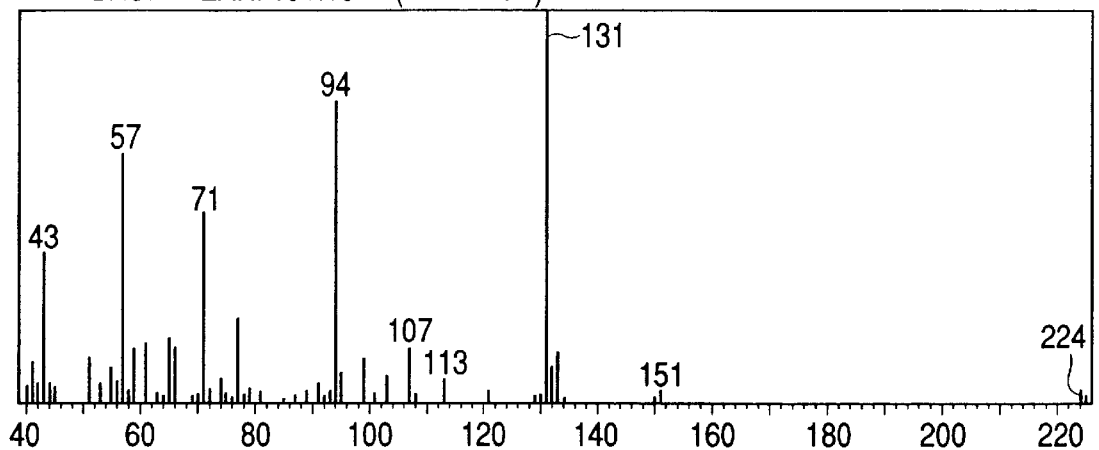
FIG. 38 is a mass spectrum of 3-hydroxy-5-phenoxyvaleric acid (3HPxV) methyl ester obtained by GC-MS of the polymer produced in Example K-1.

The unit composition of the polymer obtained was analyzed as follows: Five milligram of polymer sample put into a 25 ml eggplant-type flask was added with 2 ml of chloroform and 2 ml of methanol containing 3% (v/v) sulfuric acid, and was refluxed for 3.5 hr at 100° C. After addition of water and fractional separation of the fluid, the organic layer was analyzed by a gas-chromatograph-mass spectrometer (GC-MS: Shimadzu QP-5050; Column: DB-WAXETR (produced by J & W Co); EI method) to identify the methyl esterified compound of PHA monomer unit. The yield of cells and polymer, and the result of analysis of monomer unit are shown in Table 40. The mass spectrum of 3-hydroxy-5-phenylvaleric acid (3HPV) methyl ester and 3-hydroxy-5-phenoxyvaleric acid (3HPxV), which were obtained by GC-MS measurement, are shown in FIG. 37 and FIG. 38, respectively.

From the above result, it was shown that strain YN2 can produce PHA copolymer composed only of 3-hydroxy-5-phenylvaleric acid (3HPv) and 3-hydroxy-5-phenoxyvaleric acid (3HPxV) corresponding to 5-phenylvaleric acid and 5-phenoxyvaleric acid as substrates.

Example K-2

Production of P (HPV/HPxV) Polymer by Using Strain H45 (Yeast Extract, Single-step Culture)

Strain H45 was inoculated into 200 ml of an M9 culture medium containing 0.5% yeast extract (produced by Difco Co), 0.05% 5-phenylvaleric acid (PVA) and 0.05% 5-phenoxyvaleric acid (PxVA), and cultured at 30° C. with shaking at 125 stroke/min. After 24 hr, cells were collected by centrifugation, washed once with cold methanol, lyophilized and weighed.

This lyophilized pellet was suspended in 100 ml of acetone, and a polymer was extracted by mixing for 72 hr at room temperature (23° C.). The extract was filtered by a membrane filter of 0.45 μm pore size, and was concentrated by a rotary evaporator. The concentrate was reprecipitated in cold methanol, and then the precipitate was collected and vacuum-dried to obtain a polymer to be weighed.

The molecular weight of the polymer obtained was measured by gel permeation chromatography (GPC: Toso, HLC-8020; Column: Polymer Laboratory, PLgel MIXED-C, 5 μm; Solvent: chloroform; Polystyrene-converted molecular weight).

Figure 39:
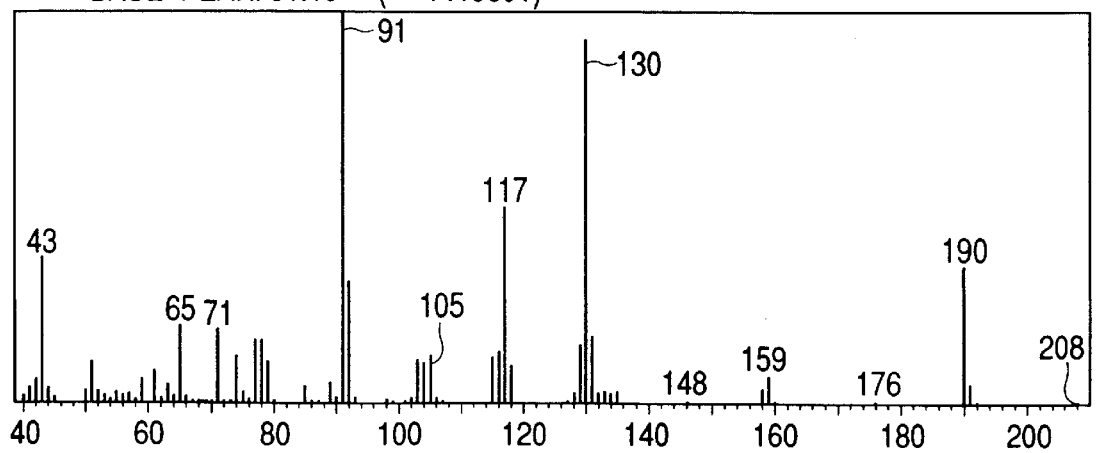
FIG. 39 is a mass spectrum of 3-hydroxy-5-phenyl valeric acid (3HPV) methyl ester obtained by GC-MS of the polymer produced in Example K-2.
Figure 40:
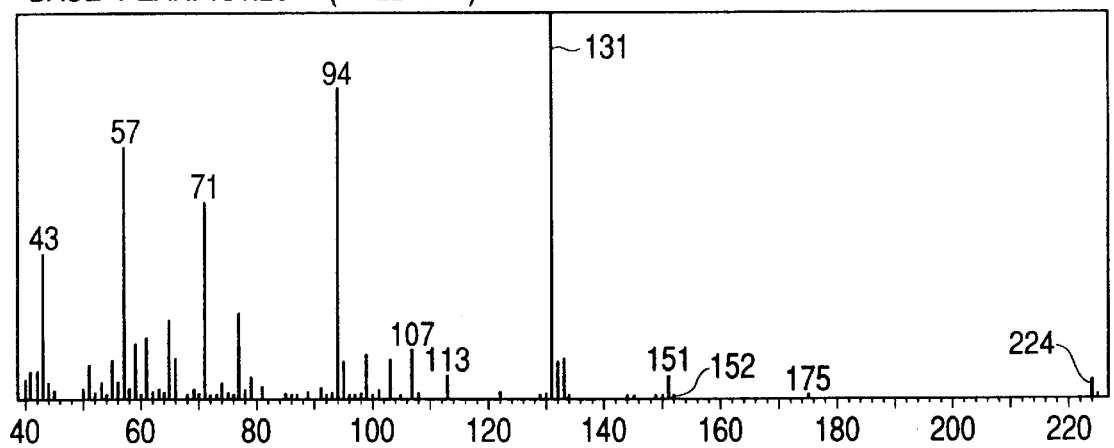
FIG. 40 is a mass spectrum of 3-hydroxy-5-phenoxyvaleric acid (3HPxV) methyl ester obtained by GC-MS of the polymer produced in Example K-2.

The unit composition of the polymer obtained was analyzed as follows: Five milligram of polymer sample put into a 25 ml eggplant-type flask was added with 2 ml of chloroform and 2 ml of methanol containing 3% (v/v) sulfuric acid, and was refluxed for 3.5 hr at 100° C. After addition of water for phase separation, the organic layer was analyzed by a gas-chromatograph-mass spectrometer (GC-MS: Shimadzu QP-5050; Column: DB-WAXETR (produced by J & W Co); EI method) to identify the methyl esterified compound of PHA monomer unit. The yield of cells and polymer, and the result of analysis of monomer unit are shown in Table 41. The mass spectrum of 3-hydroxy-5-phenylvaleric acid (3HPV) methyl ester and 3-hydroxy-5-phenoxyvaleric acid (3HPxV), which were obtained by GC-MS measurement, are shown in FIG. 39 and FIG. 40, respectively.

From the above result, it was shown that strain H45 can produce PHA copolymer composed only of 3-hydroxy-5-phenylvaleric acid (3HPV) and 3-hydroxy-5-phenoxyvaleric acid (3HPxV) corresponding to 5-phenylvaleric acid and 5-phenoxyvaleric acid as substrates.

TABLE 1

| Carbon source (Alkanoate) | Cell (Dry weight) (mg/l) | Polymer (Dry weight) (mg/l) | Yield (%) |
|---|---|---|---|
| 6-Phenoxyhexanoic acid | 950 | 100 | 10.5 |
| 8-Phenoxyoctanoic acid | 820 | 90 | 11 |
| 11-Phenoxyundecanoic acid | 150 | 15 | 10 |

TABLE 2

| NA:CHBA | CDW | PDW | Yield | Unit |
|---|---|---|---|---|
| 5:5 | 756.0 | 89.1 | 11.8 | NA, CHBA |
| 1:9 | 132.8 | 19.3 | 14.5 | NA, CHBA |

CDW: Cell dry weight (mg/l)
PDW: Polymer dry weight (mg/l)
Yield: PDW/CDW (%)

TABLE 3

| | P. putida P91 |
|---|---|
| Cell (Dry weight) | 520 mg/l |
| Polymer (Dry weight) | 14 mg/l |
| Polymer (Dry weight)/Cell (Dry weight) | 2.7% |
| Polymer molecular weight | Mn = 42,000 |
| | Mw = 84,000 |
| Monomer unit composition (area ratio) | |
| 3-hydroxy butyric acid | 0% |
| 3-hydroxy valeric acid | 0% |
| 3-hydroxy hexanoic acid | 0% |
| 3-hydroxy heptanoic acid | 0% |
| 3-hydroxy octanoic acid | 0% |
| 3-hydroxy nonanoic acid | 0% |
| 3-hydroxy decanoic acid | 0% |
| 3-hydroxy-4-phenoxy butyric acid | 100% |

TABLE 4

| | P. putida P91 |
|---|---|
| Cell (Dry weight) | 590 mg/l |
| Polymer (Dry weight) | 8 mg/l |
| Polymer (Dry weight)/Cell (Dry weight) | 1.4% |
| Monomer unit composition (area ratio) | |
| 3-hydroxy butyric acid | 0% |
| 3-hydroxy valeric acid | 0% |
| 3-hydroxy hexanoic acid | 0% |
| 3-hydroxy heptanoic acid | 0% |
| 3-hydroxy octanoic acid | 0% |
| 3-hydroxy nonanoic acid | 0% |
| 3-hydroxy decanoic acid | 0% |
| 3-hydroxy-4-phenoxy butyric acid | 100% |

TABLE 5

$^1$H NMR Spectrum
Resonance frequency: 400 MHz

| δ (ppm) | Assignment |
|---|---|
| 0.8 to 1.6 | Impurity |
| 2.71 | d; 2H, a |
| 3.97 | d; 2H, c |
| 5.47 | m; 1H, b |
| 6.79 | d; 2H, f, h |

TABLE 5-continued

¹H NMR Spectrum
Resonance frequency: 400 MHz

| δ (ppm) | Assignment |
|---|---|
| 6.90 | t; 1H, g |
| 7.19 | t; 2H, e, i | m: multiplet,
t: triplet,
d: doublet

TABLE 6

¹H NMR Spectrum
Resonance frequency: 400 MHz

| Chemical Shift/ppm | Integral value/H | type | Identification |
|---|---|---|---|
| 1.562 | | broad | Impurity |
| 1.863 | 4 | m | c, d |
| 2.474 | 2 | t | b |
| 3.994 | 2 | t | c |
| 6.905 | 2 | t | h, j |
| 6.964 | 1 | t | i |
| 7.28 | 2 | t | g, k |
| 9.35 | | broad | —COOH | m: multiplet,
t: triplet,
d: doublet

TABLE 7

| Dry cell (mg/l) | Dry polymer (mg/l) | Yield (dry polymer/dry cell, %) |
|---|---|---|
| 750 | 45 | 6.0 |

TABLE 8

¹H NMR Spectrum
Resonance frequency: 400 MHz

| Chemical Shift/ppm | Integral value/H | type | Identification |
|---|---|---|---|
| 1.562 | | broad | Impurity |
| 2.009 | 2 | m | d |
| 2.585 | 2 | d | b |
| 3.9 | 2 | m | e |
| 5.365 | 1 | m | c |
| 6.81 | 2 | m | h, j |
| 6.89 | 1 | t | i |
| 7.21 | 2 | t | g, k | m: multiplet,
t: triplet,
s: singlet,
d: doublet

TABLE 9

| Dry cell (mg/l) | Dry polymer (mg/l) | Yield (dry polymer/dry cell, %) |
|---|---|---|
| 850 | 95 | 11.2 |

TABLE 10

¹H NMR Spectrum
Resonance frequency: 400 MHz

| Chemical Shift/ppm | Integral/H | type | Identification |
|---|---|---|---|
| 1.85 | 4 | m | c, d |
| 2.46 | 2 | t | b |
| 3.95 | 2 | t | e |
| 6.83 | 2 | t | h, j |
| 6.97 | 2 | t | g, k |
| 10.15 | | broad | —COOH | m: multiplet, t: triplet, d: doublet

TABLE 11

| Dry cell (mg/l) | Dry polymer (mg/l) | Yield (dry polymer/dry cell, %) |
|---|---|---|
| 700 | 35 | 5.0 |

TABLE 12

¹H NMR Spectrum
Resonance frequency: 400 MHz

| Chemical Shift/ppm | Integral/H | type | Identification |
|---|---|---|---|
| to 1.55 | | | Impurity |
| 2.00 | 2 | m | d |
| 2.59 | 2 | d | b |
| 3.86 | 2 | m | c |
| 5.36 | 1 | m | c |
| 6.74 | 2 | m | h, j |
| 6.90 | 2 | t | g, k | m: multiplet, t: triplet, d: doublet

TABLE 13

| Dry cell (mg/l) | Dry polymer (mg/l) | Yield (dry polymer/dry cell, %) |
|---|---|---|
| 830 | 72 | 8.7 |

TABLE 14

| | *P. cichorii* H45 |
|---|---|
| Cell (Dry weight) | 1050 mg/l |
| Polymer (Dry weight) | 310 mg/l |
| Polymer (Dry weight)/Cell (Dry weight) | 30% |
| Polymer molecular weight | $Mn = 1.5 \times 10^5$ |
| | $Mw = 1.8 \times 10^5$ |
| Monomer unit composition (area ratio) | |
| 3-hydroxy butyric acid | 0% |
| 3-hydroxy valeric acid | 0% |
| 3-hydroxy hexanoic acid | 0% |
| 3-hydroxy heptanoic acid | 0% |
| 3-hydroxy octanoic acid | 0% |
| 3-hydroxy nonanoic acid | 0% |
| 3-hydroxy decanoic acid | 0% |
| 3-hydroxy-5-phenyl valeric acid | 100% |

TABLE 15

| | *P. cichorii* H45 |
|---|---|
| Cell (Dry weight) | 800 mg/l |
| Polymer (Dry weight) | 320 mg/l |
| Polymer (Dry weight)/Cell (Dry weight) | 40% |
| Polymer molecular weight | Mn = $9.7 \times 10^4$ |
| | Mw = $2.1 \times 10^5$ |
| Monomer unit composition (area ratio) | |
| 3-hydroxy butyric acid | 0% |
| 3-hydroxy valeric acid | 0% |
| 3-hydroxy hexanoic acid | 0% |
| 3-hydroxy heptanoic acid | 0% |
| 3-hydroxy octanoic acid | 0% |
| 3-hydroxy nonanoic acid | 0% |
| 3-hydroxy decanoic acid | 0% |
| 3-hydroxy-5-phenyl valeric acid | 100% |

TABLE 16

| | *P. putida* P91 |
|---|---|
| Cell (Dry weight) | 880 mg/l |
| Polymer (Dry weight) | 96 mg/l |
| Polymer (Dry weight)/Cell (Dry weight) | 11% |
| Monomer unit composition (area ratio) | |
| 3-hydroxy butyric acid | 0% |
| 3-hydroxy valeric acid | 0% |
| 3-hydroxy hexanoic acid | 0% |
| 3-hydroxy heptanoic acid | 0% |
| 3-hydroxy octanoic acid | 0% |
| 3-hydroxy nonanoic acid | 0% |
| 3-hydroxy decanoic acid | 0% |
| 3-hydroxy-5-phenyl valeric acid | 100% |

TABLE 17

| | *P. jessenii* P161 |
|---|---|
| Cell (Dry weight) | 650 mg/l |
| Polymer (Dry weight) | 410 mg/l |
| Polymer (Dry weight)/Cell (Dry weight) | 63% |
| Polymer molecular weight | Mn = $4.9 \times 10^4$ |
| | Mw = $9.2 \times 10^4$ |
| Monomer unit composition (area ratio) | |
| 3-hydroxy butyric acid | 0% |
| 3-hydroxy valeric acid | 0% |
| 3-hydroxy hexanoic acid | 0% |
| 3-hydroxy heptanoic acid | 0% |
| 3-hydroxy octanoic acid | 0% |
| 3-hydroxy nonanoic acid | 0% |
| 3-hydroxy decanoic acid | 0% |
| 3-hydroxy-5-phenyl valeric acid | 100% |

TABLE 18

$^1$H NMR Spectrum
Resonance frequency: 400 MHz

| δ (ppm) | Assignment |
|---|---|
| 0.9 to 1.7 | Broad peak → Impurities |
| 1.9 | m; 2H, —CH$_2$ → d |
| 2.4 to 2.6 | m; 4H, —CH$_2$ × 2 → b, e |
| 5.2 to 5.3 | m; 1H, —OCH → c |
| 6.9 to 7.0 | m; 3H, → Benzene proton → h, i, j |
| 7.1 | m; 2H, → Benzene proton → g, k |
| 7.3 | s; Solvent (CDCl$_3$) | m: multiplet, s: singlet

TABLE 19

$^{13}$C-NMR Spectrum
Resonance frequency: 100 MHz

| δ (ppm) | Assignment |
|---|---|
| 31.8 | —CH$_2$ → d |
| 35.8 | —CH$_2$ → e |
| 39.4 | —CH$_2$ → b |
| 70.9 | —CH → c |
| 77.1 to 77.7 | Solvent (CDCl$_3$) |
| 126.5 | —CH (benzene ring) → i |
| 128.7 to 128.9 | —CH (benzene ring) → g, h, j, k |
| 141.3 | C (benzene ring) → f |
| 169.7 | Carbonyl —C=O → a |

TABLE 20

| Chemical shift/ppm | type | Identification |
|---|---|---|
| 1.67 | m | c, d |
| 2.39 | t | b |
| 2.62 | t | e |
| 6.97 | t | h, j |
| 7.12 | t | g, k |
| 10.7 | broad | COOH | m: multiplet,
t: triplet

TABLE 21

| | *P. cichorii* H45 |
|---|---|
| Cell (Dry weight) | 1310 mg/l |
| Polymer (Dry weight) | 270 mg/l |
| Polymer (Dry weight)/Cell (Dry weight) | 21% |
| Monomer unit composition (area ratio) | |
| 3-hydroxy butyric acid | 0% |
| 3-hydroxy valeric acid | 0% |
| 3-hydroxy hexanoic acid | 0% |
| 3-hydroxy heptanoic acid | 0% |
| 3-hydroxy octanoic acid | 0% |
| 3-hydroxy nonanoic acid | 0% |
| 3-hydroxy decanoic acid | 0% |
| 3-hydroxy-5-(4-fluorophenyl) valeric acid | 100% |

TABLE 22

| | *P. putida* P91 |
|---|---|
| Cell (Dry weight) | 430 mg/l |
| Polymer (Dry weight) | 17 mg/l |
| Polymer (Dry weight)/Cell (Dry weight) | 4% |
| Monomer unit composition (area ratio) | |
| 3-hydroxy butyric acid | 0% |
| 3-hydroxy valeric acid | 0% |
| 3-hydroxy hexanoic acid | 0% |
| 3-hydroxy heptanoic acid | 0% |
| 3-hydroxy octanoic acid | 0% |
| 3-hydroxy nonanoic acid | 0% |
| 3-hydroxy decanoic acid | 0% |
| 3-hydroxy-5-(4-fluorophenyl) valeric acid | 100% |

TABLE 23

| | *P. jessenii* P161 |
|---|---|
| Cell (Dry weight) | 780 mg/l |
| Polymer (Dry weight) | 330 mg/l |
| Polymer (Dry weight)/Cell (Dry weight) | 42% |

TABLE 23-continued

|  | *P. jessenii* P161 |
|---|---|
| Monomer unit composition (area ratio) | |
| 3-hydroxy butyric acid | 0% |
| 3-hydroxy valeric acid | 0% |
| 3-hydroxy hexanoic acid | 0% |
| 3-hydroxy heptanoic acid | 0% |
| 3-hydroxy octanoic acid | 0% |
| 3-hydroxy nonanoic acid | 0% |
| 3-hydroxy decanoic acid | 0% |
| 3-hydroxy-5-(4-fluorophenyl) valeric acid | 100% |

TABLE 24

$^1$H-NMR Spectrum
Resonance frequency: 400 MHz

| δ (ppm) | Assignment |
|---|---|
| 0.9 to 1.7 | Broad peak → Impurities |
| 1.8 to 1.9 | m; 2H, —CH$_2$ → d |
| 2.4 to 2.6 | m; 4H, —CH$_2$ × 2 → b, e |
| 5.2 to 5.3 | m; 1H, —OCH → c |
| 6.9 to 7.0 | t; 2H, Proton at o-benzene → h, j |
| 7.1 | t; 2H, Proton at m-benzene → g, k |
| 7.3 | s; Solvent (CDCl$_3$) | m: multiplet,
t: triplet,
s: singlet

TABLE 25

$^{13}$C—NMR Spectrum
Resonance frequency: 100 MHz

| δ (ppm) | Assignment |
|---|---|
| 31.0 | —CH$_2$ → d |
| 35.9 | —CH$_2$ → e |
| 39.4 | —CH$_2$ → b |
| 70.5 | —CH → c |
| 77.1 to 77.7 | Solvent (CDCl$_3$) |
| 115.5, 115.7 | —CH at o-benzene → h, i |
| 130.0 | —CH at m-benzene → g, k |
| 136.3 | C at p-benzene → f |
| 160.5, 163.0 | —C at with F substitution → i |
| 169.7 | Carbonyl —C=O → a |

TABLE 26

| CDW | PDW | Yield |
|---|---|---|
| 1100 | 225 | 20.5 |

CDW: cell dry weight (mg/l)
PDW: Polymer dry weight (mg/l)
Yield rate: PDW/CDW (%)

TABLE 27

| CDW | PDW | Yield |
|---|---|---|
| 800 | 120 | 15.0 |

CDW: Cell dry weight (mg/l)
PDW: Polymer dry weight (mg/l)
Yield rate: PDW/CDW(%)

TABLE 28

| CDW | PDW | Yield |
|---|---|---|
| 750 | 130 | 17.3 |

CDW: Cell dry weight (mg/l)
PDW: Polymer dry weight (mg/l)
Yield rate: PDW/CDW(%)

TABLE 29

| CDW | PDW | Yield |
|---|---|---|
| 1100 | 285 | 25.9 |

CDW: Cell dry weight (mg/l)
PDW: Polymer dry weight (mg/l)
Yield rate: PDW/CDW (%)

TABLE 30

$^1$H Spectrum
Resonans frequency: 400 MHz

| δ (ppm) | Assignment |
|---|---|
| 0.9 to 1.8 | m; 11H, —CH$_2$ × 5 → f, g, h, i, j —CH → e |
| 1.5 to 1.7 | m; 2H, —CH$_2$ → d |
| 2.5 to 2.6 | dd; 2H, —CH$_2$ → b (further splitting due to remote H—H coupling with hexyl group) |
| 5.2 to 5.3 | m; 1H, —OCH → c | d: doublet, dd: double doublet

TABLE 31

$^{13}$C Spectrum
Resonans frequency: 100 MHz

| δ (ppm) | Assignment |
|---|---|
| 26.4 to 34.3 | hexyl —CH$_2$, —CH → e to j |
| 40.1 | —CH$_2$ → d |
| 41.9 | —CH$_2$ → b |
| 69.3 | —CH → c |
| 77.1 to 77.7 | Solvent (CDCl$_3$) |
| 169.8 | Carbonyl —C=O → a |

TABLE 32

| | |
|---|---|
| Cell (Dry weight) (mg/l) | 1295 |
| Polymer (Dry weight) (mg/l) | 350 |
| Number average molecular weight (Mn) × 10$^4$ | 3.9 |
| Weight average molecular weight (Mw) × 10$^4$ | 8.1 |
| 3-hydroxy-5-phenoxyvaleic acid (%) | 60.0 |
| 3-hydroxy-7-phenoxyheptanoic acid (%) | 40.0 |

TABLE 33

| | |
|---|---|
| Cell (Dry weight) (mg/l) | 1070 |
| Polymer (Dry weight) (mg/l) | 235 |
| Number average molecular weight (Mn) × 10$^4$ | 2.9 |
| Weight average molecular weight (Mw) × 10$^4$ | 5.7 |
| 3-hydroxy-5-phenoxyvaleic acid (%) | 27.9 |
| 3-hydroxy-7-phenoxyheptanoic acid (%) | 72.1 |

TABLE 34

| | |
|---|---|
| Cell (Dry weight) (mg/l) | 1315 |
| Polymer (Dry weight) (mg/l) | 415 |
| Number average molecular weight (Mn) × $10^4$ | 2.5 |
| Weight average molecular weight (Mw) × $10^4$ | 5.5 |
| 3-hydroxy-4-phenoxybutyric acid (%) | 2.2 |
| 3-hydroxy-6-phenoxyhexanoic acid (%) | 68.7 |
| 3-hydroxy-8-phenoxyoctanoic acid (%) | 29.1 |

TABLE 35

| | |
|---|---|
| Cell (Dry weight) (mg/l) | 990 |
| Polymer (Dry weight) (mg/l) | 225 |
| Number average molecular weight (Mn) × $10^4$ | 1.8 |
| Weight average molecular weight (Mw) × $10^4$ | 4.3 |
| 3-hydroxy-4-phenoxybutyric acid (%) | 2.4 |
| 3-hydroxy-6-phenoxyhexanoic acid (%) | 73.2 |
| 3-hydroxy-8-phenoxyoctanoic acid (%) | 24.4 |

TABLE 36

| | |
|---|---|
| Cell (Dry weight) (mg/l) | 1510 |
| Polymer (Dry weight) (mg/l) | 385 |
| Number average molecular weight (Mn) × $10^4$ | 1.8 |
| Weight average molecular weight (Mw) × $10^4$ | 3.8 |
| 3-hydroxy-5-phenoxyvaleric acid (%) | 32.0 |
| 3-hydroxy-7-phenoxyheptanoic acid (%) | 65.6 |
| 3-hydroxy-9-phenoxynonanoic acid (%) | 2.4 |

TABLE 37

| | |
|---|---|
| Cell (Dry weight) (mg/l) | 1015 |
| Polymer (Dry weight) (mg/l) | 120 |
| Number average molecular weight (Mn) × $10^4$ | 2.2 |
| Weight average molecular weight (Mw) × $10^4$ | 4.5 |
| 3-hydroxy-5-phenoxyvaleric acid (%) | 45.8 |
| 3-hydroxy-7-phenoxyheptanoic acid (%) | 47.8 |
| 3-hydroxy-9-phenoxynonanoic acid (%) | 6.4 |

TABLE 38

| | |
|---|---|
| Cell (Dry weight) (mg/l) | 1095 |
| Polymer (Dry weight) (mg/l) | 90 |
| Number average molecular weight (Mn) × $10^4$ | 6.8 |
| Weight average molecular weight (Mw) × $10^4$ | 17.9 |
| 3-hydroxy-6-phenylhexanoic acid (%) | 100.0 |

TABLE 39

| | |
|---|---|
| Cell (Dry weight) (mg/l) | 935 |
| Polymer (Dry weight) (mg/l) | 90 |
| Number average molecular weight (Mn) × $10^4$ | 6.9 |
| Weight average molecular weight (Mw) × $10^4$ | 15.5 |
| 3-hydroxy-4-phenylbutyric acid (%) | 1.7 |
| 3-hydroxy-6-phenylhexanoic acid (%) | 98.7 |

TABLE 40

| | |
|---|---|
| Cell (Dry weight) (mg/l) | 1300 |
| Polymer (Dry weight) (mg/l) | 330 |
| Number average molecular weight (Mn) × $10^4$ | 5.0 |
| Weight average molecular weight (Mw) × $10^4$ | 10.8 |
| 3-hydroxy-5-phenylvaleric acid (%) | 62.3 |
| 3-hydroxy-5-phenoxyvaleric acid (%) | 37.7 |

TABLE 41

| | |
|---|---|
| Cell (Dry weight) (mg/l) | 1050 |
| Polymer (Dry weight) (mg/l) | 165 |
| Number average molecular weight (Mn) × $10^4$ | 3.6 |
| Weight average molecular weight (Mw) × $10^4$ | 7.7 |
| 3-hydroxy-5-phenylvaleric acid (%) | 76.4 |
| 3-hydroxy-5-phenoxyvaleric acid (%) | 23.6 |

---

What is claimed is:

1. A polyhydroxyalkanoate comprising one or more of monomer units represented by Formula (1),

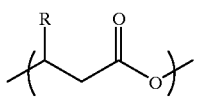
(1)

where R is at least one selected from the group represented by any one of Formulas (2), (3) and (4);

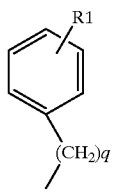
(2)

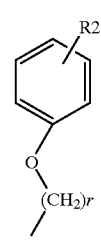
(3)

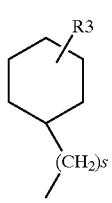
(4)

in Formula (2), R1 is selected from the group consisting of hydrogen atom (H), halogen atom, —CN, —NO$_2$, —CF$_3$, —C$_2$F$_5$ and —C$_3$F$_7$, and q is an integer of 1 to 8;

in Formula (3), R2 is selected from the group consisting of hydrogen atom (H), halogen atom, —CN, —NO$_2$, —CF$_3$, —C$_2$F$_5$ and —C$_3$F$_7$, and r is an integer of 1 to 8;

in Formula (4), R3 is selected from the group consisting of hydrogen atom (H), halogen atom, —CN, —NO$_2$, —CF$_3$, —C$_2$F$_5$ and —C$_3$F$_7$, and s is an integer of 1 to 8;

provided that following R is not selected:

when one kind of R is selected:
R being R1=H and q=2, or R1=H and q=3 in Formula (2),
R being R2=halogen and r=2, R2=—CN and r=3, R2=—NO$_2$ and r=3, or R2=H and r=1 or 2 in Formula (3), or
R being R3=H and s=1, 2 or 3 in Formula (4);

when two kinds of R are selected:
a combination of R being R1=H and q=3 and 5 respectively in Formula (2),
a combination of R being R2=H and r=2 and 4 respectively,
a combination of R being R2=H and r=2 and 6 respectively, and
a combination of R being R2=halogen and r=2 and 4 respectively in Formula (3);

when three kinds of R are selected:
a combination of R being R1=H and q=3, 5 and 7 respectively in Formula (2),
a combination of R being R2=H and r=1, 3 and 5 respectively, and a combination of R being R2=H and r=2, 4 and 6 respectively in Formula (3).

2. The polyhydroxyalkanoate according to claim 1, wherein the monomer unit is 3-hydroxy-5-(4-fluorophenyl) valeric acid unit of Formula (7):

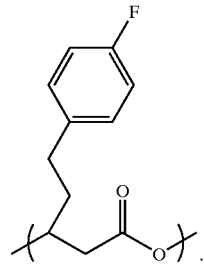
(7)

3. The polyhydroxyalkanoate according to claim 1, wherein the monomer units are 3-hydroxy-5-phenoxyvaleric acid unit of Formula (6) and 3-hydroxy-5-phenylvaleric acid unit of Formula (9):

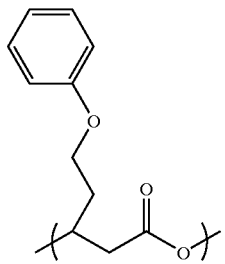
(6)

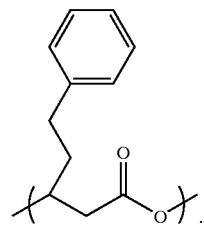
(9)

4. The polyhydroxyalkanoate according to claim 1, wherein the monomer units are 3-hydroxy-4-phenylbutyric acid unit of Formula (10) and 3-hydroxy-6-phenylhexanoic acid units of Formula (11):

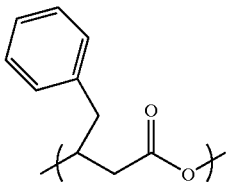
(10)

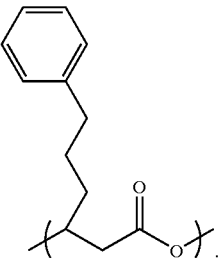
(11)

5. The polyhydroxyalkanoate according to any one of claims 1, 2, 3 and 4, wherein a number average molecular weight is 10 to 200 thousands.

* * * * *

UNITED STATES PATENT AND TRADEMARK OFFICE
CERTIFICATE OF CORRECTION

| | |
|---|---|
| PATENT NO. | : 6,521,429 B2 |
| DATED | : February 18, 2003 |
| INVENTOR(S) | : Tsutomu Honma et al. |

It is certified that error appears in the above-identified patent and that said Letters Patent is hereby corrected as shown below:

Title page,
Item [56], References Cited, FOREIGN PATENT DOCUMENTS, "2-642937 8/1997" should read -- 2642937 8/1997 --; and "2-989175 12/1999" should read -- 2989175 12/1999 --.
OTHER PUBLICATIONS, after "K. Fritzsche et al.,", "Makromol." should read -- Macromol. --.

Column 1,
Line 16, "advantages of" should read -- the advantage of being --; and
Line 17, "have" should read -- and have --.

Column 2,
Line 10, "has" should read -- have --;
Line 56, "-4-phenoxyburyric" should read -- -4-phenoxybutyric --;
Line 57, "3'-hydroxy" should read -- 3-hydroxy --; and
Line 62, "11-phenoxyunndecanoic" should read -- 11-phenoxyundecanoic --.

Column 3,
Line 56, "(%)" should read -- (%). --.

Column 5,
Line 16, "inventor" should read -- inventors --; and
Line 31, ", then completed the present invention" should be deleted.

Column 7,
Line 15, "polyhydroxyalkanoate" should read -- a polyhydroxyalkanoate --;
Line 16, "expected" should read -- expects to be --;
Line 17, "tion thereof" should read -- ble --; and
Line 59, "by" should be deleted.

Column 9,
Line 16, "by" should read -- by: --;
Line 19, "(12)" should read -- (12): --; and
Line 27, "from" should read -- from the --.

UNITED STATES PATENT AND TRADEMARK OFFICE
CERTIFICATE OF CORRECTION

PATENT NO. : 6,521,429 B2
DATED : February 18, 2003
INVENTOR(S) : Tsutomu Honma et al.

It is certified that error appears in the above-identified patent and that said Letters Patent is hereby corrected as shown below:

Column 10,
Line 31, "8)." should read -- 8. --;
Line 37, "having" should read -- having a --;
Line 50, "from" should read -- from the --;
Line 61, "is" should read -- are --;
Line 62, "having" should read -- having a-- and "on" should read -- on a --; and
Line 65, "into" should read -- into a --.

Column 11,
Line 2, "contain" should read -- contain a --;
Line 6, "is" should read -- are --;
Line 9, "into" should read -- into a --;
Line 35, "Japan" should read -- Japan. ¶ Preferred mode of the invention in the first embodiment of the method of producing a polyhydroxyalkanoate of the present invention will be individually and more definitely described below. --;
Line 36, "obtaining" should read -- obtaining a --; and
Line 38, "(PHPXB)" should read -- (PHPxB) --.

Column 12,
Lines 2 and 50, "repeats" should read -- repeating --; and
Lines 17 and 64, "obtaining" should read -- obtaining a --.

Column 13,
Line 33, "repeats" should read -- repeating --; and
Line 38, "obtaining" should read -- obtaining a --.

Column 18,
Line 61, "above described" should read -- above-described --; and
Line 62, "invention" should read -- invention of --.

Column 19,
Line 3, "extract," should read -- extract: --; and
Line 55, "to" should read -- to a --.

Column 20,
Line 22, "group" should read -- groups --; and
Line 56, "to" should read -- to a --.

Column 22,
Line 24, "group" should read -- groups --.

UNITED STATES PATENT AND TRADEMARK OFFICE
CERTIFICATE OF CORRECTION

PATENT NO. : 6,521,429 B2
DATED : February 18, 2003
INVENTOR(S) : Tsutomu Honma et al.

It is certified that error appears in the above-identified patent and that said Letters Patent is hereby corrected as shown below:

Column 24,
Line 8, "to" should read -- to a --.

Column 25,
Line 46, "units" should read -- unit --;
Line 55, "can" should read -- can be --; and
Line 65, "materials" should read -- materials, such as-- and "five" should read -- five, --.

Column 27,
Lines 48 and 58, "kind of group is" should read -- kinds of groups are --.
Column 28,
Line 14, "which" should read -- which a --;
Lines 15 and 20, "include" should read -- includes --;
Line 17, "unit" should read -- units --; and
Line 26, "little numbers" should read -- small number --.

Column 30,
Line 1, "accumulated" should read -- accumulate --;
Line 18, "above described reported" should read -- above-described reported --; and
Line 28, "is" should read -- are --.

Column 33,
Line 27, "names" should read -- names to --.

Column 34,
Line 66, "be also" should read -- also be --.

Column 35,
Line 33, "is becomes" should read -- becomes --.

Column 36,
Line 3, "has" should read -- has a --; and
Line 20, "example" should read -- examples --.

Column 37,
Line 20, "only" should read -- only a --.

Column 42,
Line 60, "-methanolysis" should read -- methanolysis --.

UNITED STATES PATENT AND TRADEMARK OFFICE
CERTIFICATE OF CORRECTION

PATENT NO. : 6,521,429 B2
DATED : February 18, 2003
INVENTOR(S) : Tsutomu Honma et al.

It is certified that error appears in the above-identified patent and that said Letters Patent is hereby corrected as shown below:

Column 43,
Line 36, "of" should read -- of the --.

Column 44,
Line 25, "QP5050," should read -- QP-5050, --; and
Line 32, "of" should read -- of the --.

Column 47,
Lines 6 and 57, "sulfate," should read -- sulfate. --; and
Line 24, "culture)." should read -- culture) --.

Column 48,
Lines 15 and 62, "vacuum dried" should read -- vacuum-dried --;
Line 48, "Cultivation)." should read -- Cultivation) --; and
Line 67, "cycrohexylbutyric" should read -- cyclohexylbutyric --.

Column 49,
Line 20, "significantly" should read -- a significantly --. -

Column 50,
Line 3, "droalkanoate" should read -- droxyalkanoate --.

Column 51,
Line 24, "Co);" should read -- (Co.); --; and
Line 58, "Co)" should read -- Co.) --.

Column 52,
Line 18, "Co);" should read -- Co.) --;
Line 39, "strain" should read -- Strain --; and
Line 41, "Co)" should read -- Co.) --.

Column 55,
Line 7, "PHPHX" should read -- PHPHx --.

Column 56,
Line 30, "(PXVA)" should read -- (PxVA) --.

UNITED STATES PATENT AND TRADEMARK OFFICE
CERTIFICATE OF CORRECTION

PATENT NO.   : 6,521,429 B2
DATED        : February 18, 2003
INVENTOR(S)  : Tsutomu Honma et al.

It is certified that error appears in the above-identified patent and that said Letters Patent is hereby corrected as shown below:

Column 58,
Table 4, "Monomer unit composition (area ratio)" should read
-- Monomer unit composition (area ratio) --.

Column 64,
Tables 30 and 31, "Resonans" should read -- Resonance --.

Signed and Sealed this

Seventh Day of September, 2004

JON W. DUDAS
*Director of the United States Patent and Trademark Office*

SEQUENCE LISTING

<160> NUMBER OF SEQ ID NOS: 1

<210> SEQ ID NO 1
<211> LENGTH: 1501
<212> TYPE: DNA
<213> ORGANISM: Pseudomonas jessenii P161 ; FERM P-17445

<400> SEQUENCE: 1

```
tgaacgctgg cggcaggcct aacacatgca agtcgagcgg                40
atgacgggag cttgctcctg aattcagcgg cggacgggtg                80
agtaatgcct aggaatctgc ctggtagtgg gggacaacgt               120
ctcgaaaggg acgctaatac cgcatacgtc ctacgggaga               160
aagcagggga ccttcgggcc ttgcgctatc agatgagcct               200
aggtcggatt agctagttgg tgaggtaatg gctcaccaag               240
gcgacgatcc gtaactggtc tgagaggatg atcagtcaca               280
ctggaactga gacacggtcc agactcctac gggaggcagc               320
```

-continued

| | |
|---|---|
| agtgggaat attggacaat gggcgaaagc ctgatccagc | 360 |
| catgccgcgt gtgtgaagaa ggtcttcgga ttgtaaagca | 400 |
| ctttaagttg ggaggaaggg cattaaccta atacgttagt | 440 |
| gttttgacgt taccgacaga ataagcaccg gctaactctg | 480 |
| tgccagcagc cgcggtaata cagagggtgc aagcgttaat | 520 |
| cggaattact gggcgtaaag cgcgcgtagg tggtttgtta | 560 |
| agttggatgt gaaagccccg ggctcaacct gggaactgca | 600 |
| ttcaaaactg acaagctaga gtatggtaga gggtggtgga | 640 |
| atttcctgtg tagcggtgaa atgcgtagat ataggaagga | 680 |
| acaccagtgg cgaaggcgac cacctggact gatactgaca | 720 |
| ctgaggtgcg aaagcgtggg gagcaaacag gattagatac | 760 |
| cctggtagtc cacgccgtaa acgatgtcaa ctagccgttg | 800 |
| ggagccttga gctcttagtg gcgcagctaa cgcattaagt | 840 |
| tgaccgcctg gggagtacgg ccgcaaggtt aaaactcaaa | 880 |
| tgaattgacg ggggcccgca caagcggtgg agcatgtggt | 920 |
| ttaattcgaa gcaacgcgaa gaaccttacc aggccttgac | 960 |
| atccaatgaa ctttccagag atggatgggt gccttcggga | 1000 |
| acattgagac aggtgctgca tggctgtcgt cagctcgtgt | 1040 |
| cgtgagatgt tgggttaagt cccgtaacga gcgcaaccct | 1080 |
| tgtccttagt taccagcacg taatggtggg cactctaagg | 1120 |
| agactgccgg tgacaaaccg gaggaaggtg gggatgacgt | 1160 |
| caagtcatca tggcccttac ggcctgggct acacacgtgc | 1200 |
| tacaatggtc ggtacagagg gttgccaagc cgcgaggtgg | 1240 |
| agctaatccc acaaaaccga tcgtagtccg gatcgcagtc | 1280 |
| tgcaactcga ctgcgtgaag tcggaatcgc tagtaatcgc | 1320 |
| gaatcagaat gtcgcggtga atacgttccc gggccttgta | 1360 |
| cacaccgccc gtcacaccat gggagtgggt tgcaccagaa | 1400 |
| gtagctagtc taaccttcgg gaggacggtt accacggtgt | 1440 |
| gattcatgac tggggtgaag tcgtaccaag gtagccgtag | 1480 |
| gggaacctgc ggctggatca c | 1501 |